US007799824B2

(12) United States Patent
Lagu et al.

(10) Patent No.: US 7,799,824 B2
(45) Date of Patent: Sep. 21, 2010

(54) QUATERNARY SALT CCR2 ANTAGONISTS

(75) Inventors: Bharat Lagu, Hillsborough, NJ (US); Michael Wachter, Bloomsbury, NJ (US)

(73) Assignee: OraPharma, Inc., Warminster, PA (US)

( * ) Notice: Subject to any disclaimer, the term of this patent is extended or adjusted under 35 U.S.C. 154(b) by 1210 days.

(21) Appl. No.: 11/159,018

(22) Filed: Jun. 22, 2005

(65) Prior Publication Data

US 2006/0293379 A1 Dec. 28, 2006

Related U.S. Application Data

(60) Provisional application No. 60/582,929, filed on Jun. 25, 2004.

(51) Int. Cl.
*A61K 31/38* (2006.01)
*A61K 31/4965* (2006.01)
*C07D 409/00* (2006.01)
*C07D 265/30* (2006.01)
*C07D 215/04* (2006.01)

(52) U.S. Cl. .................. 514/431; 514/116; 514/119; 514/255; 514/320; 514/331; 514/357; 514/396; 564/15; 564/16; 564/180; 540/593; 544/145; 544/147; 544/377; 544/393; 546/173; 546/196; 546/202; 546/205; 546/333; 546/337; 548/338.1; 548/517; 549/9; 549/12; 549/60; 549/355; 549/424

(58) Field of Classification Search .............. 549/9, 549/12, 60, 355, 424; 546/173, 196, 202, 546/205, 333, 337; 564/15, 16, 180; 548/338.1, 548/517; 540/593; 544/145, 149, 379, 393; 514/431, 510, 116, 119, 255, 320, 331, 357, 514/396, 422, 438, 450, 459, 617
See application file for complete search history.

(56) References Cited

U.S. PATENT DOCUMENTS

| 6,166,006 | A  | * | 12/2000 | Shiraishi et al. | ........ | 514/213.01 |
| 6,413,947 | B1 | * | 7/2002  | Shiraishi et al. | ........ | 514/110    |
| 6,627,651 | B1 | * | 9/2003  | Shiraishi et al. | ........ | 514/431    |
| 2007/0185099 | A1 | | 8/2007 | Blettner et al. | | |

FOREIGN PATENT DOCUMENTS

| EP | 1498138 | 1/2005 |
| WO | WO 99/32468 | 7/1999 |
| WO | WO 00/10965 | 3/2000 |
| WO | WO 00/37455 | 6/2000 |
| WO | WO 01/42224 | 6/2001 |
| WO | WO 03/089004 | 10/2003 |
| WO | WO 2006/012135 A1 | 2/2006 |

OTHER PUBLICATIONS

PCT International Search Report, dated Oct. 21, 2005, for PCT Int'l. Appln. No. PCT/US2005/022034.
Dawson, J. et al., "Targeting monocyte chemoattractant protein-1 signalling in disease", *Expert Opin. Ther. Targets*, 7(1):35-48 (2003).
Shiraishi, M. et al., "Discovery of Novel, Potent, and Selective Small Molecule CCR5 Antagonists as Anti-HIV-1 Agents: Synthesis and Biological Evaluation of Anilide Derivatives with a Quarternary Ammonium Moiety", *J. Med. Chem*, 43(10), 2049-2063 (2000).
Hashimoto H. et al., "Process Development of 4-[*N*-Methyl-*N*-(tetrahydropyran-4-yl)aminomethyl]aniline Dihydrochloride: A Kay Intermediate for TAK-779, a Small-Molecule Nonpeptide CCR5 Antagnoist", *Organic Process Research & Development*, 6(1), 70-73 (2002).
Wise, L. D. et al., "6- and 8-Hydroxy-3,4-dihydro-3-(dipropylamino)-2*H*-1-benzopyrans. Dopamine Agonists with Autoreceptor Selectivity" *Journal of Medical Chemistry*, 31(3), 688-691 (1988).
Tuallion N., et al., "MCP-1 Expression in Endotoxin-Induced Uveitis" *Investigative Opthalmology & Visual Science*, 43(5) 1493-1498 (2002).

* cited by examiner

*Primary Examiner*—Janet L. Andres
*Assistant Examiner*—Raymond Covington

(57) ABSTRACT

Quaternary salt compounds of Formula (I)

Formula (I)

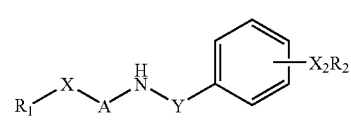

or pharmaceutically acceptable forms thereof, which are CCR2 antagonists and are useful in preventing, treating or ameliorating CCR2 mediated inflammatory syndromes, disorders or diseases in a subject in need thereof.

35 Claims, No Drawings

QUATERNARY SALT CCR2 ANTAGONISTS

This application claims the benefit of provisional application Ser. No. 60/582,929 filed on Jun. 24, 2004.

BACKGROUND OF THE INVENTION

The invention is directed to quaternary salt compounds which are antagonists to the chemoattractant cytokine receptor 2 (CCR2), pharmaceutical compositions, and methods for use thereof. More particularly, the CCR2 antagonists are phenylamino substituted quaternary salt compounds used in ameliorating or treating CCR2 mediated inflammatory disorders.

CCR2 is a member of the GPCR family of receptors, as are all known chemokine receptors and are expressed by monocytes and memory T-lymphocytes. The CCR2 signaling cascade involves activation of phospholipases (PLC$\beta_2$), protein kinases (PKC), and lipid kinases (PI-3 kinase).

Chemoattractant cytokines (i.e., chemokines) are relatively small proteins (8-10 kD) which stimulate the migration of cells. The chemokine family is divided into four subfamilies based on the number of amino acid residues between the first and second highly-conserved cysteines.

Monocyte chemotactic protein-1 (MCP-1) is a member of the CC chemokine subfamily (wherein CC represents the subfamily having adjacent first and second cysteines) and binds to the cell-surface chemokine receptor 2 (CCR2). MCP-1 is a potent chemotactic factor which, after binding to CCR2, mediates monocyte and lymphocyte migration (i.e., chemotaxis) toward a site of inflammation. MCP-1 is also expressed by cardiac muscle cells, blood vessel endothelial cells, fibroblasts, chondrocytes, smooth muscle cells, mesangial cells, alveolar cells, T-lymphocytes, marcophages, and the like.

After monocytes enter the inflammatory tissue and differentiate into macrophages, monocyte differentiation provides a secondary source of several proinflammatory modulators, including tumor necrosis factor-$\alpha$ (TNF-$\alpha$), interleukin-1 (IL-1), IL-8 (a member of the CXC chemokine subfamily, wherein CXC represents one amino acid residue between the first and second cysteines), IL-12, arachidonic acid metabolites (e.g., PGE$_2$ and LTB$_4$), oxygen-derived free radicals, matrix metalloproteinases and complement components.

Animal model studies of chronic inflammatory diseases have demonstrated that inhibition of binding between MCP-1 and CCR2 by an antagonist suppresses the inflammatory response. The interaction between MCP-1 and CCR2 has been implicated (see Rollins B J, Monocyte chemoattractant protein 1: a potential regulator of monocyte recruitment in inflammatory disease, *Mol. Med. Today*, 1996, 2:198; and Dawson J, et al., Targeting monocyte chemoattractant protein-1 signaling in disease, *Expert Opin. Ther. Targets*, 2003 February, 7(1):35-48) in inflammatory disease pathologies such as uveitis, atherosclerosis, rheumatoid arthritis, multiple sclerosis, Crohn's Disease, nephritis, organ allograft rejection, fibroid lung, renal insufficiency, diabetes and diabetic complications, diabetic nephropathy, diabetic retinopathy, diabetic retinitis, diabetic microangiopathy, tuberculosis, sarcoidosis, invasive staphylococcia, inflammation after cataract surgery, allergic rhinitis, allergic conjunctivitis, chronic urticaria, allergic asthma, periodontal diseases, periodontis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach.

Monocyte migration is inhibited by MCP-1 antagonists (either antibodies or soluble, inactive fragments of MCP-1) which have been shown to inhibit the development of arthritis, asthma, and uveitis. Both MCP-1 and CCR2 knockout (KO) mice have demonstrated that monocyte infiltration into inflammatory lesions is significantly decreased. In addition, such KO mice are resistant to the development of experimental allergic encephalomyelitis (EAE, a model of human MS), cockroach allergen-induced asthma, atherosclerosis, and uveitis. Rheumatoid arthritis and Crohn's Disease patients have improved during treatment with TNF-$\alpha$ antagonists (e.g., monoclonal antibodies and soluble receptors) at dose levels correlated with decreases in MCP-1 expression and the number of infiltrating macrophages.

MCP-1 has been implicated in the pathogenesis of seasonal and chronic allergic rhinitis, having been found in the nasal mucosa of most patients with dust mite allergies. MCP-1 has also been found to induce histamine release from basophils in vitro. During allergic conditions, both allergens and histamines have been shown to trigger (i.e., to up-regulate) the expression of MCP-1 and other chemokines in the nasal mucosa of people with allergic rhinitis, suggesting the presence of a positive feedback loop in such patients.

There remains a need for small molecule CCR2 antagonists for preventing, treating or ameliorating a CCR2 mediated inflammatory syndrome, disorder or disease resulting from MCP-1 induced monocyte and lymphocyte migration to a site of inflammation.

All documents cited herein are incorporated by reference.

SUMMARY OF THE INVENTION

The invention provides quaternary salt compounds of Formula (I)

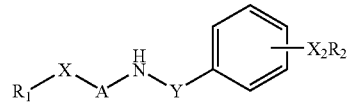

or pharmaceutically acceptable forms thereof, which are CCR2 antagonists and are useful in preventing, treating or ameliorating CCR2 mediated inflammatory syndromes, disorders or diseases in a subject in need thereof.

The present invention also provides a method for preventing, treating or ameliorating a CCR2 mediated inflammatory syndrome, disorder or disease in a subject in need thereof comprising administering to the subject an effective amount of a compound of Formula (I) or composition or medicament thereof.

DETAILED DESCRIPTION OF THE INVENTION

The present invention is directed to a compound of Formula (I)

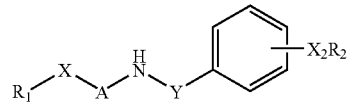

and pharmaceutically acceptable forms thereof, wherein

A is carbonyl, thiocarbonyl or sulfonyl;

X is a bond or —CH=CH—;

R$_1$ is selected from (1). aryl optionally substituted by one or more lower alkyl, —(CH$_2$)$_n$—CF$_3$, lower alkoxy, alkoxycarbonyl, cyano, halogen or phenyl optionally substituted by lower alkyl, —(CH$_2$)$_n$—CF$_3$, lower alkoxy, alkoxycarbonyl, cyano or halogen;

(2). $C_5$-$C_{15}$ cycloalkyl optionally substituted by one or more lower alkyl, —$(CH_2)_n$—$CF_3$, lower alkoxy, aryl, halogen-substituted aryl, alkoxycarbonyl, cyano or halogen; or, (3). heterocyclyl optionally substituted by one or more lower alkyl, —$(CH_2)_n$—$CF_3$, lower alkoxy, aryl, aryl-lower alkyl, halogen-substituted aryl, alkoxycarbonyl, cyano or halogen;

n is 0, 1, 2, 3 or 4;

Y is a bond or —$CH_2$—;

$X_2$ is —$(CH_2)_m$— wherein m is 1 or 2;

$R_2$ is —$N^+(R_4R_5)$—$ZR_3$;

Z is —$(CH_2)_p$— wherein p is 0, 1 or 2;

$R_3$ is selected from (1). aryl optionally substituted with one or more lower alkyl, —$(CH_2)_n$—$CF_3$, lower alkoxy, aryl, halogen-substituted aryl, alkoxycarbonyl, cyano or halogen;

(2). $C_5$-$C_{15}$ cycloalkyl optionally substituted with one or more lower alkyl, —$(CH_2)_n$—$CF_3$, lower alkoxy, aryl, halogen-substituted aryl, alkoxycarbonyl, cyano or halogen; or, (3). heterocyclyl optionally substituted with one or more lower alkyl, —$(CH_2)_n$—$CF_3$, lower alkoxy, aryl, halogen-substituted aryl, alkoxycarbonyl, cyano or halogen; wherein, when heterocyclyl is attached via a carbon atom ring member and a heteroatom ring member is adjacent to said carbon atom, then p is 1 or 2;

$R_4$ and $R_5$ are each individually lower alkyl or lower alkenyl; alternatively, $R_4$ and $R_5$ combine with the nitrogen atom of Formula (I) to form a heterocyclyl ring of 5 to 9 total ring atoms optionally containing one of an oxygen or sulfur ring atom, wherein the heterocyclyl ring nitrogen atom is substituted with one of lower alkyl or lower alkenyl to form a quaternary salt, and wherein —$ZR_3$ is absent and the heterocyclyl ring is optionally substituted with aryl optionally substituted with one or more lower alkyl, —$(CH_2)_n$—$CF_3$, lower alkoxy, aryl, halogen-substituted aryl, alkoxycarbonyl, cyano or halogen.

An example of the invention is a compound of Formula (I) and pharmaceutically acceptable forms thereof, wherein A is carbonyl; X is a bond; $R_1$ is selected from aryl substituted by one or more lower alkyl or halogen, $C_5$-$C_{15}$ cycloalkyl optionally substituted by one or more halogen, or heterocyclyl optionally substituted by one or more lower alkyl or halogen; Y is a bond; $X_2$ is —$CH_2$—; $R_2$ is —$N^+(R_4R_5)$—$R_3$; $R_3$ is selected from $C_5$-$C_{15}$ cycloalkyl or heterocyclyl and $R_4$ and $R_5$ are each individually lower alkyl.

An example of the invention is a compound of Formula (I) and pharmaceutically acceptable forms thereof, wherein A is carbonyl, X is a bond, $R_1$ is aryl optionally substituted by one or more halogen, Y is a bond, $X_2$ is —$CH_2$—, $R_2$ is —$N^+(R_4R_5)$—$R_3$, $R_3$ is heterocyclyl and $R_4$ and $R_5$ are each individually lower alkyl.

An example of the invention is a compound of Formula (I) and pharmaceutically acceptable forms thereof, wherein A is carbonyl.

An example of the invention is a compound of Formula (I) and pharmaceutically acceptable forms thereof, wherein $R_1$ is selected from (1). aryl optionally substituted by one or more lower-alkyl, —$(CH_2)_n$—$CF_3$, lower alkoxy, cyano, halogen or phenyl optionally substituted by lower alkyl, —$(CH_2)_n$—$CF_3$, lower alkoxy, cyano or halogen;

(2). $C_5$-$C_{15}$ cycloalkyl optionally substituted by one or more lower alkyl, —$(CH_2)_n$—$CF_3$, lower alkoxy, cyano or halogen; or, (3). heterocyclyl optionally substituted by one or more lower alkyl, —$(CH_2)_n$—$CF_3$, lower alkoxy, aryl, aryl-lower alkyl, halogen-substituted aryl or halogen.

An example of the invention is a compound of Formula (I) and pharmaceutically acceptable forms thereof, wherein n is 0.

An example of the invention is a compound of Formula (I) and pharmaceutically acceptable forms thereof, wherein p is 0 or 1.

An example of the invention is a compound of Formula (I) and pharmaceutically acceptable forms thereof, wherein $R_3$ is $C_5$-$C_{15}$ cycloalkyl or heterocyclyl; wherein, when heterocyclyl is attached via a carbon atom ring member and a heteroatom ring member is adjacent to said carbon atom, then p is 1.

An example of the invention is a compound of Formula (I) and pharmaceutically acceptable forms thereof, wherein $R_4$ and $R_5$ are each individually lower alkyl or lower allyl.

An example of the invention is a compound of Formula (I) and pharmaceutically acceptable forms thereof, wherein $R_4$ and $R_5$ combine with the nitrogen atom of Formula (I) to form a heterocyclyl ring of 5 to 9 total ring atoms optionally containing one of an oxygen or sulfur ring atom, wherein the heterocyclyl ring nitrogen atom is substituted with lower alkyl to form a quaternary salt, and wherein —$ZR_3$ is absent and the heterocyclyl ring is optionally substituted with aryl optionally substituted with one or more lower alkyl, —$(CH_2)_n$—$CF_3$, lower alkoxy, cyano or halogen.

An example of the invention is a compound of Formula (I) and pharmaceutically acceptable forms thereof, wherein $R_4$ and $R_5$ combine with the nitrogen atom of Formula (I) to form a heterocyclyl ring of 5 to 9 total ring atoms optionally containing one of an oxygen or sulfur ring atom, wherein the heterocyclyl ring nitrogen atom is substituted with lower alkyl to form a quaternary salt, and wherein —$ZR_3$ is absent and the heterocyclyl ring is optionally substituted with aryl optionally substituted with lower alkoxy.

An example of the invention is a compound of Formula (Ia)

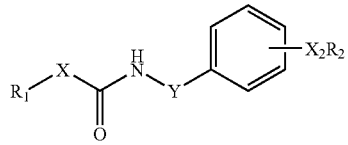

or pharmaceutically acceptable form thereof, wherein $R_1$, X, Y and $X_2R_2$ are dependently selected from

| Cpd | $R_1$ | X | Y | $X_2R_2$ |
| --- | --- | --- | --- | --- |
| 1 | 3-Br-phenyl | —CH=CH— | —$CH_2$— | 4-$CH_2$—$N^+(CH_3)_2$-cyclohexyl, |
| 2 | 3-Br-phenyl | bond | —$CH_2$— | 4-$CH_2$—$N^+(CH_3)_2$-cyclohexyl, |
| 3 | 3-$CF_3$-phenyl | bond | —$CH_2$— | 4-$CH_2$—$N^+(CH_3)_2$-cyclohexyl, |
| 4 | 3,4-$Cl_2$-phenyl | —CH=CH— | —$CH_2$— | 4-$CH_2$—$N^+(CH_3)_2$-tetrahydro-pyran-4-yl, |
| 5 | 3-Br-phenyl | —CH=CH— | —$CH_2$— | 4-$CH_2$—$N^+(CH_3)_2$-tetrahydro-pyran-4-yl, |
| 6 | phenyl | bond | bond | 4-$CH_2$—$N^+(CH_3)_2$-tetrahydro-pyran-4-yl, |
| 7 | 3,4-$Cl_2$-phenyl | bond | bond | 3-$CH_2$—$N^+(CH_3)_2$-tetrahydro-pyran-4-yl, |
| 8 | 3-Br-phenyl | bond | bond | 3-$CH_2$—$N^+(CH_3)_2$-tetrahydro-pyran-4-yl, |
| 9 | 2,3-$Cl_2$-phenyl | bond | bond | 4-$CH_2$—$N^+(CH_3)_2$-tetrahydro-pyran-4-yl, |
| 10 | 2,4-$Cl_2$-phenyl | bond | bond | 4-$CH_2$—$N^+(CH_3)_2$-tetrahydro-pyran-4-yl, |
| 11 | 2,5-$Cl_2$-phenyl | bond | bond | 4-$CH_2$—$N^+(CH_3)_2$-tetrahydro-pyran-4-yl, |

-continued

| Cpd | R$_1$ | X | Y | X$_2$R$_2$ |
|---|---|---|---|---|
| 12 | 2,6-Cl$_2$-phenyl | bond | bond | 4-CH$_2$—N$^+$(CH$_3$)$_2$-tetrahydro-pyran-4-yl, |
| 13 | 2-Cl-phenyl | bond | bond | 4-CH$_2$—N$^+$(CH$_3$)$_2$-tetrahydro-pyran-4-yl, |
| 14 | 3,4-Cl$_2$-phenyl | bond | bond | 4-CH$_2$—N$^+$(CH$_3$)$_2$-bicyclo[2.2.1]hept-2-yl, |
| 15 | 3,4-Cl$_2$-phenyl | bond | bond | 4-CH$_2$—N$^+$(CH$_3$)$_2$-(2S)-CH$_2$-tetrahydro-furan-2-yl, |
| 16 | 3,4-Cl$_2$-phenyl | bond | bond | 4-CH$_2$—N$^+$(CH$_3$)$_2$-(2R)-CH$_2$-tetrahydro-furan-2-yl, |
| 17 | 3,4-Cl$_2$-phenyl | bond | bond | 4-CH$_2$—N$^+$(CH$_3$)$_2$-tetrahydro-pyran-4-yl, |
| 18 | 3,4-Cl$_2$-phenyl | bond | bond | 4-CH$_2$—N$^+$(CH$_3$)$_2$-CH$_2$-tetrahydro-pyran-4-yl, |
| 19 | 3,4-Cl$_2$-phenyl | bond | bond | 4-CH$_2$—N$^+$(CH$_3$)$_2$-tetrahydro-thien-3-yl, |
| 20 | 3,4-Cl$_2$-phenyl | bond | bond | 4-CH$_2$—N$^+$(CH$_3$)$_2$-tetrahydro-thiopyran-4-yl, |
| 21 | 3,4-Cl$_2$-phenyl | bond | bond | 4-CH$_2$—N$^+$[(CH$_3$)(CH$_2$CH$_3$)]-tetrahydro-pyran-4-yl, |
| 22 | 3,4-Cl$_2$-phenyl | bond | bond | 4-CH$_2$—N$^+${(CH$_3$)[(CH$_2$)$_2$CH$_3$]}-tetrahydro-pyran-4-yl, |
| 23 | 3,5-Cl$_2$-phenyl | bond | bond | 4-CH$_2$—N$^+$(CH$_3$)$_2$-tetrahydro-pyran-4-yl, |
| 24 | 3-Br-phenyl | bond | bond | 4-CH$_2$—N$^+$(CH$_3$)$_2$-tetrahydro-pyran-4-yl, |
| 25 | 2-CH$_3$-3-Cl$_2$-phenyl | bond | bond | 4-CH$_2$—N$^+$(CH$_3$)$_2$-tetrahydro-pyran-4-yl, |
| 26 | 3-Cl-4-F-phenyl | bond | bond | 4-CH$_2$—N$^+$(CH$_3$)$_2$-tetrahydro-pyran-4-yl, |
| 27 | 3-Cl-4-OCH$_3$-phenyl | bond | bond | 4-CH$_2$—N$^+$(CH$_3$)$_2$-tetrahydro-pyran-4-yl, |
| 28 | 3-Cl-4-CH$_3$-phenyl | bond | bond | 4-CH$_2$—N$^+$(CH$_3$)$_2$-tetrahydro-pyran-4-yl, |
| 29 | 3-Cl-phenyl | bond | bond | 4-CH$_2$—N$^+$(CH$_3$)$_2$-tetrahydro-pyran-4-yl, |
| 30 | 3-CN-phenyl | bond | bond | 4-CH$_2$—N$^+$(CH$_3$)$_2$-tetrahydro-pyran-4-yl, |
| 31 | 3-OCH$_3$-phenyl | bond | bond | 4-CH$_2$—N$^+$(CH$_3$)$_2$-tetrahydro-pyran-4-yl, |
| 32 | 2-CH$_3$-4-Cl-phenyl | bond | bond | 4-CH$_2$—N$^+$(CH$_3$)$_2$-tetrahydro-pyran-4-yl, |
| 33 | 3-CF$_3$-4-Cl-phenyl | bond | bond | 4-CH$_2$—N$^+$(CH$_3$)$_2$-tetrahydro-pyran-4-yl, |
| 34 | 4-Cl-phenyl | bond | bond | 4-CH$_2$—N$^+$(CH$_3$)$_2$-tetrahydro-pyran-4-yl, |
| 35 | 2-CH$_3$-5-Cl-phenyl | bond | bond | 4-CH$_2$—N$^+$(CH$_3$)$_2$-tetrahydro-pyran-4-yl, |
| 36 | 3,4-Cl$_2$-phenyl | bond | bond | 4-(CH$_2$)$_2$—N$^+$(CH$_3$)$_2$-tetrahydro-pyran-4-yl, |
| 37 | 3-Br-phenyl | bond | bond | 4-(CH$_2$)$_2$—N$^+$(CH$_3$)$_2$-tetrahydro-pyran-4-yl, |
| 38 | 3-Br-phenyl | —CH=CH— | bond | 3-CH$_2$—N$^+$(CH$_3$)$_2$-tetrahydro-pyran-4-yl, |
| 39 | 3,4-Cl$_2$-phenyl | bond | —CH$_2$— | 4-CH$_2$—N$^+$(CH$_3$)$_2$-tetrahydro-pyran-4-yl, |
| 40 | 3,4-Cl$_2$-phenyl | —CH=CH— | bond | 4-CH$_2$—N$^+$(CH$_3$)$_2$-tetrahydro-pyran-4-yl, |
| 41 | 3,4-Cl$_2$-phenyl | —CH=CH— | bond | 4-CH$_2$—N$^+$(CH$_3$)$_2$-tetrahydro-thiopyran-4-yl, |
| 42 | 3,5-F$_2$-phenyl | —CH=CH— | bond | 4-CH$_2$—N$^+$(CH$_3$)$_2$-tetrahydro-pyran-4-yl, |
| 43 | 3-Br-phenyl | —CH=CH— | bond | 4-CH$_2$—N$^+$(CH$_3$)$_2$-tetrahydro-pyran-4-yl, |
| 44 | 3-Br-phenyl | —CH=CH— | bond | 4-CH$_2$—N$^+$(CH$_3$)$_2$-tetrahydro-thiopyran-4-yl, |
| 45 | 3-Cl-phenyl | —CH=CH— | bond | 4-CH$_2$—N$^+$(CH$_3$)$_2$-tetrahydro-pyran-4-yl, |
| 46 | 3-F-phenyl | —CH=CH— | bond | 4-CH$_2$—N$^+$(CH$_3$)$_2$-tetrahydro-pyran-4-yl, |
| 47 | 4-Br-phenyl | —CH=CH— | bond | 4-CH$_2$—N$^+$(CH$_3$)$_2$-tetrahydro-pyran-4-yl, |
| 48 | 3,4-Cl$_2$-phenyl | —CH=CH— | —CH$_2$— | 4-CH$_2$-(1-CH$_3$-piperidinium), |
| 49 | 3-Br-phenyl | —CH=CH— | —CH$_2$— | 4-CH$_2$-(1-CH$_3$-piperidinium), |
| 50 | 3,4-Cl$_2$-phenyl | bond | bond | 4-CH$_2$-(1-CH$_3$-piperidinium), |
| 51 | 3,4-Cl$_2$-phenyl | bond | bond | 4-CH$_2$-(1-CH$_3$-pyrrolidinium), |
| 52 | 3-Br-phenyl | —CH=CH— | bond | 3-CH$_2$-(1-CH$_3$-piperidinium), |
| 53 | 3,4-Cl$_2$-phenyl | —CH=CH— | bond | 4-CH$_2$-(1-CH$_3$-piperidinium), |
| 54 | 3,4-Cl$_2$-phenyl | —CH=CH— | bond | 4-CH$_2$-[4-(2-OCH$_3$-phenyl)-1-CH$_3$-piperazin-1-ium], |
| 55 | 3-Br-phenyl | —CH=CH— | bond | 4-CH$_2$-(1-CH$_3$-piperidinium), |
| 56 | 3-CF$_3$-phenyl | bond | bond | 3-CH$_2$-(1-CH$_3$-piperidinium), |
| 57 | 3-CF$_3$-phenyl | —CH=CH— | bond | 4-CH$_2$-(1-CH$_3$-piperidinium), |
| 58 | 3,4-Cl$_2$-phenyl | —CH=CH— | —CH$_2$— | 4-CH$_2$-(4-CH$_3$-morpholin-4-ium), |
| 59 | 3,4-Cl$_2$-phenyl | bond | bond | 4-CH$_2$-(4-CH$_3$-morpholin-4-ium), |
| 60 | 3,4-Cl$_2$-phenyl | —CH=CH— | bond | 4-CH$_2$-(4-CH$_3$-morpholin-4-ium), |
| 61 | 3-Br-phenyl | —CH=CH— | bond | 4-CH$_2$-(4-CH$_3$-morpholin-4-ium), |
| 62 | 3-CF$_3$-phenyl | —CH=CH— | —CH$_2$— | 4-CH$_2$-(4-CH$_3$-morpholin-4-ium), |
| 63 | 3-Br-phenyl | —CH=CH— | bond | 4-CH$_2$—N$^+$[(CH$_3$)(CH$_2$CH=CH$_2$)]-tetrahydro-thiopyran-4-yl, |
| 64 | 3-CF$_3$-phenyl | —CH=CH— | —CH$_2$— | 4-CH$_2$—N$^+$(CH$_3$)$_2$-tetrahydro-pyran-4-yl, |
| 65 | 3-CF$_3$-phenyl | bond | bond | 3-CH$_2$—N$^+$(CH$_3$)$_2$-tetrahydro-pyran-4-yl, |
| 66 | 3-CH$_3$-phenyl | —CH=CH— | bond | 4-CH$_2$—N$^+$(CH$_3$)$_2$-tetrahydro-pyran-4-yl, |
| 67 | 3-CF$_3$-phenyl | bond | bond | 4-CH$_2$—N$^+$(CH$_3$)$_2$-tetrahydro-pyran-4-yl, |
| 68 | 3-CF$_3$-phenyl | —CH=CH— | bond | 4-CH$_2$—N$^+$(CH$_3$)$_2$-tetrahydro-pyran-4-yl, |
| 69 | 3-CH$_3$-phenyl | bond | bond | 4-CH$_2$—N$^+$(CH$_3$)$_2$-tetrahydro-pyran-4-yl, |
| 70 | 3,4-Cl$_2$-phenyl | bond | bond | 4-CH$_2$—N$^+$(CH$_3$)$_2$-cycloheptyl, |
| 71 | 3,4-Cl$_2$-phenyl | —CH=CH— | bond | 4-CH$_2$—N$^+$(CH$_3$)$_2$-cyclohexyl, |
| 72 | 3-Br-phenyl | —CH=CH— | bond | 4-CH$_2$—N$^+$(CH$_3$)$_2$-cyclohexyl, |
| 73 | 3-Br-phenyl | bond | bond | 4-CH$_2$—N$^+$(CH$_3$)$_2$-cyclohexyl, |
| 74 | 3-CF$_3$-phenyl | bond | bond | 4-CH$_2$—N$^+$(CH$_3$)$_2$-cyclohexyl, |
| 75 | 3,4-Cl$_2$-phenyl | bond | bond | 4-CH$_2$—N$^+$(CH$_3$)$_2$-cyclohexyl, |
| 76 | 3-Cl-4-F-phenyl | bond | bond | 4-CH$_2$—N$^+$(CH$_3$)$_2$-cyclohexyl, |

-continued

| Cpd | R₁ | X | Y | X₂R₂ |
|---|---|---|---|---|
| 77 | 2,3-Cl₂-phenyl | bond | bond | 4-CH₂—N⁺(CH₃)₂-cyclohexyl, |
| 78 | 2,6-Cl₂-phenyl | bond | bond | 4-CH₂—N⁺(CH₃)₂-cyclohexyl, |
| 79 | 3-Cl-4-OCH₃-phenyl | bond | bond | 4-CH₂—N⁺(CH₃)₂-cyclohexyl, |
| 80 | 3-Cl-4-CH₃-phenyl | bond | bond | 4-CH₂—N⁺(CH₃)₂-cyclohexyl, |
| 81 | 2,5-Cl₂-phenyl | bond | bond | 4-CH₂—N⁺(CH₃)₂-cyclohexyl, |
| 82 | 3,4-Cl₂-phenyl | bond | bond | 4-CH₂—N⁺(CH₃)₂-cyclopentyl, |
| 83 | 3,4-Cl₂-phenyl | —CH=CH— | bond | 3-CH₂—N⁺(CH₃)₂-cyclohexyl, |
| 84 | 4-F-phenyl | —CH=CH— | bond | 3-CH₂—N⁺(CH₃)₂-cyclohexyl, |
| 85 | 3-(4-CF₃-phenyl)-phenyl | bond | bond | 4-CH₂—N⁺(CH₃)₂-tetrahydro-pyran-4-yl, |
| 86 | 3-(4-CH₃-phenyl)-phenyl | bond | bond | 4-CH₂—N⁺(CH₃)₂-cyclohexyl, |
| 87 | 3-(4-CH₃-phenyl)-phenyl | bond | bond | 4-CH₂—N⁺(CH₃)₂-tetrahydro-pyran-4-yl, |
| 88 | 4-biphenyl | bond | bond | 4-CH₂—N⁺(CH₃)₂-tetrahydro-pyran-4-yl, |
| 89 | 1-naphthalene | bond | bond | 4-CH₂—N⁺(CH₃)₂-tetrahydro-pyran-4-yl, |
| 90 | 2-naphthalene | bond | bond | 4-CH₂—N⁺(CH₃)₂-tetrahydro-pyran-4-yl, |
| 91 | 2-naphthalene | bond | bond | 4-CH₂—N⁺[(CH₃)(CH₂CH₃)]-tetrahydro-pyran-4-yl, |
| 92 | 2-naphthalene | bond | bond | 4-CH₂—N⁺{(CH₃)[(CH₂)₂CH₃]}-tetrahydro-pyran-4-yl, |
| 93 | 7-Br-naphthalen-2-yl | bond | bond | 4-CH₂—N⁺(CH₃)₂-tetrahydro-pyran-4-yl, |
| 94 | 7-Br-naphthalen-2-yl | bond | bond | 4-CH₂—N⁺(CH₃)₂-cyclohexyl, |
| 95 | 6-Br-2H-chromen-3-yl | bond | bond | 4-CH₂—N⁺(CH₃)₂-tetrahydro-pyran-4-yl, |
| 96 | 6-Cl-2H-chromen-3-yl | bond | bond | 4-CH₂—N⁺(CH₃)₂-tetrahydro-pyran-4-yl, |
| 97 | 6-Br-2H-chromen-3-yl | bond | bond | 4-CH₂—N⁺(CH₃)₂-cyclohexyl, |
| 98 | 6-Cl-2H-chromen-3-yl | bond | bond | 4-CH₂—N⁺(CH₃)₂-cyclohexyl, |
| 99 | 6-Br-2H-chromen-3-yl | bond | —CH₂— | 4-CH₂—N⁺(CH₃)₂-tetrahydro-pyran-4-yl, |
| 100 | 5,7-Cl₂-2H-chromen-3-yl | bond | bond | 4-CH₂—N⁺(CH₃)₂-tetrahydro-pyran-4-yl, |
| 101 | 5,7-Cl₂-2H-chromen-3-yl | bond | bond | 4-CH₂—N⁺(CH₃)₂-cyclohexyl, |
| 102 | 6,8-Cl₂-2H-chromen-3-yl | bond | bond | 4-CH₂—N⁺(CH₃)₂-tetrahydro-pyran-4-yl, |
| 103 | 6-CH₃-2H-chromen-3-yl | bond | bond | 4-CH₂—N⁺(CH₃)₂-tetrahydro-pyran-4-yl, |
| 104 | 6-OCH₃-2H-chromen-3-yl | bond | bond | 4-CH₂—N⁺(CH₃)₂-tetrahydro-pyran-4-yl, |
| 105 | 6-CH₃-2H-chromen-3-yl | bond | bond | 4-CH₂—N⁺(CH₃)₂-cyclohexyl, |
| 106 | 6-OCH₃-2H-chromen-3-yl | bond | bond | 4-CH₂—N⁺(CH₃)₂-cyclohexyl, |
| 107 | 6,8-Cl₂-2H-chromen-3-yl | bond | bond | 4-CH₂—N⁺(CH₃)₂-cyclohexyl, |
| 108 | 6-Cl-2H-chromen-3-yl | bond | bond | 4-CH₂—N⁺(CH₃)₂-(2R)-CH₂-tetrahydro-furan-2-yl, |
| 109 | 6-Cl-2H-chromen-3-yl | bond | bond | 4-CH₂—N⁺(CH₃)₂-(2S)-CH₂-tetrahydro-furan-2-yl, |
| 110 | 6-Cl-2H-chromen-3-yl | bond | bond | 4-CH₂—N⁺(CH₃)₂-(2S)-bicyclo[2.2.1]hept-2-yl, |
| 111 | 6,8-Cl₂-2H-chromen-3-yl | bond | bond | 4-CH₂—N⁺(CH₃)₂-bicyclo[2.2.1]hept-2-yl, |
| 112 | 8-CH₃-2H-chromen-3-yl | bond | bond | 4-CH₂—N⁺(CH₃)₂-tetrahydro-pyran-4-yl, |
| 113 | 8-CH₃-2H-chromen-3-yl | bond | bond | 4-CH₂—N⁺(CH₃)₂-cyclohexyl, |
| 114 | 6-Cl-8-CH₃-2H-chromen-3-yl | bond | bond | 4-CH₂—N⁺(CH₃)₂-cyclohexyl, |
| 115 | 6-Cl-8-CH₃-2H-chromen-3-yl | bond | bond | 4-CH₂—N⁺(CH₃)₂-tetrahydro-pyran-4-yl, |
| 116 | 7,8-Cl₂-2H-chromen-3-yl | bond | bond | 4-CH₂—N⁺(CH₃)₂-cyclohexyl, |
| 117 | 6-Cl-8-CH₃-2H-chromen-3-yl | bond | bond | 4-CH₂—N⁺(CH₃)₂-bicyclo[2.2.1]hept-2-yl, |
| 118 | 6-Cl-8-CH₃-2H-chromen-3-yl | bond | bond | 4-CH₂—N⁺(CH₃)₂-cycloheptyl, |
| 119 | 6-Cl-8-CH₃-2H-chromen-3-yl | bond | bond | 4-CH₂—N⁺(CH₃)₂-cyclopentyl, |
| 120 | 6-Cl-8-CH₃-2H-chromen-3-yl | bond | bond | 4-CH₂—N⁺(CH₃)₂-thien-3-yl, |

-continued

| Cpd | R₁ | X | Y | X₂R₂ |
|---|---|---|---|---|
| 121 | 6-Cl-8-CH₃-2H-chromen-3-yl | bond | —CH₂— | 4-CH₂—N⁺(CH₃)₂-tetrahydro-pyran-4-yl, |
| 122 | 6,8-Cl₂-2H-chromen-3-yl | bond | bond | 4-CH₂—N⁺(CH₃)₂-thien-3-yl, |
| 123 | 6-F-2H-chromen-3-yl | bond | bond | 4-CH₂—N⁺(CH₃)₂-cyclohexyl, |
| 124 | 5-F-2H-chromen-3-yl | bond | bond | 4-CH₂—N⁺(CH₃)₂-cyclohexyl, |
| 125 | 6-CF₃-2H-chromen-3-yl | bond | bond | 4-CH₂—N⁺(CH₃)₂-cyclohexyl, |
| 126 | 8-F-2H-chromen-3-yl | bond | bond | 4-CH₂—N⁺(CH₃)₂-cyclohexyl, |
| 127 | 7-CH₃-2H-chromen-3-yl | bond | bond | 4-CH₂—N⁺(CH₃)₂-cyclohexyl, |
| 128 | 7-OCH₃-2H-chromen-3-yl | bond | bond | 4-CH₂—N⁺(CH₃)₂-cyclohexyl, |
| 129 | 6-OCH₃-2H-chromen-3-yl | bond | bond | 4-CH₂—N⁺(CH₃)₂-cyclohexyl, |
| 130 | 6-CF₃-2H-chromen-3-yl | bond | bond | 4-CH₂—N⁺(CH₃)₂-thien-3-yl, |
| 131 | 4-F-2H-chromen-3-yl | bond | bond | 4-CH₂—N⁺(CH₃)₂-thien-3-yl, |
| 132 | 5-F-2H-chromen-3-yl | bond | bond | 4-CH₂—N⁺(CH₃)₂-thien-3-yl, |
| 133 | 4-CF₃-2H-chromen-3-yl | bond | bond | 4-CH₂—N⁺(CH₃)₂-cyclohexyl, |
| 134 | 8-CF₃-2H-chromen-3-yl | bond | bond | 4-CH₂—N⁺(CH₃)₂-cyclohexyl, |
| 135 | 3H-benzo[f]chromen-2-yl | bond | bond | 4-CH₂—N⁺(CH₃)₂-tetrahydro-pyran-4-yl, |
| 136 | 3H-benzo[f]chromen-2-yl | bond | bond | 4-CH₂-(1-CH₃-pyrrolidinium), |
| 137 | 3H-benzo[f]chromen-2-yl | bond | bond | 4-CH₂—N⁺(CH₃)₂-cyclohexyl, |
| 138 | 3H-benzo[f]chromen-2-yl | bond | bond | 4-CH₂—N⁺(CH₃)₂-tetrahydro-thiopyran-4-yl, |
| 139 | 3H-benzo[f]chromen-2-yl | bond | bond | 4-CH₂-(4-CH₃-morpholin-4-ium), |
| 140 | 3H-benzo[f]chromen-2-yl | bond | bond | 4-CH₂—N⁺(CH₃)₂-CH₂-tetrahydro-pyran-4-yl, |
| 141 | 3H-benzo[f]chromen-2-yl | bond | —CH₂— | 4-CH₂—N⁺(CH₃)₂-tetrahydro-pyran-4-yl, |
| 142 | 3-Br-8,9-dihydro-7H-benzocyclohepten-6-yl | bond | —CH₂— | 4-CH₂—N⁺(CH₃)₂-tetrahydro-pyran-4-yl, |
| 143 | 3-Br-8,9-dihydro-7H-benzocyclohepten-6-yl | bond | bond | 4-CH₂—N⁺(CH₃)₂-tetrahydro-pyran-4-yl, |
| 144 | 3-Br-8,9-dihydro-7H-benzocyclohepten-6-yl | bond | bond | 4-CH₂—N⁺(CH₃)₂-cyclohexyl, |
| 145 | 8,9-dihydro-7H-benzocyclohepten-6-yl | bond | bond | 4-CH₂—(1-CH₃-pyrrolidinium), |
| 146 | 8,9-dihydro-7H-benzocyclohepten-6-yl | bond | bond | 4-CH₂—N⁺(CH₃)₂-cyclohexyl, |
| 147 | 8,9-dihydro-7H-benzocyclohepten-6-yl | bond | bond | 4-CH₂—N⁺(CH₃)₂-tetrahydro-pyran-4-yl, |
| 148 | 8,9-dihydro-7H-benzocyclohepten-6-yl | bond | —CH₂— | 4-CH₂—N⁺(CH₃)₂-tetrahydro-pyran-4-yl, |
| 149 | (2-CH₃-5-phenyl)-furan-3-yl | bond | —CH₂— | 4-CH₂—N⁺(CH₃)₂-tetrahydro-pyran-4-yl, |
| 150 | [5-(4-Cl-phenyl)-2-CH₃]-furan-3-yl | bond | —CH₂— | 4-CH₂—N⁺(CH₃)₂-tetrahydro-pyran-4-yl, |
| 151 | (2-CH₃-5-phenyl)-furan-3-yl | bond | bond | 4-CH₂—N⁺(CH₃)₂-cyclohexyl, |

-continued

| Cpd | R₁ | X | Y | X₂R₂ |
|---|---|---|---|---|
| 152 | benzofuran-2-yl | bond | bond | 4-CH₂—N⁺(CH₃)₂-tetrahydro-pyran-4-yl, |
| 153 | [5-(4-Cl-phenyl)-2-CF₃]-furan-3-yl | bond | —CH₂— | 4-CH₂—N⁺(CH₃)₂-tetrahydro-pyran-4-yl, |
| 154 | [5-(4-Cl-phenyl)-2-CF₃]-furan-3-yl | bond | —CH₂— | 4-CH₂—N⁺(CH₃)₂-cyclohexyl, |
| 155 | 5-Cl-benzofuran-2-yl | bond | bond | 4-CH₂—N⁺(CH₃)₂-tetrahydro-pyran-4-yl, |
| 156 | 5-Cl-benzofuran-2-yl | bond | bond | 4-CH₂—N⁺(CH₃)₂-cyclohexyl, |
| 157 | benzofuran-2-yl | bond | bond | 4-CH₂—N⁺(CH₃)₂-cyclohexyl, |
| 158 | 1-CH₃-1H-indol-2-yl | bond | bond | 4-CH₂—N⁺(CH₃)₂-tetrahydro-pyran-4-yl, |
| 159 | 5-Cl-1H-indol-2-yl | bond | bond | 4-CH₂—N⁺(CH₃)₂-tetrahydro-pyran-4-yl, |
| 160 | 5-Br-1H-indol-2-yl | bond | bond | 4-CH₂—N⁺(CH₃)₂-tetrahydro-pyran-4-yl, |
| 161 | 1-CH₃-1H-indol-3-yl | bond | bond | 4-CH₂—N⁺(CH₃)₂-tetrahydro-pyran-4-yl, |
| 162 | (1-CH₂-phenyl)-1H-indol-3-yl | bond | bond | 4-CH₂—N⁺(CH₃)₂-tetrahydro-pyran-4-yl, |
| 163 | 1-CH₃-1H-indol-2-yl | bond | bond | 4-CH₂—N⁺(CH₃)₂-tetrahydro-pyran-4-yl, |
| 164 | 5-Cl-1H-indol-2-yl | bond | bond | 4-CH₂—N⁺(CH₃)₂-cyclohexyl, |
| 165 | 5-Cl-1H-indol-2-yl | bond | bond | 4-CH₂—N⁺(CH₃)₂-(2S)-CH₂-tetrahydro-furan-2-yl, |
| 166 | 5-Cl-1H-indol-2-yl | bond | bond | 4-CH₂—N⁺(CH₃)₂—CH₂—bicyclo[2.2.1]hept-2-yl, |
| 167 | 7,8-Cl₂-2,3-dihydro-benzo[b]oxepin-4-yl | bond | bond | 4-CH₂—N⁺(CH₃)₂-tetrahydro-pyran-4-yl, |
| 168 | 7,8-Cl₂-2,3-dihydro-benzo[b]oxepin-4-yl | bond | bond | 4-CH₂—N⁺(CH₃)₂-cyclohexyl, |
| 169 | 7,8-Cl₂-2,3-dihydro-benzo[b]oxepin-4-yl | bond | bond | 4-CH₂—N⁺(CH₃)₂-bicyclo[2.2.1]hept-2-yl, |
| 170 | 7,8-Cl₂-2,3-dihydro-benzo[b]oxepin-4-yl | bond | —CH₂— | 4-CH₂—N⁺(CH₃)₂-tetrahydro-pyran-4-yl, |
| 171 | 7,8-Cl₂-2,3-dihydro-benzo[b]oxepin-4-yl | bond | bond | 4-CH₂—N⁺(CH₃)₂-thien-3-yl, |
| 172 | 5-Br-pyridin-3-yl | bond | bond | 4-CH₂—N⁺(CH₃)₂-tetrahydro-pyran-4-yl, |
| 173 | 2-Cl-pyridin-4-yl | bond | bond | 4-CH₂—N⁺(CH₃)₂-tetrahydro-pyran-4-yl, |
| 174 | 3-Cl-benzo[b]thien-2-yl | bond | bond | 4-CH₂—N⁺(CH₃)₂-tetrahydro-pyran-4-yl, |
| 175 | 2,5-Cl₂-thien-3-yl | bond | bond | 4-CH₂—N⁺(CH₃)₂-tetrahydro-pyran-4-yl, |
| 176 | benzo[b]thien-2-yl | bond | bond | 4-CH₂—N⁺(CH₃)₂-tetrahydro-pyran-4-yl, |
| 177 | benzo[b]thien-2-yl | bond | bond | 4-CH₂—N⁺(CH₃)₂-cyclohexyl, |
| 178 | 3-Cl-benzo[b]thien-2-yl | bond | bond | 4-CH₂—N⁺(CH₃)₂-cyclohexyl, |

An example of the invention is a compound of Formula (I) and pharmaceutically acceptable forms thereof represented as follows:

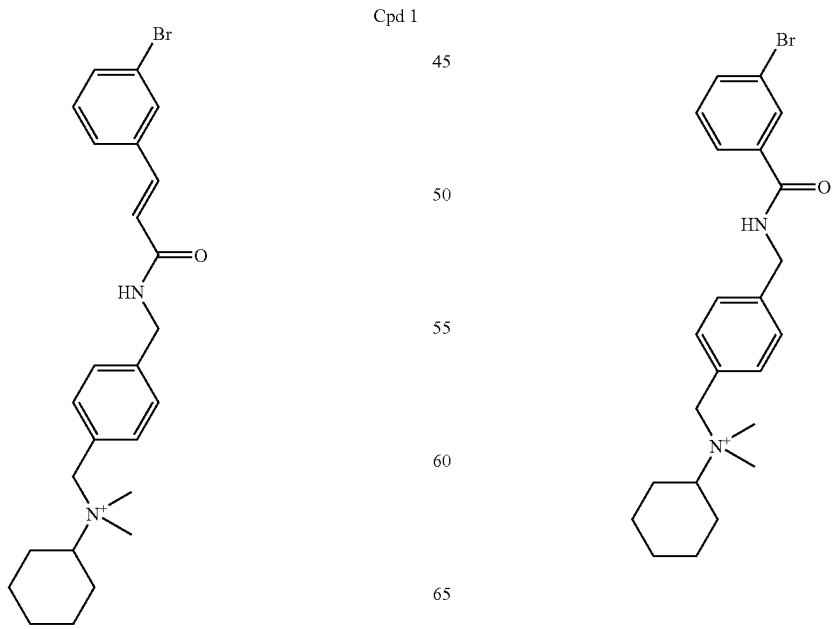

-continued
Cpd 3
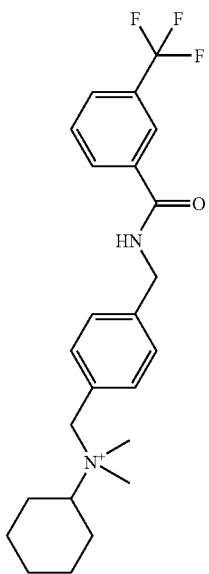
Cpd 4
Cpd 5
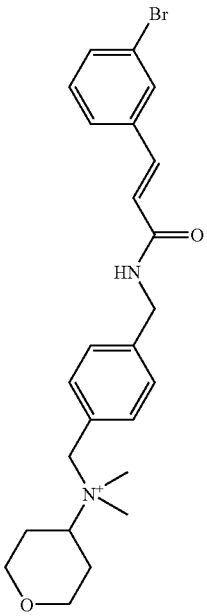
Cpd 6
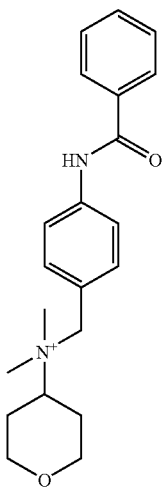
Cpd 7
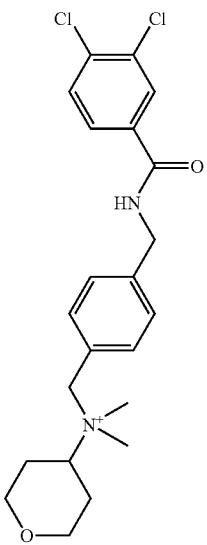

-continued

Cpd 8

Cpd 9

Cpd 10

-continued

Cpd 11

Cpd 12

Cpd 13

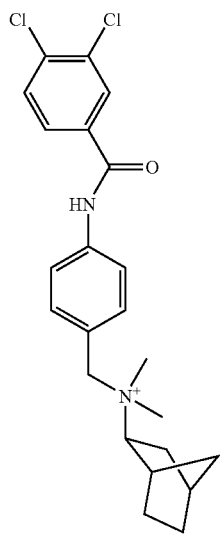
Cpd 14
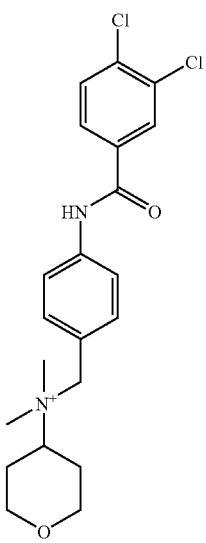
Cpd 17
Cpd 15
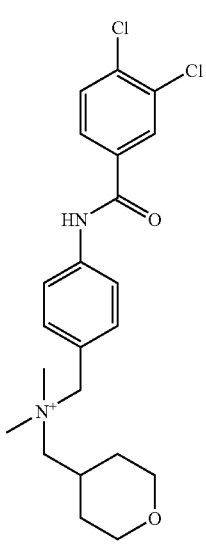
Cpd 18
Cpd 16
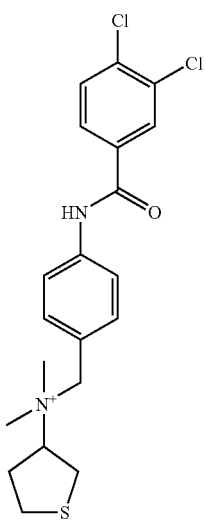
Cpd 19

-continued
Cpd 20
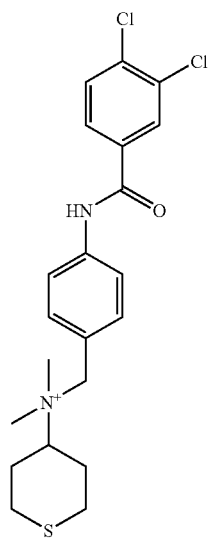
Cpd 21
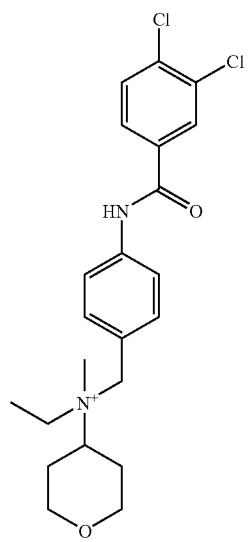
Cpd 22
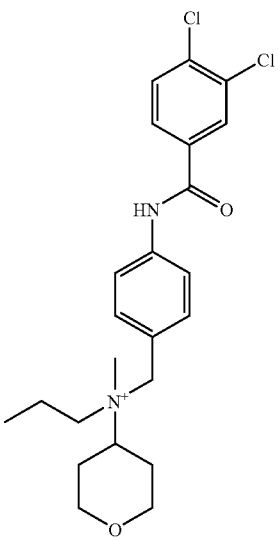
-continued
Cpd 23
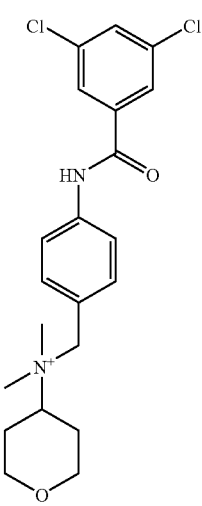
Cpd 24
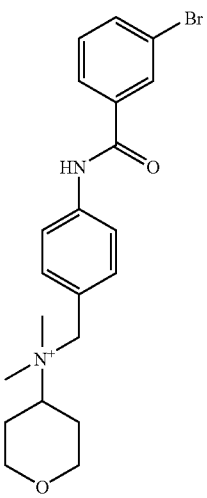
Cpd 25
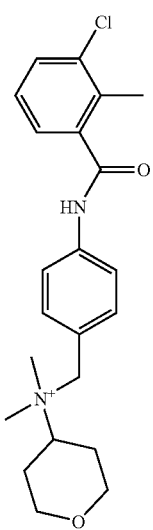

-continued
Cpd 26
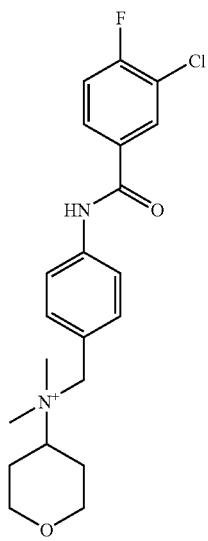
Cpd 27
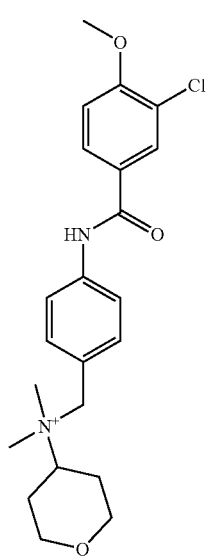
Cpd 28
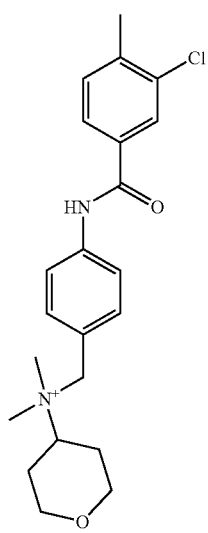
-continued
Cpd 29
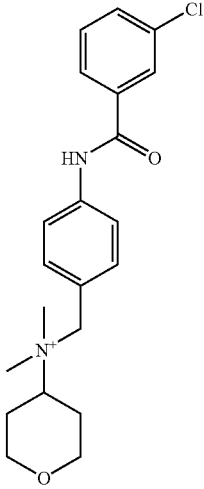
Cpd 30
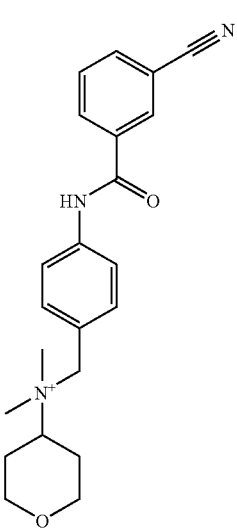
Cpd 31
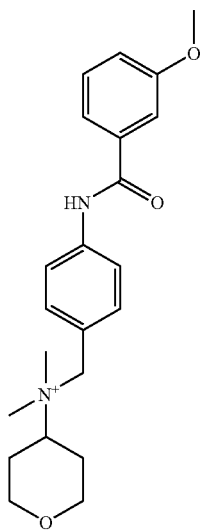

-continued
Cpd 32
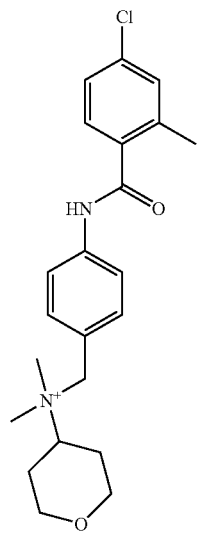
Cpd 33
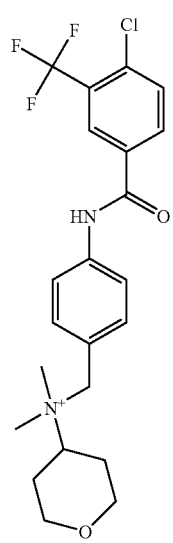
Cpd 34
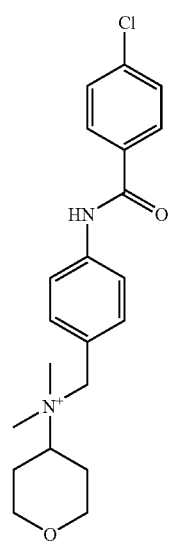
-continued
Cpd 35
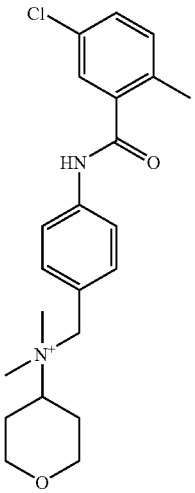
Cpd 36
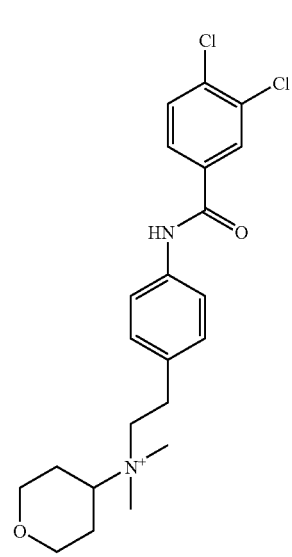
Cpd 37
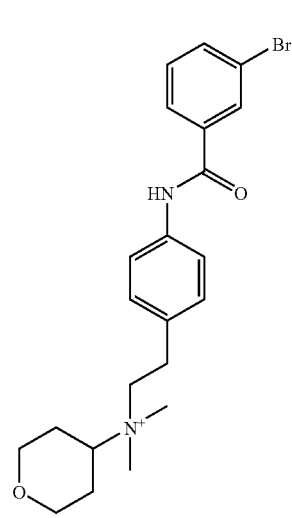

Cpd 38
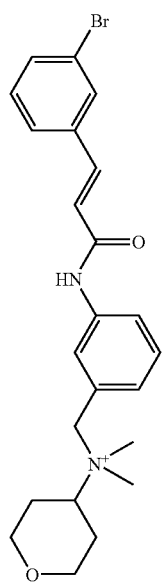
Cpd 40
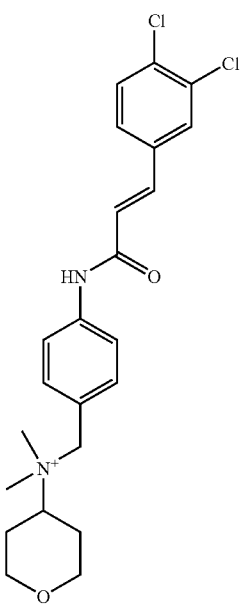
Cpd 39
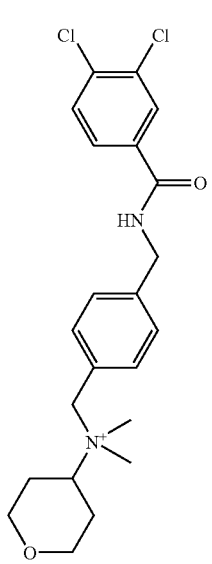
Cpd 41
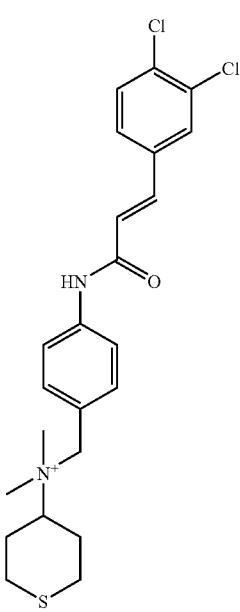

-continued
Cpd 42
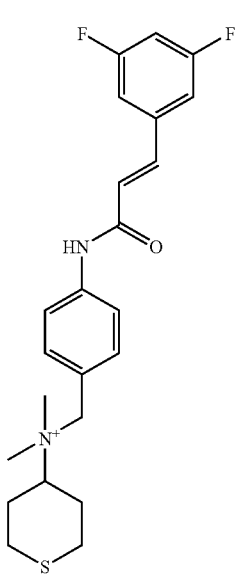
Cpd 44
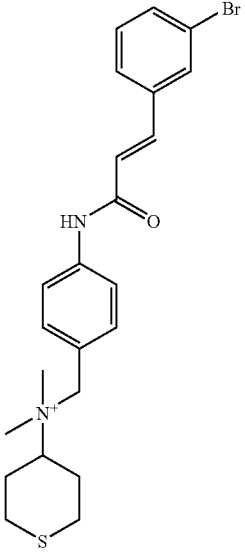
Cpd 43
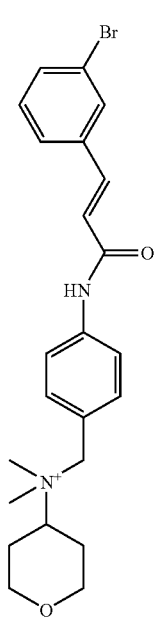
Cpd 45
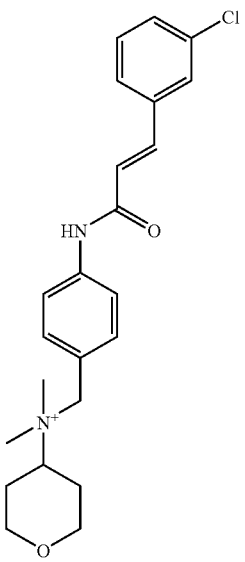

-continued

Cpd 46

Cpd 47

Cpd 48

Cpd 49

Cpd 50

-continued
Cpd 51
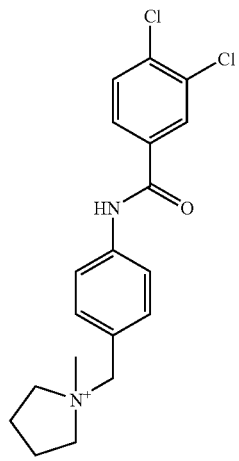
Cpd 52
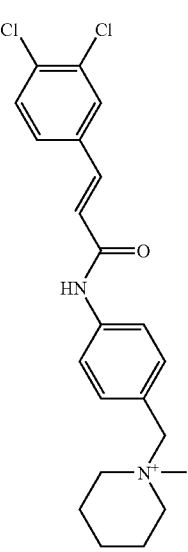
Cpd 53
-continued
Cpd 54
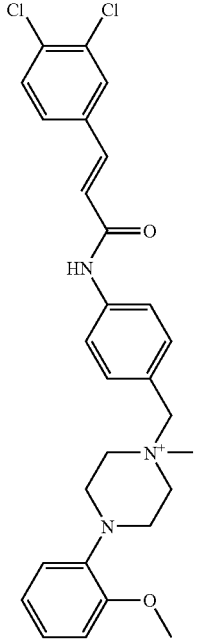
Cpd 55
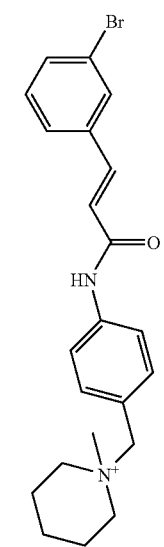

Cpd 56
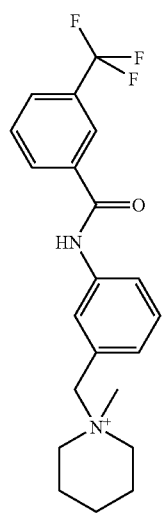
Cpd 57
Cpd 58
Cpd 59
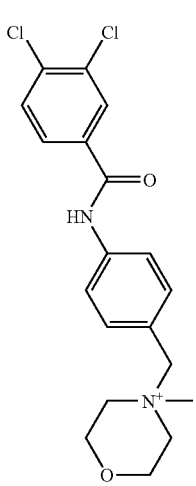
Cpd 60
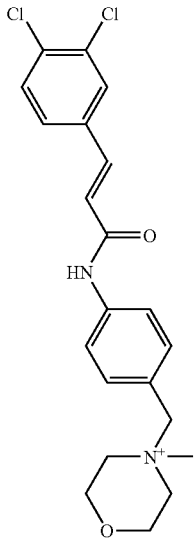
Cpd 61
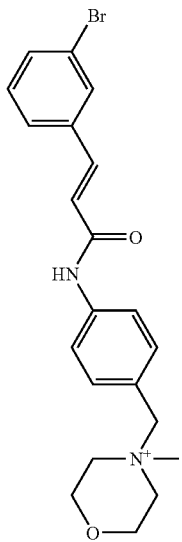

Cpd 62
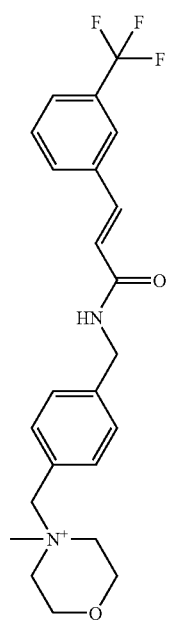
Cpd 63
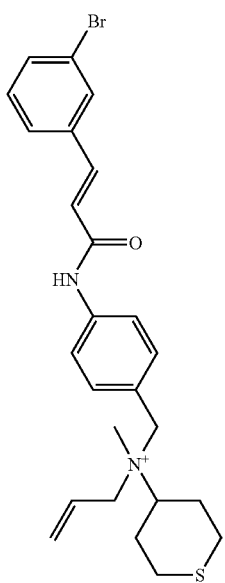
Cpd 64
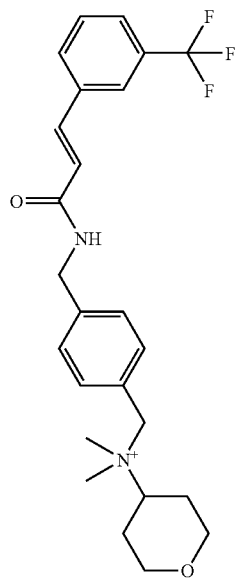
Cpd 65
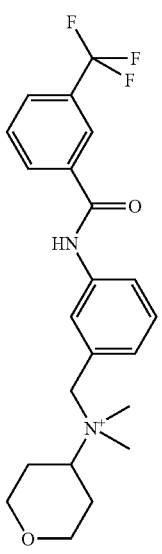

-continued
Cpd 66
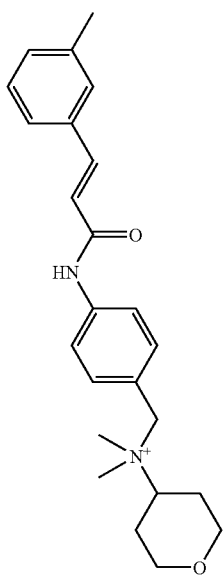
Cpd 67
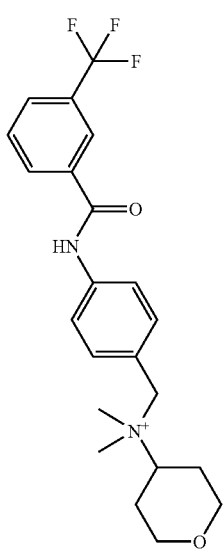
-continued
Cpd 68
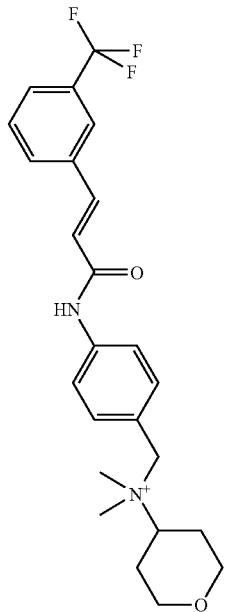
Cpd 69
Cpd 70
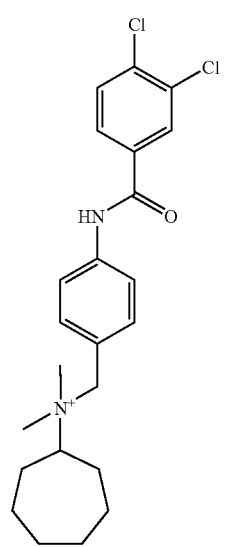

-continued
Cpd 71
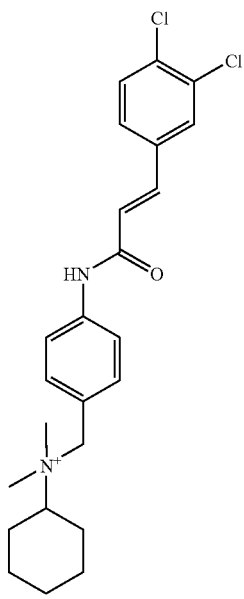
Cpd 72
Cpd 73
-continued
Cpd 74
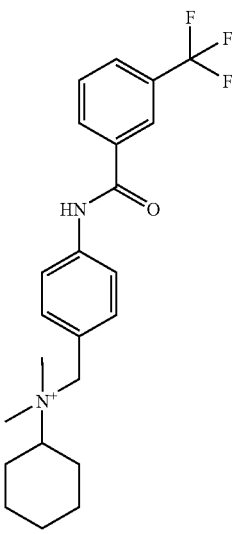
Cpd 75
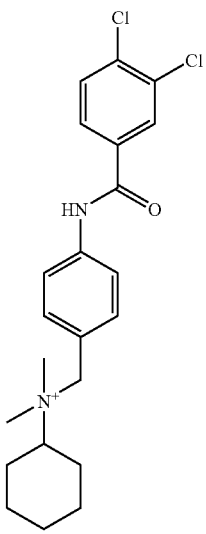
Cpd 76
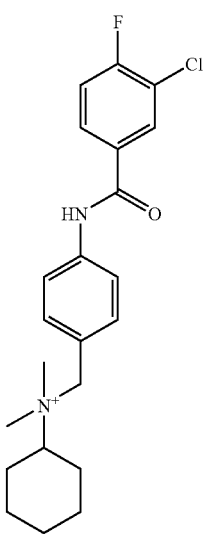

-continued
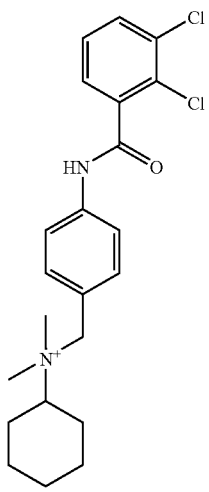
Cpd 77
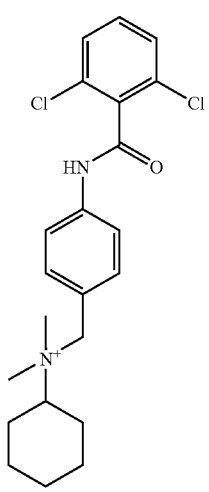
Cpd 78
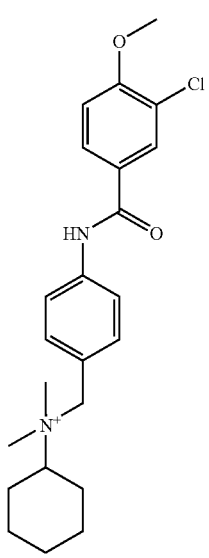
Cpd 79
-continued
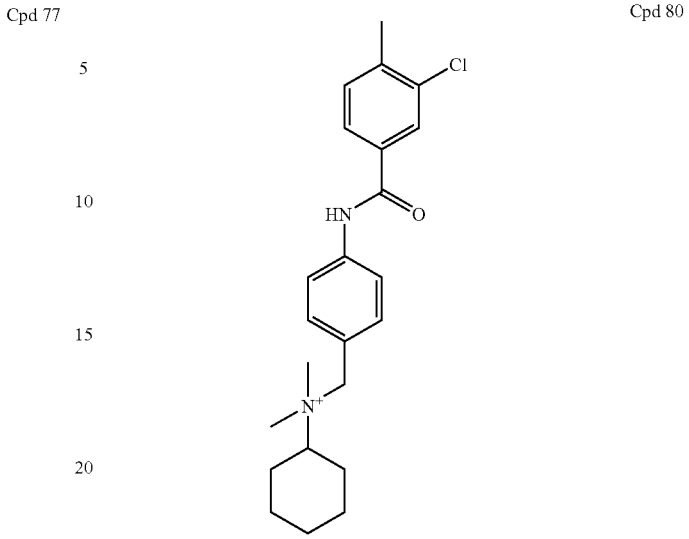
Cpd 80
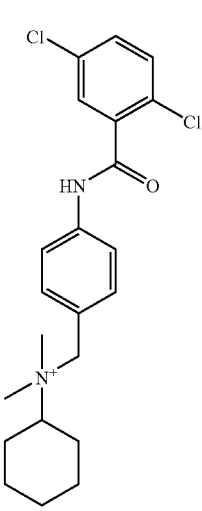
Cpd 81
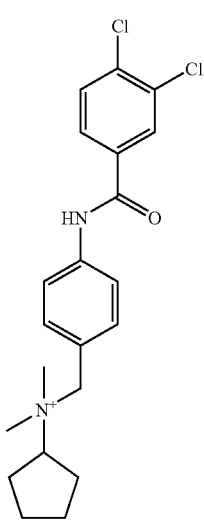
Cpd 82

-continued
Cpd 83
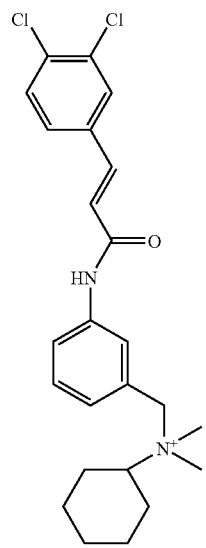
Cpd 84
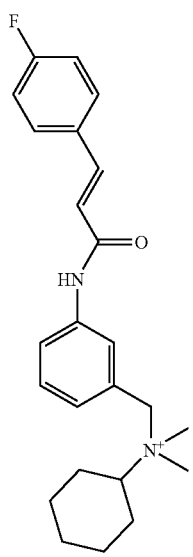
-continued
Cpd 85
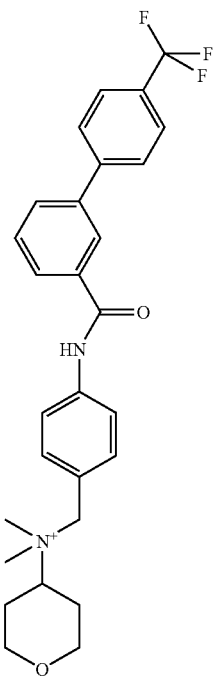
Cpd 86
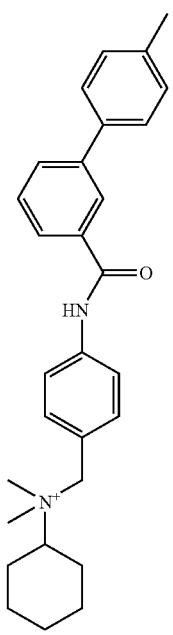

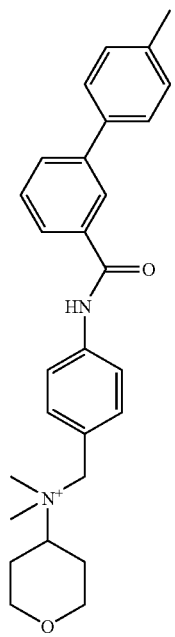
Cpd 87
Cpd 88
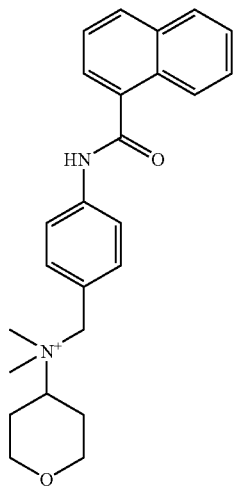
Cpd 89
Cpd 90
Cpd 91

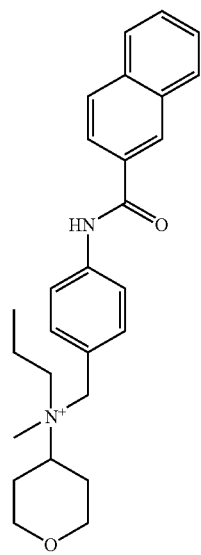
Cpd 92
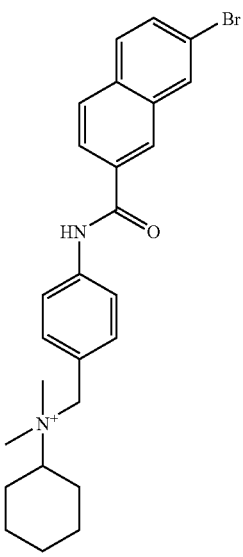
Cpd 94
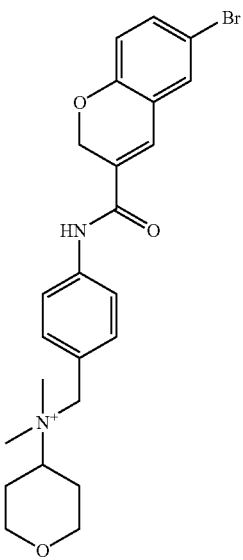
Cpd 95
Cpd 93

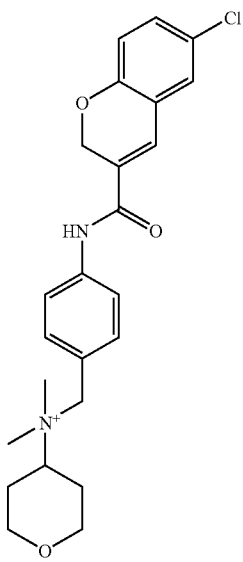 Cpd 96
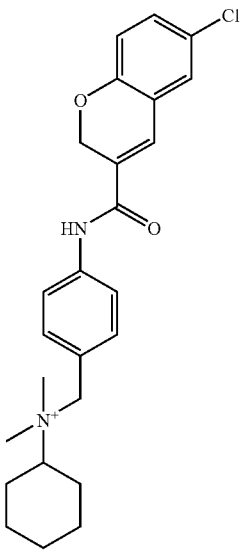 Cpd 98
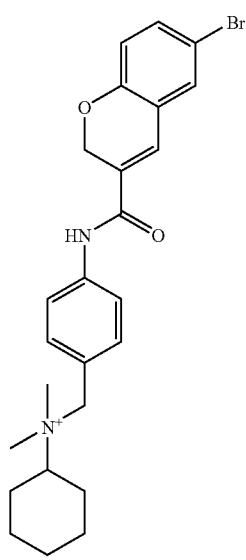 Cpd 97
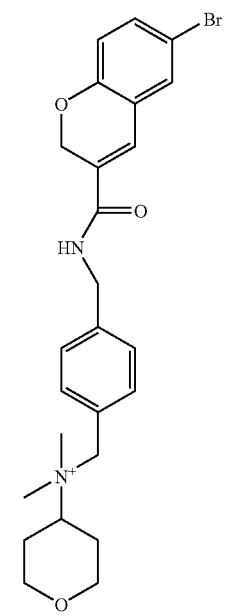 Cpd 99

-continued
Cpd 100
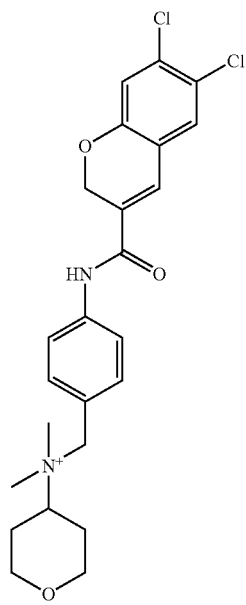
Cpd 102
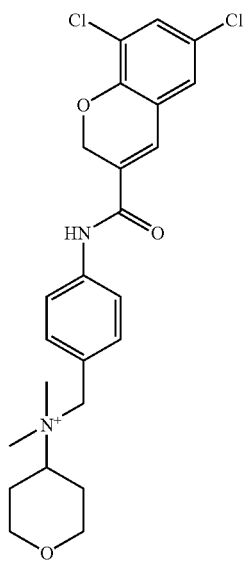
Cpd 101
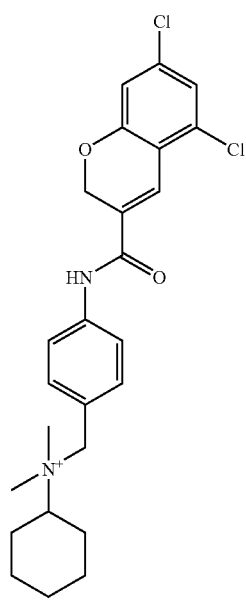
Cpd 103
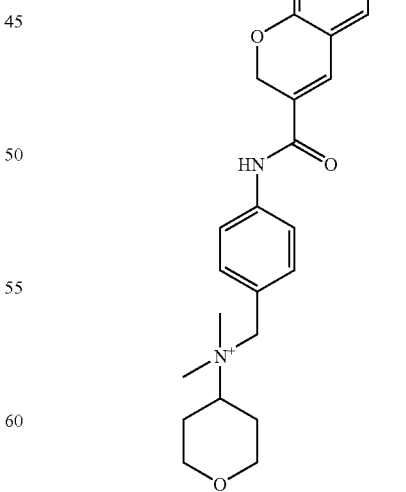

Cpd 104
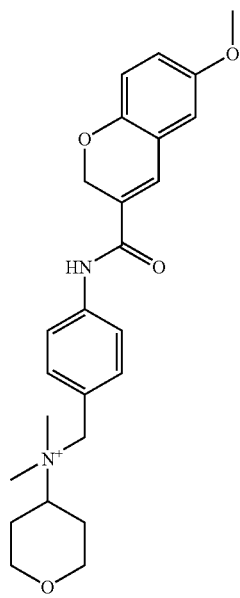
Cpd 105
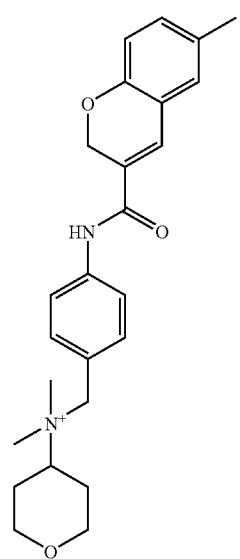
Cpd 106
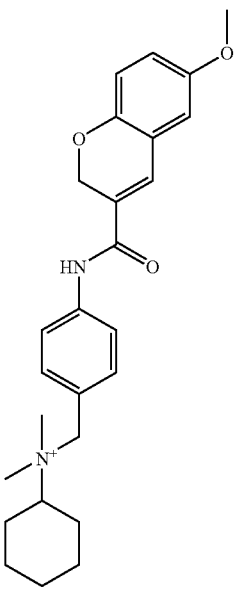
Cpd 107

-continued
Cpd 108
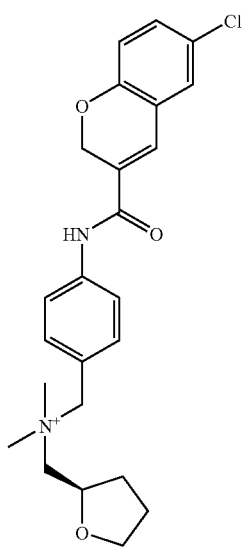
Cpd 109
Cpd 110
-continued
Cpd 111
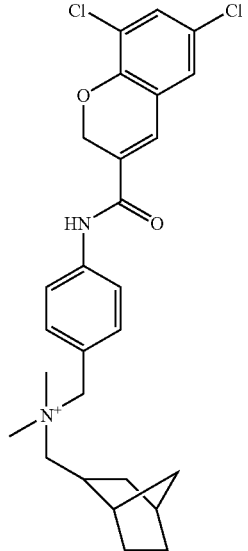
Cpd 112
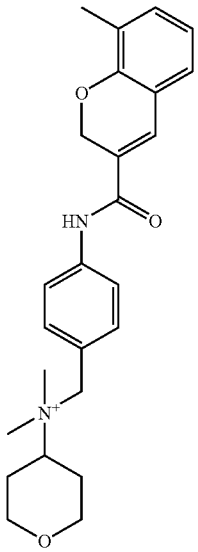
Cpd 113
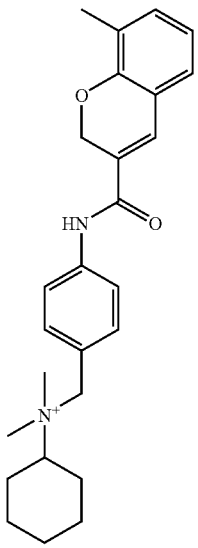

-continued
Cpd 114
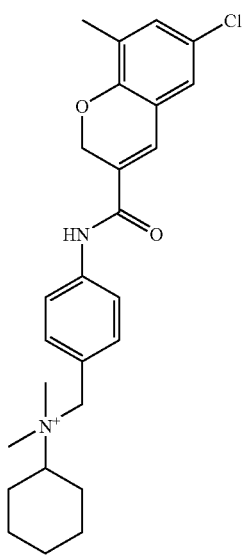
Cpd 115
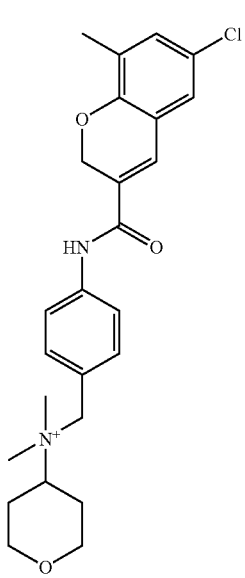
-continued
Cpd 116
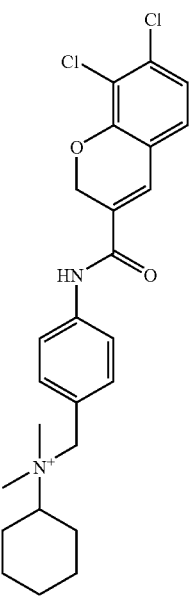
Cpd 117

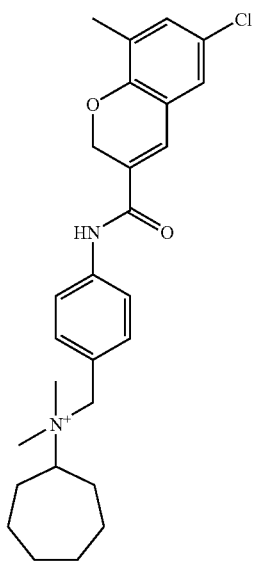
Cpd 118
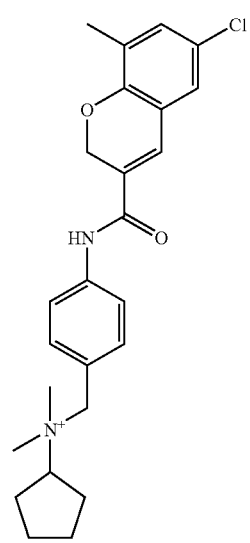
Cpd 119
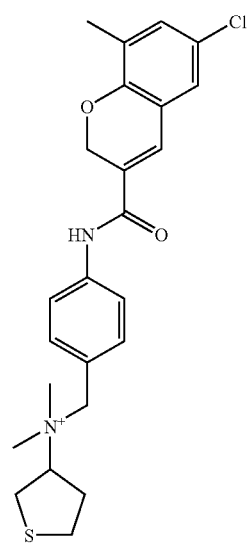
Cpd 120
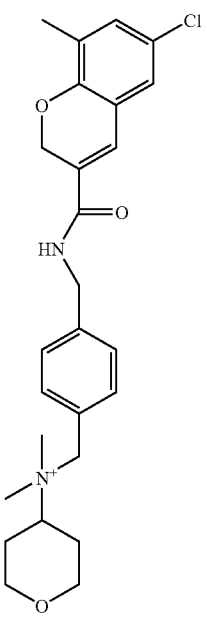
Cpd 121
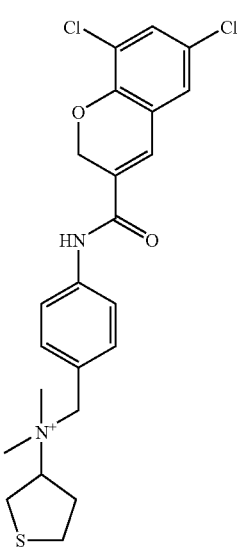
Cpd 122

Cpd 123
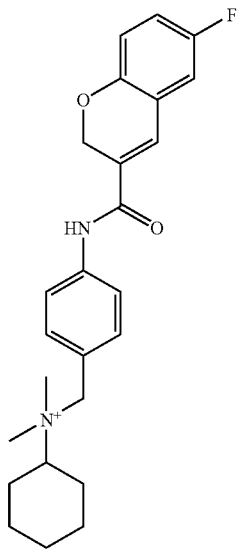
Cpd 124
Cpd 125
Cpd 126
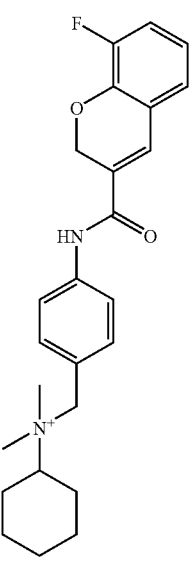
Cpd 127
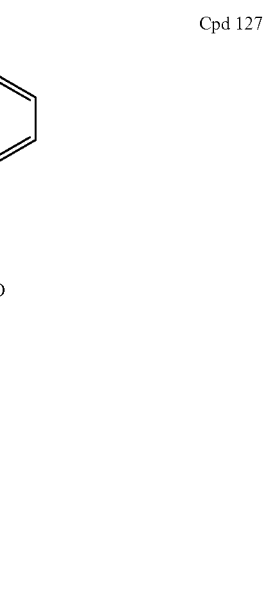

-continued
Cpd 128
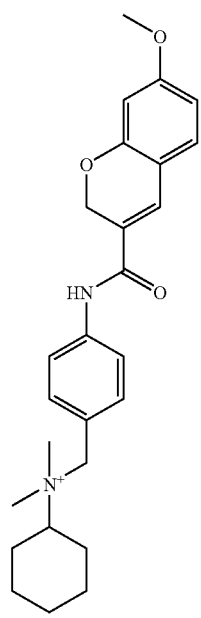
Cpd 129
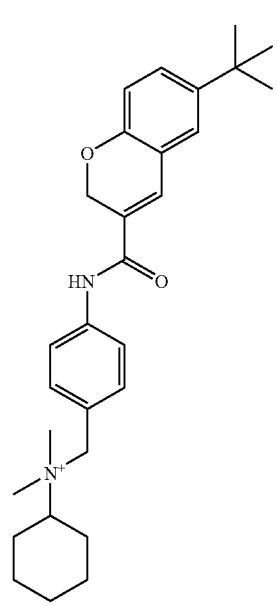
-continued
Cpd 130
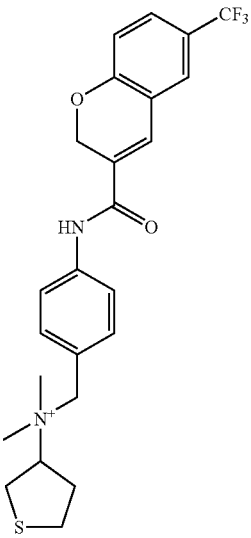
Cpd 131
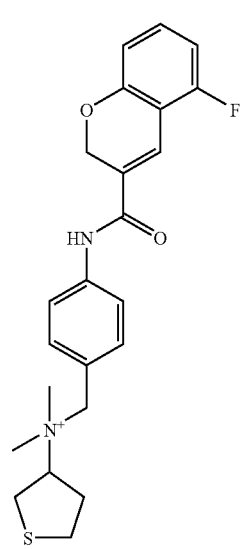
Cpd 132

Cpd 133
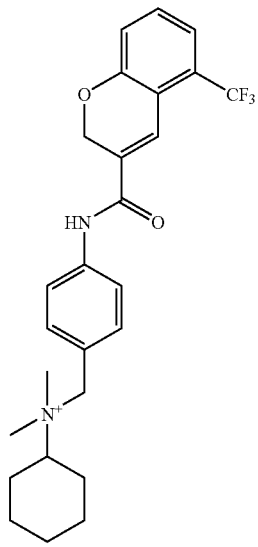
Cpd 134
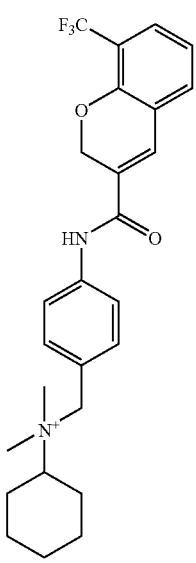
Cpd 135
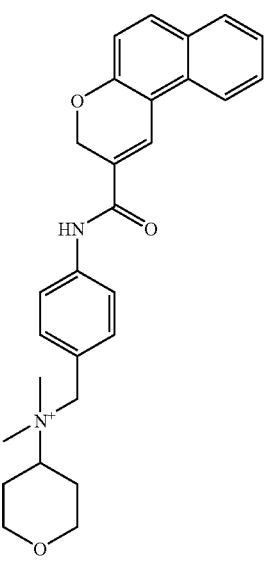
Cpd 136
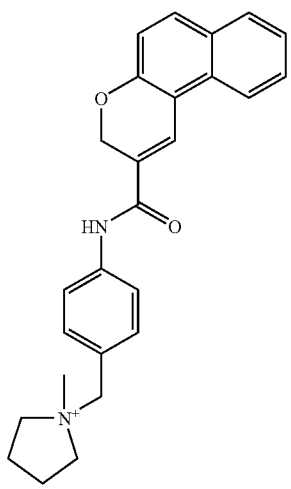
Cpd 137
Cpd 138

Cpd 139
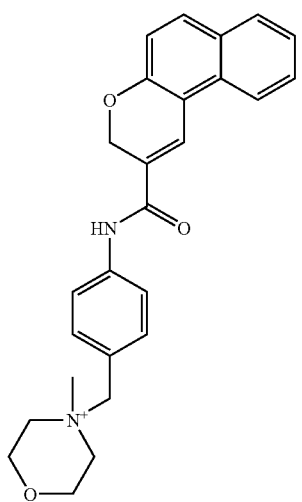
Cpd 140
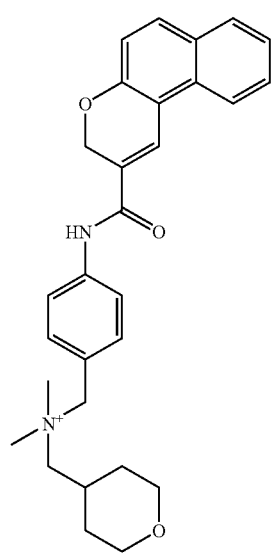
Cpd 141
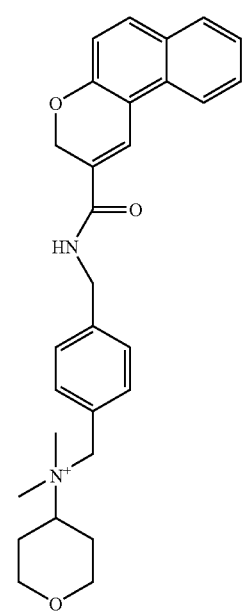
Cpd 142
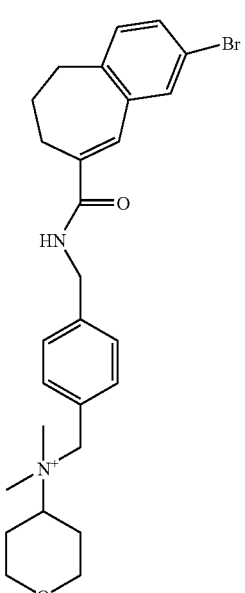
Cpd 143
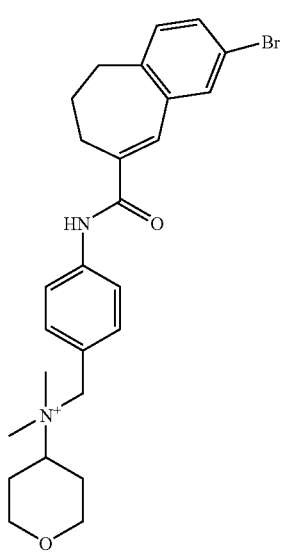

Cpd 144
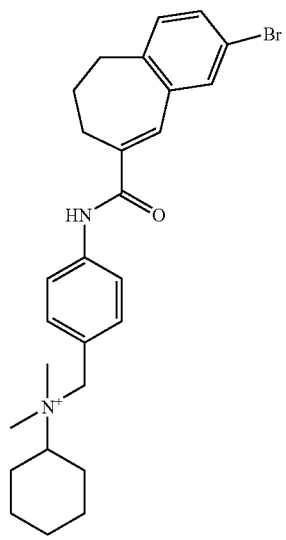
Cpd 147
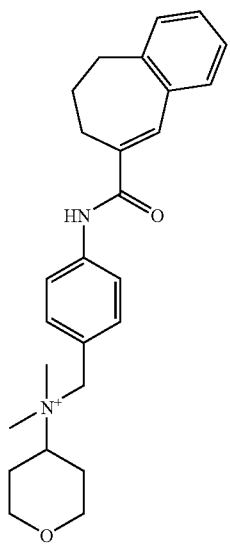
Cpd 145
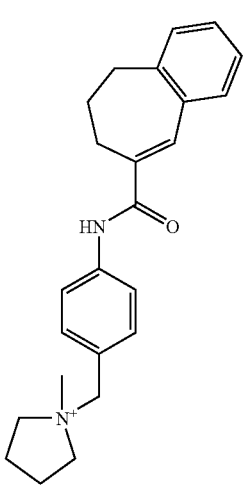
Cpd 146
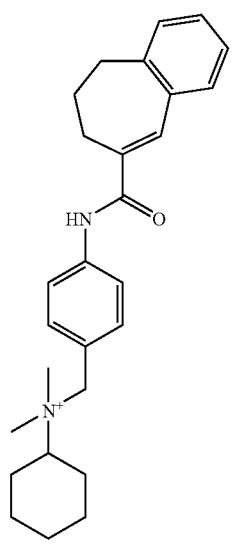
Cpd 148
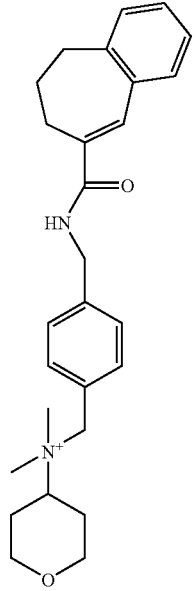

-continued
Cpd 149
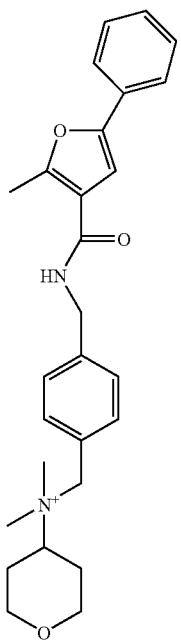
Cpd 150
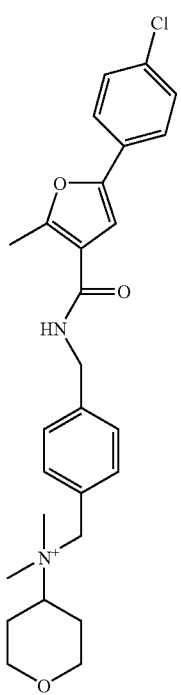
-continued
Cpd 151
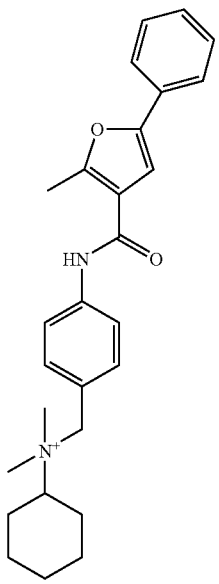
Cpd 152
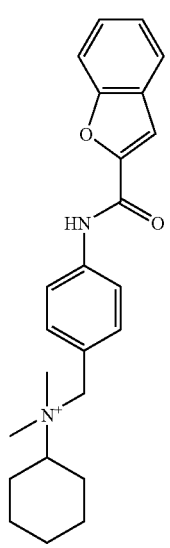

-continued
Cpd 153
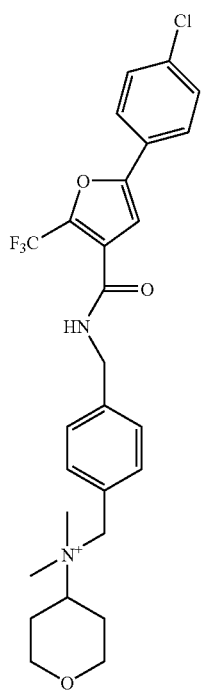
Cpd 154
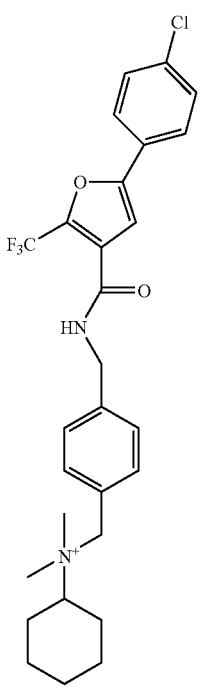
-continued
Cpd 155
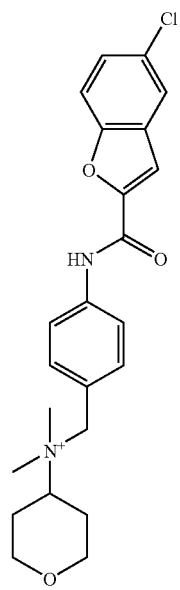
Cpd 156
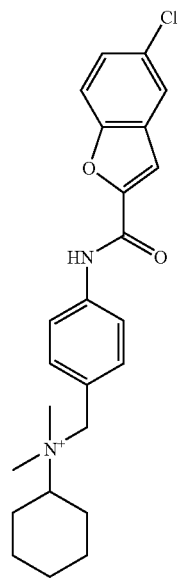

-continued
Cpd 157
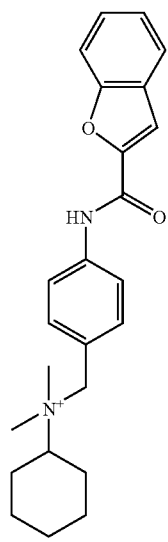
Cpd 158
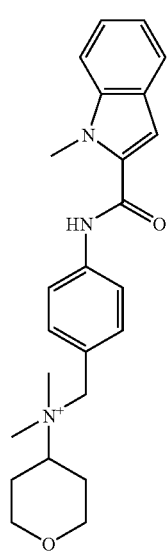
-continued
Cpd 159
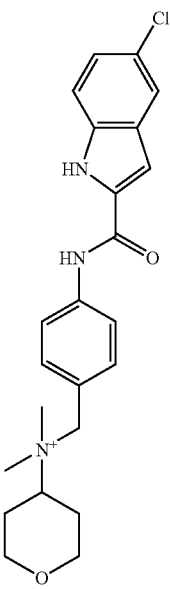
Cpd 160
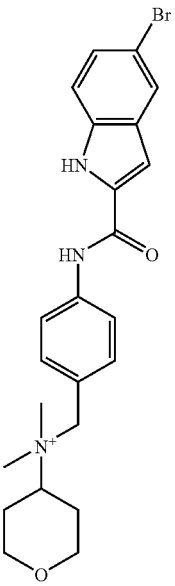

Cpd 161
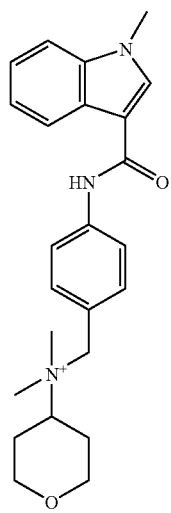
Cpd 163
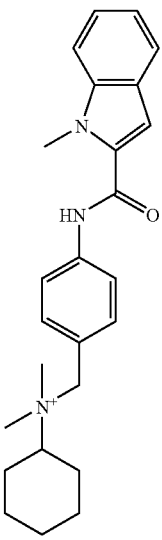
Cpd 162
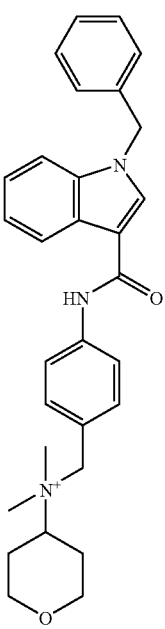
Cpd 164
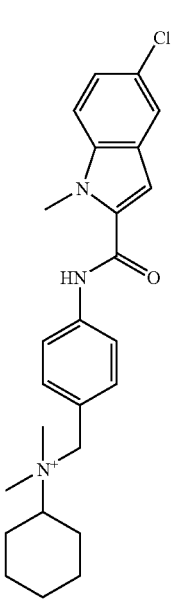

-continued
Cpd 165
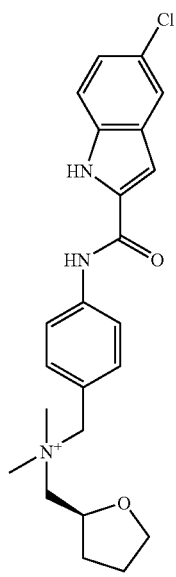
Cpd 167
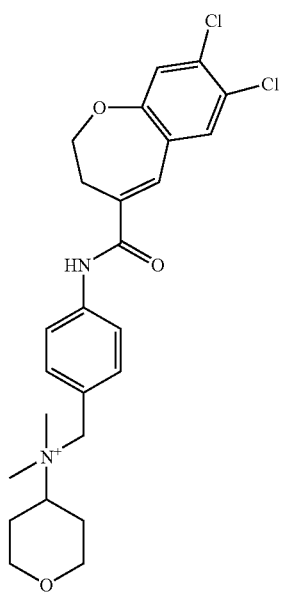
Cpd 166
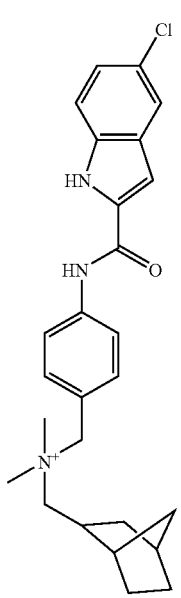
Cpd 168
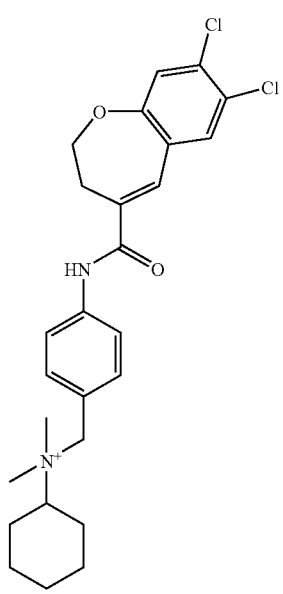

Cpd 169
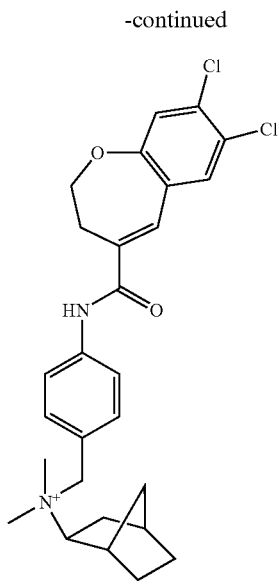
Cpd 170
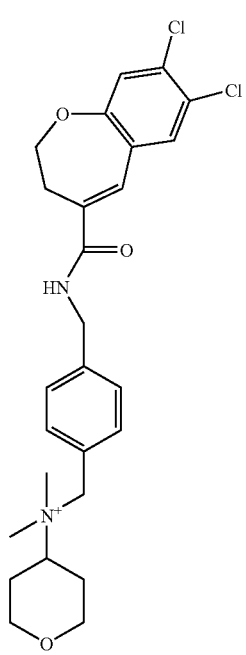
Cpd 171
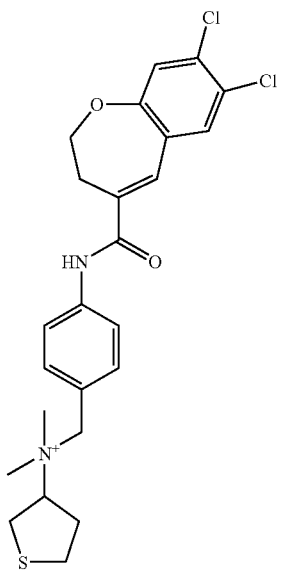
Cpd 172
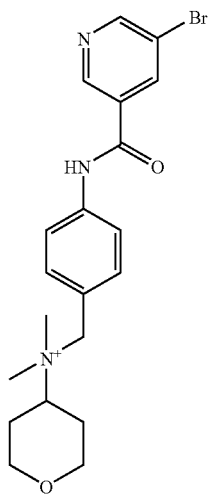
Cpd 173
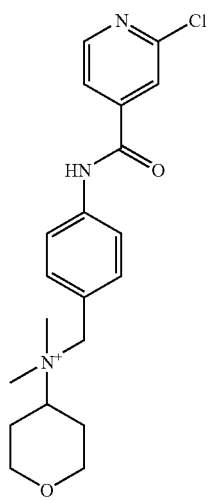

Cpd 174
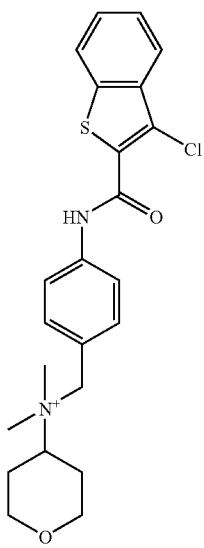
Cpd 175
Cpd 176
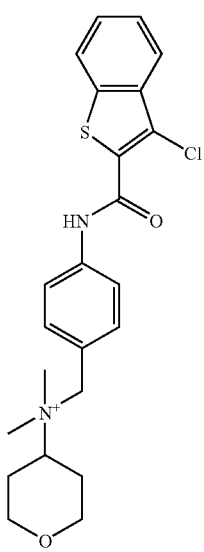
Cpd 177
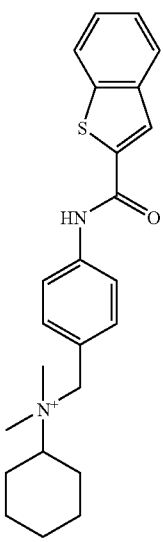
Cpd 178
An example of the invention is a compound of Formula (I) and pharmaceutically acceptable forms thereof selected from:

Cpd 14
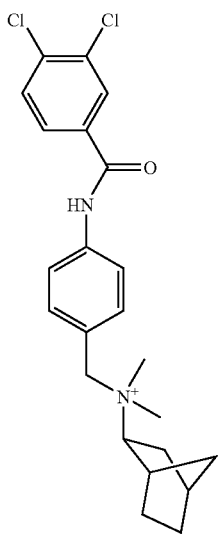
Cpd 17
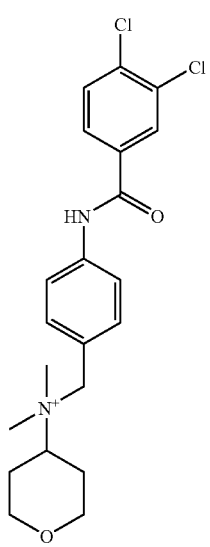
Cpd 19
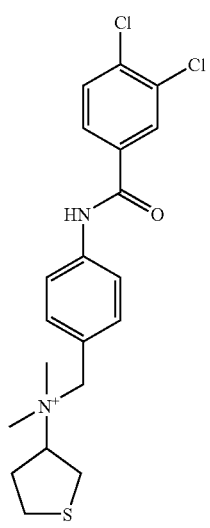
Cpd 75
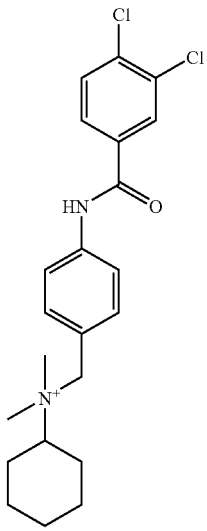
Cpd 80
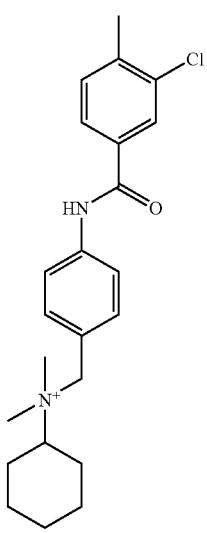
Cpd 82
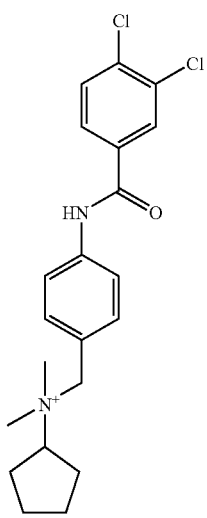

-continued
Cpd 114
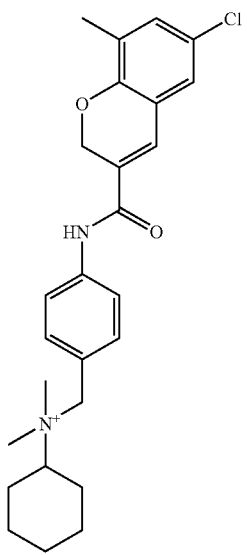
Cpd 115
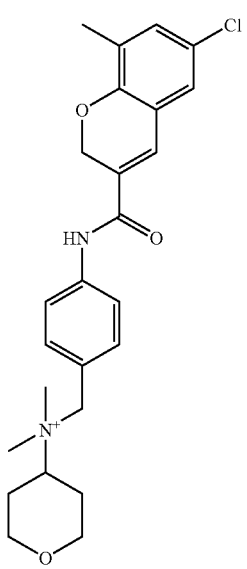
Cpd 120
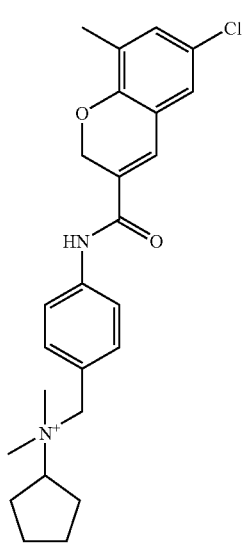
-continued
Cpd 127
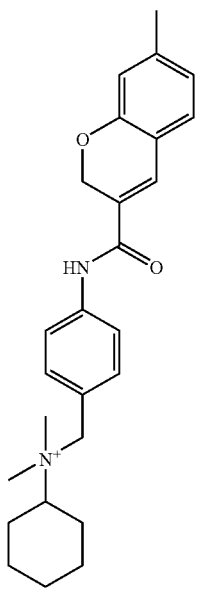
Cpd 137
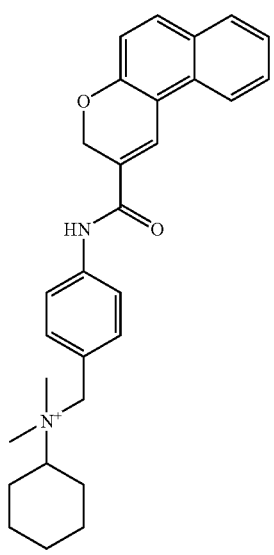

-continued

Cpd 143

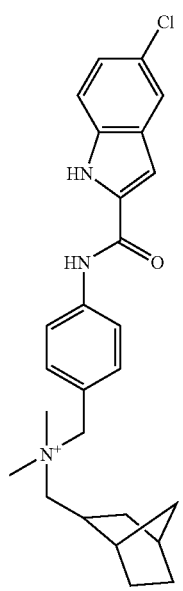

Cpd 166

Definitions

Bond lines drawn into a ring system from a substituent variable indicate that the substituent may be attached to any of the substitutable ring atoms.

As used herein, the following terms are intended to have the following definitions.

The term "alkyl" means a saturated aliphatic branched or straight-chain monovalent hydrocarbon radical or linking group substituent having from 1-8 carbon atoms, wherein the radical is derived by the removal of one hydrogen atom from a carbon atom and the linking group is derived by the removal of one hydrogen atom from each of two carbon atoms in the chain. The term includes, without limitation, methyl, ethyl, propyl, butyl, pentyl, hexyl and the like. An alkyl substituent may be attached to a core molecule via a terminal carbon atom or via a carbon atom within the chain. Similarly, any number of substituent variables may be attached to an alkyl substituent when allowed by available valences. The term "lower alkyl" means an alkyl substituent having from 1-4 carbon atoms.

The term "alkenyl" means a partially unsaturated alkyl substituent having at least one double bond derived by the removal of one hydrogen atom from each of two adjacent carbon atoms in the chain. The term includes, without limitation, vinyl, vinylidene, allyl, allylidene, isopropenyl, prenyl, methallyl and the like. An alkenyl substituent may be attached to a core molecule via a terminal carbon atom or via a carbon atom within the chain. Similarly, any number of substituent variables may be attached to an alkenyl substituent when allowed by available valences. The term "lower alkenyl" means an alkenyl substituent having from 1-4 carbon atoms.

The term "alkoxy" means an alkyl radical or linking group substituent attached through an oxygen-linking atom. The term includes, without limitation, methoxy, ethoxy, propoxy, butoxy and the like. An alkoxy substituent may be attached to a core molecule and further substituted where allowed.

The term "cycloalkyl" means a monovalent saturated or partially unsaturated monocyclic, polycyclic or bridged hydrocarbon ring system radical or linking group substituent. A ring of 3 to 20 carbon atoms may be designated by $C_{3-20}$ cycloalkyl; a ring of 5 to 15 carbon atoms may be designated by $C_{5-15}$ cycloalkyl; a ring of 3 to 8 carbon atoms may be designated by $C_{3-8}$ cycloalkyl and the like. The term includes, without limitation, cyclopropyl, cyclobutyl, cyclopentyl, cyclohexyl, cycloheptyl, cyclooctyl, 1H-indenyl, indanyl, 1,2,3,4-tetrahydro-naphthalenyl, 5,6,7,8-tetrahydro-naphthalenyl, 8,9-dihydro-7H-benzocyclohepten-6-yl, 6,7,8,9-tetrahydro-5H-benzocycloheptenyl, 5,6,7,8,9,10-hexahydro-benzocyclooctenyl, fluorenyl, bicyclo[2.2.1]heptyl, bicyclo[2.2.1]heptenyl, bicyclo[2.2.2]octyl, bicyclo[3.1.1]heptyl, bicyclo[3.2.1]octyl, bicyclo[2.2.2]octenyl, bicyclo[3.2.1]octenyl, adamantanyl, octahydro-4,7-methano-1H-indenyl, octahydro-2,5-methano-pentalenyl and the like. A cycloalkyl substituent may be attached to a core molecule and further substituted where allowed.

The term "aryl" means an unsaturated, conjugated π electron monocyclic or polycyclic hydrocarbon ring system radical or linking group substituent of 6, 9, 10 or 14 carbon atoms. The term includes, without limitation, phenyl, naphthalenyl, fluorenyl, indenyl, azulenyl, anthracenyl and the like. An aryl substituent may be attached to a core molecule and further substituted where allowed.

The term "heterocyclyl" means a saturated, partially unsaturated (such as those named with the prefix dihydro, trihydro, tetrahydro, hexahydro and the like) or unsaturated monocyclic, polycyclic or bridged hydrocarbon ring system radical or linking group substituent, wherein at least one ring carbon atom has been replaced with one or more heteroatoms independently selected from N, O or S. A heterocyclyl substituent further includes a ring system having up to 4 nitrogen atom ring members or a ring system having from 0 to 3 nitrogen atom ring members and 1 oxygen or sulfur atom ring member. Alternatively, up to two adjacent ring members may be a heteroatom, wherein one heteroatom is nitrogen and the other is selected from N, O or S. A heterocyclyl radical is derived by the removal of one hydrogen atom from a single carbon or nitrogen ring atom. A heterocyclyl linking group is derived by the removal of one hydrogen atom from two of either a carbon or nitrogen ring atom. A heterocyclyl substituent may be attached to a core molecule by either a carbon atom ring member or by a nitrogen atom ring member and further substituted where allowed.

The term heterocyclyl includes, without limitation, furanyl, thienyl, 2H-pyrrolyl, 2-pyrrolinyl, 3-pyrrolinyl, pyrrolidinyl, pyrrolyl, 1,3-dioxolanyl, oxazolyl, thiazolyl, imidazolyl, 2-imidazolinyl (also referred to as 4,5-dihydro-1H- imidazolyl), imidazolidinyl, 2-pyrazolinyl, pyrazolidinyl, pyrazolyl, isoxazolyl, isothiazolyl, oxadiazolyl, triazolyl, thiadiazglyl, tetrazolyl, tetrazolinyl, tetrazolidinyl, 2H-pyranyl, 4H-pyranyl, thiopyranyl, pyridinyl, piperidinyl, 1,4-dioxanyl, morpholinyl, 1,4-dithianyl, thiomorpholinyl, pyridazinyl, pyrimidinyl, pyrazinyl, piperazinyl, azetidinyl, azepanyl, indolizinyl, indolyl, isoindolyl, 3H-indolyl, indolinyl, benzofuranyl, benzo[b]thienyl, 1H-indazolyl, benzoimidazolyl, benzothiazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl, quinuclidinyl, 2H-chromenyl, 3H-benzo[f]chromenyl, tetrahydro-furanyl, tetrahydro-thienyl, tetrahydro-pyranyl, tetrahydro-thiopyranyl, tetrahydro-pyridazinyl, hexahydro-1,4-diazepinyl, hexahydro-1,4-oxazepanyl, 2,3-dihydro-benzo[b]oxepinyl, 1,3-benzodioxolyl (also known as 1,3-methylenedioxyphenyl), 2,3-dihydro-1,4-benzodioxinyl (also known as 1,4-ethylenedioxyphenyl), benzo-dihydro-furanyl (also known as 2,3-dihydro-benzofuranyl), benzo-tetrahydro-pyranyl, benzo-dihydro-thienyl, 5,6,7,8-tetrahydro-4H-cyclohepta[b]thienyl; 5,6,7-trihydro-4H-cyclohexa[b]thienyl, 5,6-dihydro-4H-cyclopenta[b]thienyl, 2-aza-bicyclo[2.2.1]heptyl, 1-aza-bicyclo[2.2.2]octyl, 8-aza-bicyclo[3.2.1]octyl, 7-oxa-bicyclo[2.2.1]heptyl, pyrrolidinium, piperidinium, piperazinium, morpholinium and the like.

The term "independently selected" refers to two or more substituents that may be selected from a substituent variable group, wherein the selected substituents may be the same or different.

The term "dependently selected" refers to one or more substituent variables that are specified in an indicated combination for substitution in a core molecule (e.g., variables that refer to groups of substituents appearing in a tabular list of compounds).

The term "carbonyl" means a linking group having the formula —C(O)— or —C(═O)—.

The term "thiocarbonyl" means a linking group having the formula —C(S)— or —C(═S)—.

The term "sulfonyl" means a linking group having the formula —SO$_2$—.

The term "alkoxycarbonyl" means a radical having the formula —C(O)O-alkyl.

Pharmaceutically Acceptable Forms

Pharmaceutically acceptable forms according to the invention may, alternatively or in addition to a compound of Formula (I), comprise a pharmaceutically acceptable salt of a compound of Formula (I) or a prodrug or pharmaceutically active metabolite of such a compound or salt.

The compounds of the invention may be present in the form of pharmaceutically acceptable salts. For use in medicines, the salts of the compounds of this invention refer to non-toxic "pharmaceutically acceptable salts." FDA-approved pharmaceutically acceptable salt forms include pharmaceutically acceptable acidic/anionic or basic/cationic salts.

Pharmaceutically acceptable acidic/anionic salts include, without limitation, acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide salts.

Organic or inorganic acids also include, and are not limited to, hydroiodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, NH$_3$, NH$_4$OH, N-methyl-D-glucamine, piperidine, potassium, potassium-t-butoxide, potassium hydroxide (aqueous), procaine, quinine, sodium, sodium carbonate, sodium-2-ethylhexanoate (SEH), sodium hydroxide, triethanolamine (TEA) or zinc.

The compounds of the invention may be present in the form of pharmaceutically acceptable prodrugs and metabolites thereof. In general, such prodrugs and metabolites will be functional derivatives of the compounds that are readily convertible in vivo into an active compound.

The term "prodrug" means a pharmaceutically acceptable form of a functional derivative of a compound of the invention (or a salt thereof), wherein the prodrug may be: 1) a relatively active precursor which converts in vivo to an active prodrug component; 2) a relatively inactive precursor which converts' in vivo to an active prodrug component; or 3) a relatively less active component of the compound that contributes to therapeutic biological activity after becoming available in vivo (i.e., as a metabolite). Conventional procedures for the selection and preparation of suitable prodrug derivatives are described in, for example, "*Design of Prodrugs*", ed. H. Bundgaard, Elsevier, 1985.

The term "metabolite" means a pharmaceutically acceptable form of a metabolic derivative of a compound of the invention (or a salt thereof), wherein the derivative is a relatively less active component of the compound that contributes to therapeutic biological activity after becoming available in vivo.

The present invention also contemplates compounds of Formula (I) in various stereoisomeric or tautomeric forms. The invention encompasses all such CCR2 inhibiting compounds, including active compounds in the form of essentially pure enantiomers, racemic mixtures and tautomers or pharmaceutically acceptable forms thereof.

The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers).

The term "stereoisomer" refers to isomers of identical constitution that differ in the arrangement of their atoms in space. Enantiomers and diastereomers are stereoisomers wherein an asymmetrically substituted carbon atom acts as a chiral center. The term "chiral" refers to a molecule that is not superposable on its mirror image, implying the absence of an axis and a plane or center of symmetry. The term "enantiomer" refers to one of a pair of molecular species that are mirror images of each other and are not superposable. The term "diastereomer" refers to stereoisomers that are not related as mirror images. The symbols "R" and "S" represent the configuration of substituents around a chiral carbon atom(s). The symbols "R*" and "S*" denote the relative configurations of substituents around a chiral carbon atom(s).

The term "racemate" or "racemic mixture" refers to a compound of equimolar quantities of two enantiomeric species, wherein the compound is devoid of optical activity. The term "optical activity" refers to the degree to which a chiral molecule or nonracemic mixture of chiral molecules rotates the plane of polarized light.

The term "geometric isomer" refers to isomers that differ in the orientation of substituent atoms in relationship to a carbon-carbon double bond, to a cycloalkyl ring or to a bridged bicyclic system. Substituent atoms (other than H) on each side of a carbon-carbon double bond may be in an E or Z configuration. In the "E" or "chair" configuration, the substituents are on opposite sides in relationship to the carbon-carbon double bond; in the "Z" or "boat" configuration, the substituents are oriented on the same side in relationship to the carbon-carbon double bond.

Substituent atoms (other than H) attached to a hydrocarbon ring may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans". Substituent atoms (other than H) attached to a bridged bicyclic system may be in an "endo" or "exo" configuration. In the "endo" configuration, the substituents attached to a bridge (not a bridgehead) point toward the larger of the two remaining bridges; in the "exo" configuration, the substituents attached to a bridge point toward the smaller of the two remaining bridges.

It is to be understood that the various substituent stereoisomers, geometric isomers and mixtures thereof used to prepare compounds of the present invention are either commercially available, can be prepared synthetically from commercially available starting materials or can be prepared as isomeric mixtures and then obtained as resolved isomers using techniques well-known to those of ordinary skill in the art.

The isomeric descriptors "R," "S," "S*," "R*," "E," "Z," "cis," "trans", "exo", and "endo", where used herein, indicate atom configurations relative to a core molecule and are intended to be used as defined in the literature.

The compounds of the present invention may be prepared as individual isomers by either isomer-specific synthesis or resolved from an isomeric mixture. Conventional resolution techniques include forming the free base of each isomer of an isomeric pair using an optically active salt (followed by fractional crystallization and regeneration of the free base), forming an ester or amide of each of the isomers of an isomeric pair (followed by chromatographic separation and removal of the chiral auxiliary) or resolving an isomeric mixture of either a starting material or a final product using various well known chromatographic methods.

Furthermore, compounds of the present invention may have a plurality of polymorph or amorphous crystalline forms and, as such, are intended to be included in the scope of the invention. In addition, some of the compounds may form a plurality of solvates with water (i.e., hydrates) or common organic solvents, such are also intended to be encompassed within the scope of this invention.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known in the art.

Therapeutic Use

Pharmaceutically acceptable forms of a compound of Formula (I) or a composition or medicament thereof in accordance with the invention are CCR2 antagonists. Said composition or medicament may contain a compound of Formula (I) having a mean inhibition constant ($IC_{50}$) against MCP-1 binding to CCR2 of between about 5 µM to about 1 µM; between about 1 µM to about 1 nM; between about 800 nM to about 1 nM; between about 200 nM to about 1 nM; between about 100 nM to about 1 nM; between about 80 nM to about 1 nM; between about 20 nM to about 1 nM; between about 10 nM to about 1 nM; or about 1 nM.

A compound of Formula (I) or a composition or medicament thereof reduces MCP-1 induced monocyte chemotaxis. Said composition or medicament may contain a compound of Formula (I) having an $IC_{50}$ for reduction in MCP-1 induced monocyte chemotaxis of between about 5 µM to about 1 nM; between about 1 µM to about 1 nM; between about 800 nM to about 1 nM; between about 200 nM to about 1 nM; between about 100 nM to about 1 nM; between about 80 nM to about 1 nM; between about 20 nM to about 1 nM; between about 10 nM to about 1 nM; or about 1 nM.

A compound of Formula (I) or a composition or medicament thereof reduces MCP-1 intracellular calcium mobilization. Said composition or medicament may contain a compound of Formula (I) having an $IC_{50}$ for reduction in MCP-1 induced intracellular calcium mobilization of between about 5 µM to about 1 nM; between about 1 µM to about 1 nM; between about 800 nM to about 1 nM; between about 200 nM to about 1 nM; between about 100 nM to about 1 nM; between about 80 nM to about 1 nM; between about 20 nM to about 1 nM; between about 10 nM to about 1 nM; or about 0.1 nM.

Accordingly, a compound of Formula (I) or a composition or medicament thereof is useful in a method for preventing, treating or ameliorating a CCR2 mediated inflammatory syndrome, disorder or disease in a subject in need thereof comprising administering to the subject an effective amount of a compound of Formula (I) or composition or medicament thereof.

The present invention is directed to a method for preventing, treating or ameliorating a CCR2 mediated inflammatory syndrome, disorder or disease in a subject in need thereof comprising administering to the subject an effective amount of a compound of Formula (I) or composition or medicament thereof.

The term "administering," with respect to the methods of the invention, means a method for preventing, treating or ameliorating a syndrome, disorder or disease as described herein with a compound of Formula (I) or composition or medicament thereof. Such methods include administering an effective amount of said compound, composition or medicament at different times during the course of a therapy or concurrently in a combination form. The methods of the invention are to be understood as embracing all known therapeutic treatment regimens.

The term "subject" as used herein, means an animal, typically a mammal, typically a human, typically a patient with a syndrome, disorder or disease that is associated with elevated MCP-1 expression or MCP-1 overexpression, or a patient with an inflammatory condition that accompanies syndromes, disorders or diseases associated with elevated MCP-1 expression or MCP-1 overexpression.

The term "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

The effective amount of a compound of the invention in such a therapeutic method is from about 0.001 mg/kg/day to about 300 mg/kg/day.

The invention includes the use of an instant compound for the preparation of a composition or medicament for preventing, treating or ameliorating a CCR2 mediated inflammatory syndrome, disorder or disease in a subject in need thereof, wherein the composition or medicament comprises a mixture one or more compounds of the invention and an optional pharmaceutically acceptable carrier.

The term "composition" means a product comprising a compound of the invention, such as a product comprising the specified ingredients in the specified amounts, as well as any product which results, directly or indirectly, from such combinations of the specified ingredients in the specified amounts and one or more pharmaceutically acceptable carriers therefor.

The term "medicament" means a product for use in preventing, treating or ameliorating a CCR2 mediated inflammatory syndrome, disorder or disease.

The term "pharmaceutically acceptable carrier" means molecular entities and compositions that are of sufficient purity and quality for use in the formulation of a composition or medicament of the invention and that, when appropriately administered to an animal or a human, do not produce an adverse, allergic, of other untoward reaction. Since both human and veterinary use is included within the scope of the invention, a pharmaceutically acceptable formulation includes a composition or medicament for either human or veterinary use.

The term "CCR2 mediated inflammatory syndrome, disorder or disease" means, without limitation, syndromes, disorders or diseases associated with elevated MCP-1 expression, MCP-1 overexpression or inflammatory conditions that accompany syndromes, disorders or diseases associated with elevated MCP-1 expression or MCP-1 overexpression.

The terms "elevated MCP-1 expression" or "MCP-1 overexpression" mean unregulated or up-regulated CCR2 activation as a result of MCP-1 binding.

The term "unregulated" means unwanted CCR2 activation in a multicellular organism resulting in harm (such as discomfort or decreased life expectancy) to the multicellular organism.

The term "up-regulated" means: 1). increased or unregulated CCR2 activity or expression, or 2). increased CCR2 expression leading to unwanted monocyte and lymphocyte migration. The existence of an inappropriate or abnormal level of MCP-1 or activity of CCR2 is determined by procedures well known in the art.

CCR2 mediated inflammatory syndromes, disorders or diseases include, without limitation, ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, diabetes and diabetic complications, diabetic nephropathy, diabetic retinopathy, diabetic retinitis, diabetic microangiopathy, tuberculosis, chronic obstructive pulmonary disease, sarcoidosis, invasive staphyloccocia, inflammation after cataract surgery, allergic rhinitis, allergic conjunctivitis, chronic urticaria, asthma, allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach.

The term "uveitis" generically refers to any inflammatory disease involving the eye. Uveitis can be divided into clinically distinct subtypes based on the part of the eye in which the inflammation is present (percentages correspond to patients known to fit these categories): anterior (51%), intermediate (13%), posterior (20%), or panuveitis (16%) and, according to the course of the disease, as either acute (16%), recurring (26%), or chronic (58%). Those with 1.0 anterior uveitis (~19%) eventually develop irreparable vision damage despite aggressive treatment such as unilateral blindness (9%), bilateral blindness (2%), or unilateral or bilateral vision impairment (8%). Most cases of uveitis are idiopathic, but known causes include infection (e.g., toxoplasmosis, cytomegalovirus, and the like) or development as a component of a systemic inflammatory and/or autoimmune disorder (e.g., juvenile RA, HLA-B27-associated spondyloarthropathies, sarcoidosis, and the like).

Patients with anterior uveitis have MCP-1 present in large quantities in the aqueous humor of the eye. The amount of MCP-1 correlates with the severity of the clinical symptoms and the large number of mononuclear cells present in the cellular infiltrate. Uveitis is also a potential complication resulting from cataract surgery and prophylactic use of antibiotics and corticosteroids is common for such patients. Currently, most patients with anterior uveitis are first treated with topical corticosteroids. Injected or oral steroids may be used in severe cases, or if the disease is recurrent or chronic. If steroids are ineffective, immunosuppressive agents (e.g., cyclosporine, methotrexate, azathioprine, cyclophosphamide, and the like) are used, particularly if the patient's vision is in danger. All of these drugs have potentially severe side-effects, particularly in children, and there is general agreement that there is an unmet medical need for safe and effective steroid substitutes or steroid-sparing agents.

An example of the invention is a method for preventing, treating or ameliorating CCR2 mediated ophthalmic disorders (such as uveitis, allergic conjunctivitis and the like), rheumatoid arthritis, psoriasis, psoriatic arthritis, atopic dermatitis, chronic obstructive pulmonary disease, allergic rhinitis, asthma, allergic asthma, periodontal diseases (such as periodonitis, gingivitis, gum disease and the like) in a subject in need thereof comprising administering to the subject an effective amount of a compound of Formula (I) or composition or medicament thereof.

Another example of the invention is a method for preventing, treating or ameliorating CCR2 mediated uveitis, wherein uveitis includes, without limitation, acute, recurring or chronic uveitis (such as anterior uveitis, intermediate uveitis, posterior uveitis, panuveitis and the like) in a subject in need thereof comprising administering to the subject an effective amount of a compound of Formula (I) or composition or medicament thereof.

An example of the invention is a method for preventing, treating or ameliorating CCR2 mediated acute uveitis, recurring uveitis, chronic uveitis, allergic conjunctivitis, rheumatoid arthritis, psoriasis, psoriatic arthritis, atopic dermatitis, chronic obstructive pulmonary disease, allergic rhinitis, asthma, allergic asthma, periodontis, gingivitis or gum disease in a subject in need thereof comprising administering to the subject an effective amount of a compound of Formula (I) or composition or medicament thereof.

The invention includes a method for preventing, treating or ameliorating a CCR2 mediated inflammatory syndrome, disorder or disease in a subject in need thereof comprising administering to the subject an effective amount of a compound of Formula (I) or composition or medicament thereof in a combination therapy with one or more anti-inflammatory agents (such as a small molecule, antibiotic, corticosteroid, steroid, and the like), anti-infective agents or immunosuppressive agents.

The term "combination therapy" refers to the use of a compound of Formula (I) or composition or medicament thereof in combination with an anti-inflammatory, anti-infective, or immunosuppressive agent for preventing, treating or ameliorating a CCR2 mediated inflammatory syndrome, disorder or disease.

For preventing, treating or ameliorating a CCR2 mediated inflammatory syndrome, disorder or disease using a compound of Formula (I) or composition or medicament thereof and an anti-inflammatory, anti-infective or immunosuppressive agent in a combination therapy includes, without limitation, co-administration of the compound and the agent, sequential administration of the compound and the agent, administration of a composition containing of the compound and the agent or simultaneous administration of separate compositions containing of the compound and the agent.

Pharmaceutical Compositions

The present invention includes a pharmaceutical composition or medicament comprising one or more of the instant compounds and an optional pharmaceutically acceptable carrier.

The present invention further includes a process for making a pharmaceutical composition or medicament comprising mixing one or more of the instant compounds and an optional pharmaceutically acceptable carrier; and, includes those compositions or medicaments resulting from such a process. Contemplated processes include both conventional and unconventional pharmaceutical techniques.

The composition or medicament may take a wide variety of forms to effectuate mode of administration ocularly, intranasally (by inhalation or insufflation), sublingually, orally, parenterally or rectally including, without limitation, ocular (via a delivery device such as a contact lens and the like), intranasal (via a delivery device), transdermal, topical with or without occlusion, intravenous (both bolus and infusion), injection (intraperitoneally, subcutaneously, intramuscularly, intratumorally, or parenterally) and the like.

The composition or medicament may be in a dosage unit such as a tablet, pill, capsule, powder, granule, liposome, biodegradable carrier, ion exchange resin, sterile solution and the like (facilitating immediate release, timed release, or sustained release), parenteral solution or suspension, metered aerosol or liquid spray, drop, ampoule, auto-injector device or suppository.

Compositions or medicaments suitable for oral administration include solid forms such as pills, tablets, caplets, capsules (each including immediate release, timed release, and sustained release formulations), granules and powders and liquid forms such as solutions, syrups, elixirs, emulsions and suspensions. Forms useful for nasal administration include sterile solutions or nasal delivery devices. Forms useful for ocular administration include sterile solutions or ocular delivery devices. Forms useful for parenteral administration include sterile solutions, emulsions and suspensions.

Alternatively, the composition or medicament may be administered in a form suitable for once-weekly or once-monthly administration. For example, an insoluble salt of the active compound may be adapted to provide a depot preparation for intramuscular injection (e.g., a salt form) or to provide a solution for nasal or ocular administration (e.g., a quaternary ammonium salt).

The dosage form (tablet, capsule, powder, solution, contact lens, patch, liposome, ion exchange resin, suppository, teaspoonful, and the like) containing the composition or medicament thereof contains an effective amount of the active ingredient necessary to provide a therapeutic effect.

The composition or medicament may contain an effective amount of from about 0.001 mg to about 5000 mg (preferably, from about 0.001 to about 500 mg) of a compound of the present invention or a pharmaceutically acceptable form thereof and may be constituted into any form suitable for the mode of administration selected for a subject in need.

A contemplated range of the effective amount includes from about 0.001 mg to about 300 mg/kg of body weight per day. A contemplated range also includes from about 0.003 to about 100 mg/kg of body weight per day. Another contemplated range includes from about 0.005 to about 15 mg/kg of body weight per day. The composition or medicament may be administered according to a dosage Regimen of from about 1 to about 5 times per day.

For oral administration, the composition or medicament is preferably in the form of a tablet containing, e.g., 0.01, 0.05, 0.1, 0.5, 1.0, 2.5, 5.0, 10.0, 15.0, 25.0, 50.0, 100, 150, 200, 250, and 500 milligrams of the active ingredient for the symptomatic adjustment of the dosage to the patient to be treated. Optimal dosages will vary depending on factors associated with the particular patient being treated (e.g., age, weight, diet, and time of administration), the severity of the condition being treated, the compound being employed, the mode of administration, and the strength of the preparation. The use of either daily administration or post-periodic dosing may be employed.

For ocular administration, the composition is preferably in the form of an ophthalmic composition. The ophthalmic compositions are preferably formulated as eye-drop formulations and filled in appropriate containers to facilitate administration to the eye, for example a dropper fitted with a suitable pipette. Preferably the compositions are sterile and aqueous based, using purified water. In addition to the compound of the invention, an ophthalmic composition may contain one or more of: a) a surfactant such as a polyoxyethylene fatty acid ester; b) a thickening agents such as cellulose, cellulose derivatives, carboxyvinyl polymers, polyvinyl polymers, and polyvinylpyrrolidones, typically at a concentration n the range of about 0.05 to about 5.0% (wt/vol); c) (as an alternative to or in addition to storing the composition in a container containing nitrogen and optionally including a free oxygen absorber such as Fe), an anti-oxidant such as butylated hydroxyanisol, ascorbic acid, sodium thiosulfate, or butylated hydroxytoluene at a concentration of about 0.00005 to about 0.1% (wt/vol); d) ethanol at a concentration of about 0.01 to 0.5% (wt/vol); and e) other excipients such as an isotonic agent, buffer, preservative, and/or pH-controlling agent. The pH of the ophthalmic composition is desirably within the range of 4 to 8.

Synthetic Methods

Representative compounds of the present invention can be synthesized in accordance with the general synthetic schemes described below and are illustrated more particularly in the specific examples that follow. The general schemes and specific examples are offered by way of illustration; the invention should not be construed as being limited by the chemical reactions and conditions expressed. The methods for preparing the various starting materials used in the schemes and examples are well within the skill of persons versed in the art. All commercially available chemicals were obtained from commercial suppliers and used without further purification. Particular equipment components used in the examples such as reaction vessels and the like are also commercially available.

The following abbreviations have the indicated meanings:

| | |
|---|---|
| Cpd | compound |
| Boc | tert-butoxy carbonyl or t-butoxy carbonyl |
| Boc$_2$O | di-t-butyl-dicarbonate |
| conc. | concentrated |
| DABCO | 1,4-diazabicyclo[2.2.2]octane |
| DBU | 1,8-diazabicyclo[5.4.0]undec-7-ene |
| DCM or CH$_2$Cl$_2$ | dichloromethane |
| DMAP | (4,4-dimethylamino)-pyridine |
| DMF | N,N-dimethyl formamide |
| EDIC | 1-(3-dimethylaminopropyl)-3-ethylcarbodiimide |
| Et$_2$O | ethoxy-ethane or ether |
| EtOAc | ethylacetate |
| EtOH | ethanol |
| HCOH | formaldehyde |
| HOBt | 1-hydroxybenzotriazole hydrate |
| MeI or CH$_3$I | methyl iodide |
| MeOH | methanol |
| min(s)/hr(s)/d(s) | minute(s)/hour(s)/day(s) |
| Pd(dppf)$_2$ | {[1,1'-bis(diphenylphosphino)-ferrocene]dichloropalladium(II)} |
| RT/rt/r.t. | room temperature |
| NaB(OAc)$_3$H | sodium triacetoxyborohydride |
| TEA or Et$_3$N | triethylamine |
| THF | tetrahydrofuran |

Scheme A

The synthetic method provided by Scheme A, depending on the starting materials used or when certain reaction conditions are desired, is used to prepare a compound of Formula (I).

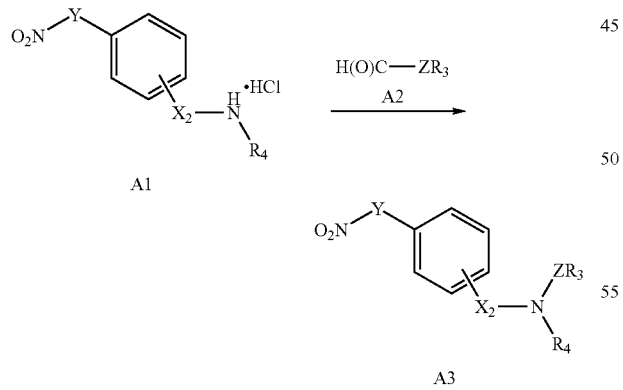

A mixture of a nitrophenylamine hydrochloride Compound A1 and a solution of an aldehyde or ketone Compound A2 (in a solvent such as CH$_2$Cl$_2$ and the like) is cooled to 0° C., then Et$_3$N is added followed by NaB(OAc)$_3$H. The resulting suspension is stirred and allowed to warm to r.t. for about 8-12 hrs (adapted from Shiroshi, et al., *J. Med. Chem.*, 2000, 43, 2049).

An aldehyde (such as formaldehyde and the like) in aqueous solution is added, followed by NaB(OAc)$_3$H added in one portion while cooling the reaction vessel with ice. The reaction mixture is stirred at r.t. for about 12 hrs, then made basic (using a solution of 2N NaOH, and the like) and extracted (with a solvent such as CH$_2$Cl$_2$ and the like). The organic layer is washed using brine, then separated and dried over Na$_2$SO$_4$. The drying agent is filtered and the solvent is removed in vacuo to yield a disubstituted nitrophenylamine Compound A3 (adapted from Hashimoto et al., *Org. Proc. R&D*, 2002, 6, 70).

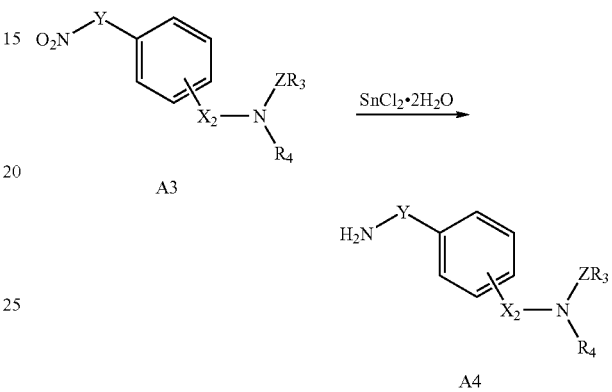

SnCl$_2$.2H$_2$O in conc. HCl is added in small portions to a solution of Compound A3 (in a solvent such as THF and the like) at r.t. The mildly exothermic reaction is maintained at r.t. using an ice-cooled water bath and stirred for about 1 hr. The round bottom flask containing the reaction mixture is placed in a warm water bath for about 30 min to allow the reaction to reach completion. The mixture is sequentially diluted with a solvent (such as THF and the like) and water, then made basic (using a solution of 2N NaOH and the like). The layers are separated and the aqueous layer is extracted (using a solvent such as Et$_2$O and the like). The combined organic layers were dried over MgSO$_4$, then filtered and the solvent was removed in vacuo. The solid obtained was further dried (by pressing the solid on an absorbent surface such as a filter paper) to provide a disubstituted aminophenylamine Compound A4.

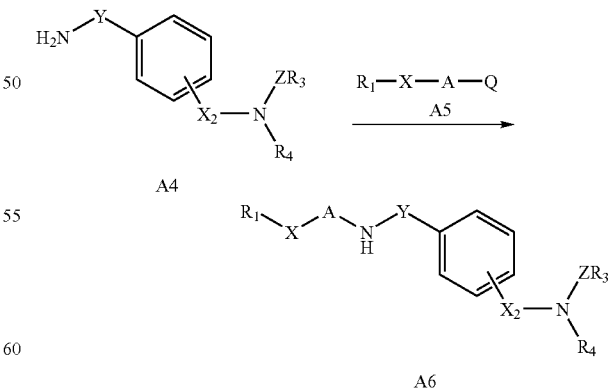

A solution of a R$_1$ substituted Compound A5 (wherein Q represents a leaving group such as chloride or hydroxy) is added dropwise via a dropping funnel over a period of about 20 min to a solution of Compound A4 (in a solvent mixture such as Et₃N in THF and the like). The resulting suspension is allowed to warm to r.t. over a period of about 8-12 hrs, then made basic (using a solution of 2N NaOH and the like). The organic and aqueous layers are separately extracted (using a solvent such as EtOAc and the like). The organic layer is washed with brine, then dried (using MgSO₄, Na₂SO₄ and the like) and filtered. The solvent is removed in vacuo to yield a crude product which may be purified by either flash column chromatography (in a solvent ratio 15:1 EtOAc:MeOH to 6:1 EtOAc:MeOH) or preparative TLC (using a solvent mixture in a ratio of EtOAc:MeOH) to provide a substituted benzamide Compound A6.

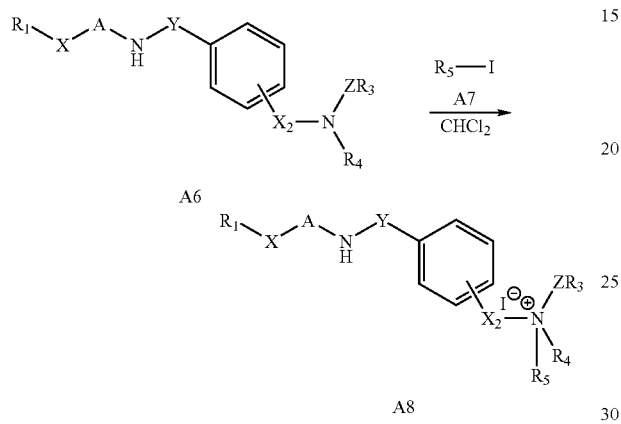

An R₅ substituted iodo Compound A7 is added to a solution of Compound A6 (in a solvent mixture such as acetone and acetonitrile and the like) at r.t. The resulting solution is stirred for about 8-12 hrs to form a precipitate. The solvent is removed in vacuo and the solid is sequentially washed (using EtOAc and Et₂O and the like), then dried in a vacuum oven for about 12 hrs to provide a quaternary salt Compound A8.

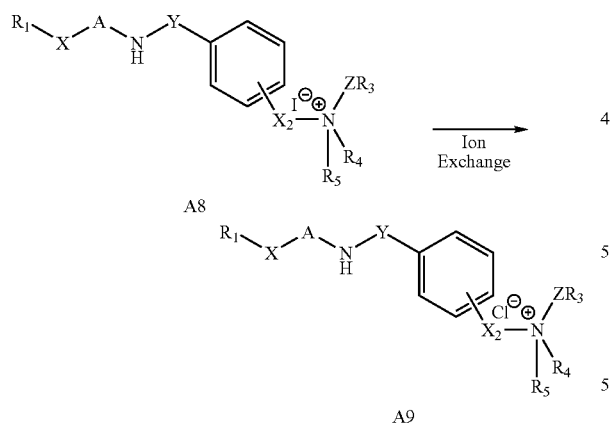

A solution of Compound A8 (in a solvent:water ratio mix such ad a 1:1 MeOH:H₂O) is passed through a column packed with an ion-exchange resin (such as ~300 g of Bio-Rad analytical grade anion exchange resin. AG 1-X8, 50-100 mesh, chloride form) into a flask. The column is then washed (such as with MeOH and the like) and solvents (such as acetone and Et₂O and the like) are added to the filtered product in the flask: The solvent is removed in vacuo and the product dried in a vacuum oven for about 8-12 hrs to provide a target Compound A9 of Formula (I) wherein $R_2$ is $N^+(R_4R_5)$—$ZR_3$ and pharmaceutically acceptable anionic salt forms thereof.

Scheme B

The synthetic method provided by Scheme B, depending on the starting materials used or when certain reaction conditions are desired, is used as an alternative to Scheme A to prepare a compound of Formula (I).

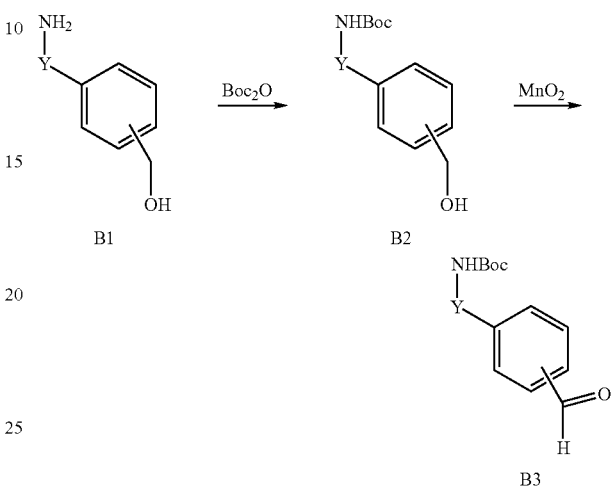

Di-t-butyl-dicarbonate is added in one portion at r.t. to a solution of Compound B1 (in a solvent such as CH₂Cl₂ and the like) and the solution is stirred for about 48 hrs. The reaction mixture is sequentially washed with an acidic solution (using a 10% citric acid solution and the like) and brine. The organic layer is separated, dried over Na₂SO₄ and filtered. The solvent is removed in vacuo to provide a protected Compound B2 that is used in the next step without further purification. A reagent (such as MnO₂ and the like) is added to a solution of Compound B2 (in a solvent such as chloroform and the like) to form a black suspension, which is stirred at r.t. for about 8-12 hrs, then filtered through a pad of celite. The solvent was evaporated in vacuo to provide Compound B3, which is used in the next step without further purification.

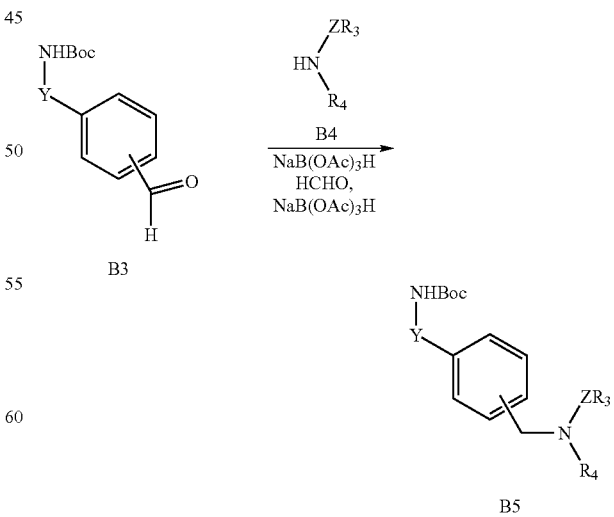

NaB(OAc)₃H is added to a mixture of Compound B3 and Compound B4 (in a solvent such as CH₂Cl₂ and the like) and the suspension is stirred at r.t. for a period of time. After the reaction is complete, an aldehyde (such as formaldehyde and the like) in aqueous solution is added, followed by NaB(OAc)$_3$ H added in one portion while the reaction vessel is cooled with ice. The reaction mixture is stirred at r.t. for about 12 hrs, then made basic (using a solution of 2N NaOH and the like) and extracted (with a solvent such as CH$_2$Cl$_2$ and the like). The organic layer is washed using brine, then separated and dried over Na$_2$SO$_4$. The drying agent is filtered and the solvent is removed in vacuo to yield a crude product which was purified by column chromatography (using an eluent ratio of about 4:1 and a solvent mixture such as CH$_2$Cl$_2$:MeOH and the like) to provide a disubstituted phenylamine Compound B5.

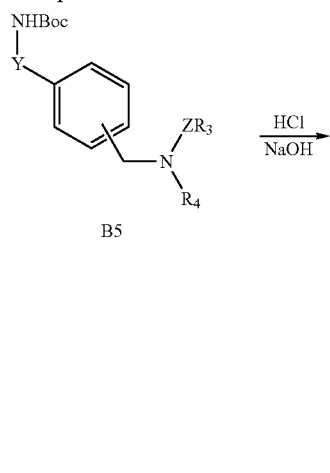

An HCl solution (in a solvent such as dioxane and the like) is added to a solution of Compound B5 (in a solvent such as CH$_2$Cl$_2$ and the like) and the mixture is stirred at r.t. for about 12 hrs. The solvent is removed and the residue is made basic (using a base such as a 2N NaOH solution) then extracted (with a solvent such as EtOAc). The organic layer is washed with brine, then separated and dried over Na$_2$SO$_4$. The drying agent is filtered and the solvent is removed in vacuo to provide a Compound B6.

Accordingly, using the procedure of Scheme A to provide additional compounds of the present invention, Compound B6 is used in place of Compound A4 and carried forward to provide a target compound of Formula (I) wherein X$_2$ is —CH$_2$— and pharmaceutically acceptable anionic salt forms thereof.

Scheme C

The synthetic method provided by Scheme C, depending on the starting materials used or when certain reaction conditions are desired, is used as an alternative to Scheme B to prepare a compound of Formula (I).

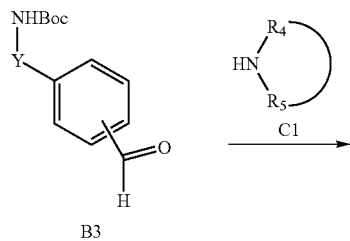

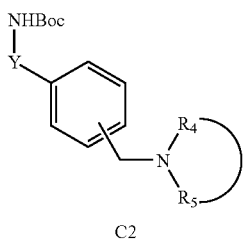

Using the procedure of Scheme B, Compound C1 is used in place of Compound B4 and coupled with Compound B3 to provide Compound C2.

Accordingly, using the procedure of Scheme B to provide additional compounds of the present invention, Compound C2 is used in place of Compound B5 and carried forward to provide a target compound of Formula (I) wherein X$_2$ is —CH$_2$— and R$_4$ and R$_5$ are taken together with the nitrogen atom of Formula-(I) to form a heterocyclyl ring and pharmaceutically acceptable anionic salt forms thereof.

Scheme D

The synthetic method provided by Scheme D, depending on the starting materials used or when certain reaction conditions are desired, is used as an alternative to Scheme A or B to prepare a compound of Formula (I).

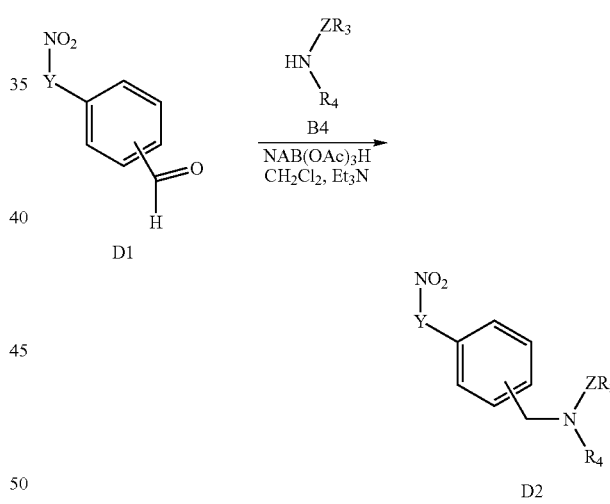

Using the procedure of Scheme B, Compound D1 and Compound B4 are coupled to provide Compound D2.

Accordingly, using the procedure of Scheme A to provide additional compounds of the present invention, Compound D2 is used in place of Compound A3 and carried forward to provide a target compound of Formula (I) wherein X$_2$ is —CH$_2$— and pharmaceutically acceptable anionic salt forms thereof.

Scheme E

The synthetic method provided by Scheme E, depending on the starting materials used or when certain reaction conditions are desired, is used to prepare a compound of Formula (I).

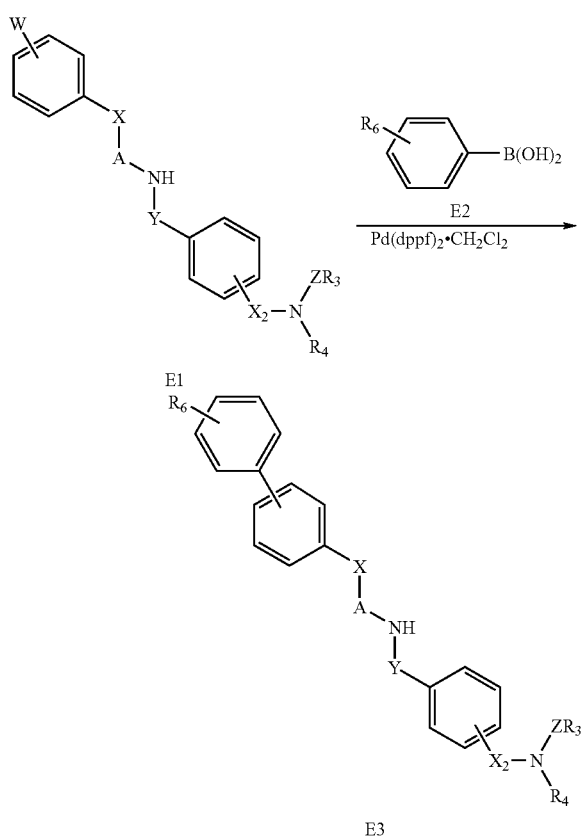

Compound E1 (wherein $W_1$ is a suitable leaving group such as a halogen atom) was reacted with Compound E2 to provide a further-substituted Compound E3, wherein $R_6$ is hydrogen, lower alkyl, $-(CH_2)_n-CF_3$, lower alkoxy, alkoxycarbonyl, cyano or halogen.

To provide additional compounds of the present invention, Compound J3 was used to replace Compound A6 and carried forward using the method of Scheme A to provide a target compound of Formula (I) and pharmaceutically acceptable anionic salt forms thereof.

Accordingly, using the procedure of Scheme A to provide additional compounds of the present invention, Compound E3 is used in place of Compound A6 and carried forward to provide a target compound of Formula (I) and pharmaceutically acceptable anionic salt forms thereof.

The invention is further defined by reference to the following examples, which are intended to be illustrative and not limiting.

EXAMPLE 1

[4-(3,4-dichloro-benzoylamino)-benzyl]-dimethyl-(tetrahydro-pyran-4-yl)-ammonium chloride (Cpd 17)

After cooling a mixture of 4-nitrobenzylamine hydrochloride Compound 1a, (22.12 mmol, 4.18 g) and tetrahydro-4H-pyran-4-one Compound 1b (22.25 mmol, 2.48 g) in $CH_2Cl_2$ (50 mL) to 0° C., $Et_3N$ (22.43 mmol, 3.13 mL) was added, followed by $NaB(OAc)_3H$ (31.0 mmol, 6.58 g). The resulting suspension was allowed to warm to r.t. with stirring overnight. An aliquot of the reaction mixture showed the formation of product (MS m/e 237, 100%). This portion of the procedure of Example 1 was adapted from Shiroshi, et al., *J. Med. Chem.*, 2000, 43, 2049.

An aqueous solution of formaldehyde (37% solution, 24.32 mmol, 1.98 mL) was combined with Compound 1c, followed by $NaB(OAc)_3H$ (31.0 mmol, 6.58 g) added in one portion under ice cooling. The reaction mixture was stirred at r.t. for 12 hrs, then made basic using a 2N NaOH solution and extracted with $CH_2Cl_2$. The organic layer was washed with brine, then separated and dried over $Na_2SO_4$. The drying agent was filtered and the solvent was removed in vacuo to yield methyl-(4-nitro-benzyl)-(tetrahydro-pyran-4-yl)-amine Compound 1c as a orange-yellow thick oil (5.58 g), which was used in the next step without further purification. This portion of the procedure of Example 1 was adapted from Hashimoto et al., *Org. Proc. R&D*, 2002, 6, 70. MS m/e 251 ($M^+H$, 100%); $^1H$ NMR (300 MHz, $CDCl_3$) δ 1.60-1.82 (m, 4H), 2.21 (s, 3H), 2.59-2.78 (m, 1H), 3.38 (dt, J=3.2 Hz, J=11.2 Hz, 2H), 3.68 (s, 2H), 4.02-4.10 (m, 2H), 7.50 (d, J=8.8 Hz, 2H), 8.17 (d, J=8.8 Hz, 2H).

$SnCl_2.2H_2O$ (71.2 mmol, 16.07 g) in conc. HCl (14 mL) was added in small portions to a solution of Compound 1c (22.12 mmol, 5.58 g) in THF (10 mL) at r.t. A mild exotherm was observed and the reaction mixture was placed in a water bath cooled with just enough ice to maintain r.t. The resulting yellow solution was stirred for 1 hr. TLC analysis [9:1 $CH_2Cl_2$:MeOH; $R_f$ 0.6 (Compound 1c) and $R_f$ 0.2 (Compound 1d)] showed a trace of starting material (Compound 1c). The round bottom flask containing the reaction mixture was then placed in a Warm-water bath for 30 min to allow the reaction to reach completion. The mixture was diluted with THF (50 mL) and water (30 mL) and made basic with 2N NaOH solution. The layers were separated and the aqueous layer was extracted with $Et_2O$ (2×75 mL). The combined organic layers were dried over $MgSO_4$, filtered and the solvent was removed in vacuo to obtain (4-amino-benzyl)-methyl-(tetrahydro-pyran-4-yl)-amine Compound 1d as a pale yellow solid. The solid was further dried by pressing it on a filter paper to obtain the product as an off-white powder (4.22 g, 86% yield over 3 steps). MS m/e 221 ($M^+H$, 100%); $^1H$ NMR (400 MHz, $CDCl_3$) δ 1.52-1.70 (m, 4H), 2.11 (s, 3H), 2.50-2.61 (m, 1H), 3.29 (dt, J=3.2 Hz, J=11.2 Hz, 2H), 3.42 (s, 2H), 3.54 (br, 2H), 3.91-3.98 (m, 2H), 6.58 (d, J=8.4 Hz, 2H), 7.10 (d, J=8.4 Hz, 2H).

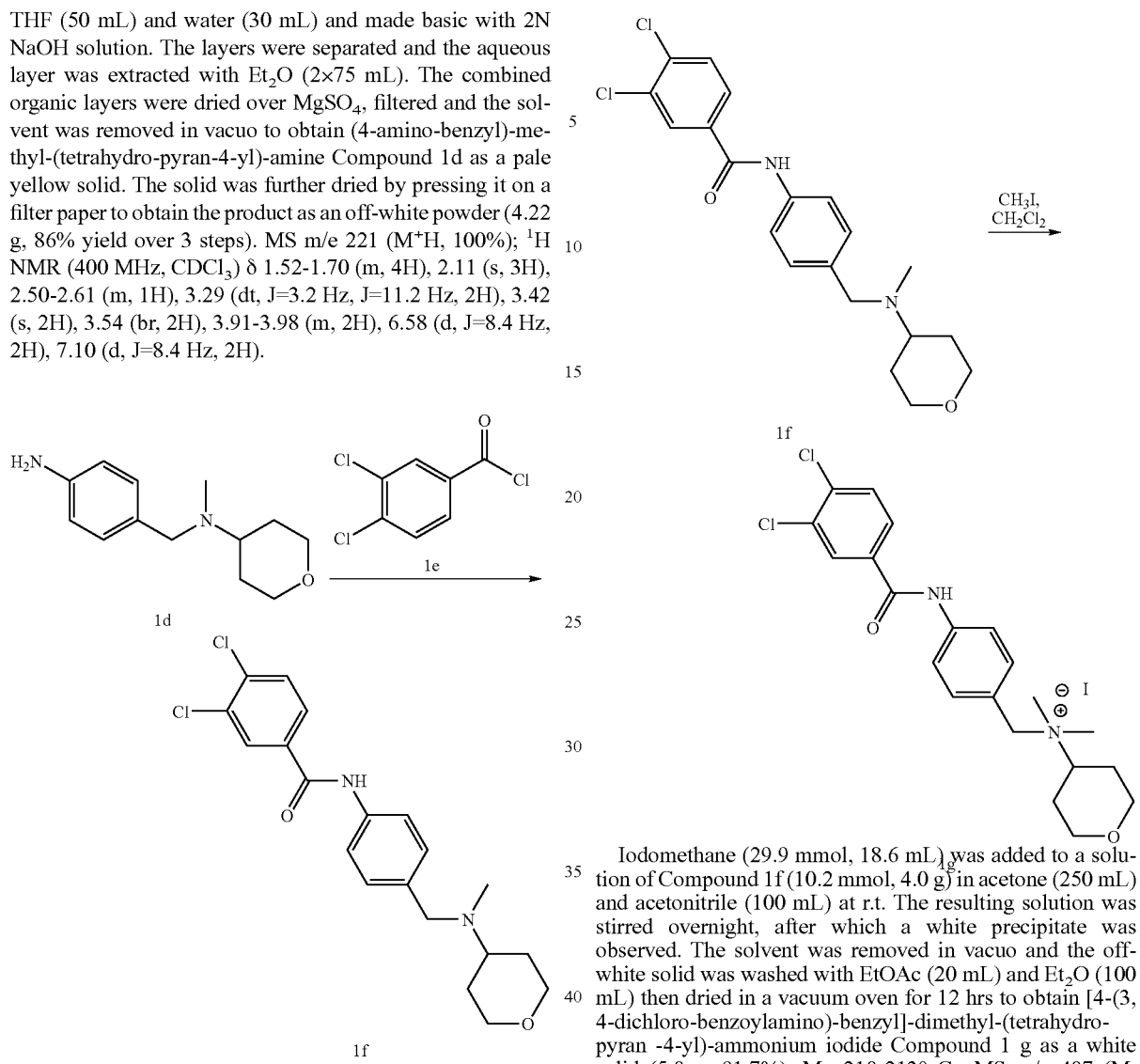

A solution of 3,4-dichlorobenzoyl chloride Compound 1e (14.4 mmol, 3.01 g) was added dropwise via a dropping funnel over 20 min to a solution of Compound 1d (13.64 mmol, 3.0 g) and $Et_3N$ (27.28 mmol, 3.8 mL) in THF (100 mL) at 0° C. The resulting suspension was allowed to warm to r.t. overnight, then made basic using a 2N NaOH solution and extracted with EtOAc (100 mL). The aqueous layer was extracted with EtOAc (2×50 mL). The organic layers were washed with brine, then dried over $MgSO_4$ and filtered. The solvent was removed in vacuo to yield 3,4-dichloro-N-(4-{[methyl-(tetrahydro-pyran-4-yl)-amino]-methyl}-phenyl)-benzamide Compound 1f as a yellow solid. The product was purified by flash column chromatography (15:1 EtOAc:MeOH to 6:1 EtOAc:MeOH) to yield a white powder (4.6 g, 86%). Mp 135-136° C.; MS m/e 393 ($M^+H$, 100%); $^1H$ NMR (300 MHz, $CDCl_3$) δ 1.65-1.83 (m, 4H), 2.21 (s, 3H), 2.58-2.61 (m, 1H), 3.38 (dt, J=3.1 Hz, J=11.0 Hz, 2H), 3.58 (s, 2H), 4.01-4.09 (m, 2H), 7.35 (d, J=8.4 Hz, 2H), 7.53-7.60 (m, 3H), 7.68-7.74 (m, 2H), 7.98 (d, J=3.0 Hz, 1H); Anal. Calcd. for $C_{20}H_{22}Cl_2N_2O_2$: C, 61.08; H, 5.64; N, 7.12; Cl, 18.03; Found C 61.09; H, 5.57; N, 6.93; Cl, 17.91.

Iodomethane (29.9 mmol, 18.6 mL) was added to a solution of Compound 1f (10.2 mmol, 4.0 g) in acetone (250 mL) and acetonitrile (100 mL) at r.t. The resulting solution was stirred overnight, after which a white precipitate was observed. The solvent was removed in vacuo and the off-white solid was washed with EtOAc (20 mL) and $Et_2O$ (100 mL) then dried in a vacuum oven for 12 hrs to obtain [4-(3,4-dichloro-benzoylamino)-benzyl]-dimethyl-(tetrahydro-pyran-4-yl)-ammonium iodide Compound 1g as a white solid (5.0 g, 91.7%). Mp 210-213° C.; MS m/e 407 (M, 100%); $^1H$ NMR (300 MHz, $CD_3OD$) δ 1.92-2.10 (m, 2H), 2.19-2.28 (m, 2H), 2.98 (s, 6H), 3.48 (t, J=11.4 Hz, 2H), 3.65-3.77 (m, 1H), 4.10-4.19 (m, 2H), 4.54 (s, 2H), 7.58 (d, J=8.4 Hz, 2H), 7.70 (d, J=8.4 Hz, 1H), 7.86-7.94 (m, 3H), 8.12 (d, J=2.1 Hz, 1H); Anal. Calcd. for $C_{21}H_{25}Cl_2N_2O_2$: C, 47.12; H, 4.71; N, 5.23, 123.71; Found C, 46.83; H, 4.57; N, 5.18, 123.38.

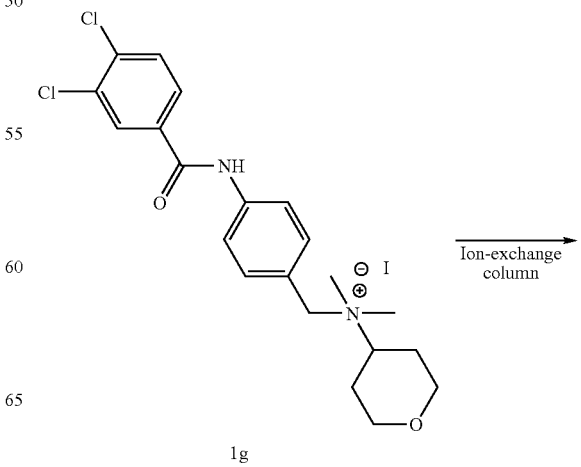

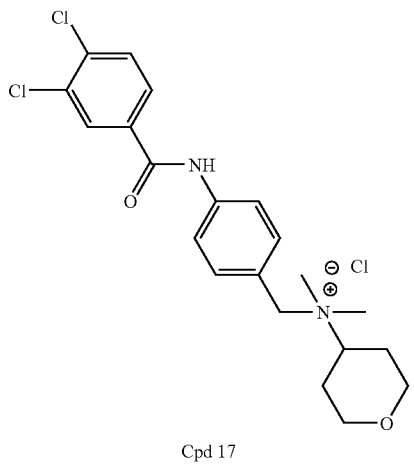

Cpd 17

A solution of Compound 1 g (5.0 g) in 1:1 mixture of MeOH/H$_2$O was passed through a column packed with ~300 g of anion-exchange resin (Bio-Rad, analytical grade anion exchange resin. AG 1-X8, 50-100 mesh, chloride form). The column was washed with MeOH and some acetone and Et$_2$O were added to the flask. The solvent was removed in vacuo and the product was dried in a vacuum oven overnight to provide Compound 17 as a white powder (3.9 g, 95%). Mp 227-232° C.; MS m/e 407 (M, 100%); $^1$H NMR (400 MHz, CD$_3$OD) δ 1.95-2.01 (m, 2H), 2.22-2.25 (m, 2H), 2.97 (s, 6H), 3.48 (t, J=11.7 Hz, 2H), 3.65-3.72 (m, 1H), 4.14-4.18 (m, 2H), 4.53 (s, 2H), 7.58 (d, J=8.6 Hz, 2H), 7.70 (d, J=8.4 Hz, 1H), 7.86-7.92 (m, 3H), 8.12 (d, J=2.1 Hz, 1H); Anal. Calcd. for C$_{21}$H$_{25}$Cl$_3$N$_2$O$_2$: C, 56.83; H, 5.68; N, 6.31; Cl, 23.97; Found C, 56.93; H, 5.72; N, 6.02; Cl, 23.67 (% I was found to be <0.1%).

Using the procedure of Example 1 and known appropriate reagents and starting materials, other compounds of the present invention may be prepared including, (MS: Mass Spec data as MS m/e M$^+$H):

| Cpd | Name | MS |
|---|---|---|
| 6 | (4-benzoylamino-benzyl)-dimethyl-(tetrahydro-pyran-4-yl)-ammonium iodide | 429 |
| 9 | [4-(2,3-dichloro-benzoylamino)-benzyl]-dimethyl-(tetrahydro-pyran-4-yl)-ammonium iodide | 407 |
| 10 | [4-(2,4-dichloro-benzoylamino)-benzyl]-dimethyl-(tetrahydro-pyran-4-yl)-ammonium iodide | 407 |
| 11 | [4-(2,5-dichloro-benzoylamino)-benzyl]-dimethyl-(tetrahydro-pyran-4-yl)-ammonium iodide | 407 |
| 12 | [4-(2,6-dichloro-benzoylamino)-benzyl]-dimethyl-(tetrahydro-pyran-4-yl)-ammonium iodide | 407 |
| 13 | [4-(2-chloro-benzoylamino)-benzyl]-dimethyl-(tetrahydro-pyran-4-yl)-ammonium iodide | 373 |
| 14 | bicyclo[2.2.1]hept-2-yl-[4-(3,4-dichloro-benzoylamino)-benzyl]-dimethyl-ammonium iodide | 417 |
| 19 | [4-(3,4-dichloro-benzoylamino)-benzyl]-dimethyl-(tetrahydro-thien-3-yl)-ammonium iodide | 409 |
| 20 | [4-(3,4-dichloro-benzoylamino)-benzyl]-dimethyl-(tetrahydro-thiopyran-4-yl)-ammonium iodide | 423 |
| 21 | [4-(3,4-dichloro-benzoylamino)-benzyl]-ethyl-methyl-(tetrahydro-pyran-4-yl)-ammonium iodide | 421 |
| 22 | [4-(3,4-dichloro-benzoylamino)-benzyl]-methyl-propyl-(tetrahydro-pyran-4-yl)-ammonium iodide | 435 |
| 23 | [4-(3,5-dichloro-benzoylamino)-benzyl]-dimethyl-(tetrahydro-pyran-4-yl)-ammonium iodide | 407 |
| 24 | [4-(3-bromo-benzoylamino)-benzyl]-dimethyl-(tetrahydro-pyran-4-yl)-ammonium iodide | 417 |
| 25 | [4-(3-chloro-2-methyl-benzoylamino)-benzyl]-dimethyl-(tetrahydro-pyran-4-yl)-ammonium iodide | 387 |
| 26 | [4-(3-chloro-4-fluoro-benzoylamino)-benzyl]-dimethyl-(tetrahydro-pyran-4-yl)-ammonium iodide | 391 |
| 27 | [4-(3-chloro-4-methoxy-benzoylamino)-benzyl]-dimethyl-(tetrahydro-pyran-4-yl)-ammonium iodide | 403 |
| 28 | [4-(3-chloro-4-methyl-benzoylamino)-benzyl]-dimethyl-(tetrahydro-pyran-4-yl)-ammonium iodide | 387 |
| 29 | [4-(3-chloro-benzoylamino)-benzyl]-dimethyl-(tetrahydro-pyran-4-yl)-ammonium iodide | 359 |
| 30 | [4-(3-cyano-benzoylamino)-benzyl]-dimethyl-(tetrahydro-pyran-4-yl)-ammonium iodide | 364 |
| 31 | [4-(3-methoxy-benzoylamino)-benzyl]-dimethyl-(tetrahydro-pyran-4-yl)-ammonium iodide | 369 |
| 32 | [4-(4-chloro-2-methyl-benzoylamino)-benzyl]-dimethyl-(tetrahydro-pyran-4-yl)-ammonium iodide | 387 |
| 34 | [4-(4-chloro-benzoylamino)-benzyl]-dimethyl-(tetrahydro-pyran-4-yl)-ammonium iodide | 373 |
| 35 | [4-(5-chloro-2-methyl-benzoylamino)-benzyl]-dimethyl-(tetrahydro-pyran-4-yl)-ammonium iodide | 387 |
| 40 | {4-[3-(3,4-dichloro-phenyl)-acryloylamino]-benzyl}-dimethyl-(tetrahydro-pyran-4-yl)-ammonium iodide | 419 |

-continued

| Cpd | Name | MS |
|---|---|---|
| 41 | {4-[3-(3,4-dichloro-phenyl)-acryloylamino]-benzyl}-dimethyl-(tetrahydro-thiopyran-4-yl)-ammonium iodide | 449 |
| 42 | {4-[3-(3,5-difluoro-phenyl)-acryloylamino]-benzyl}-dimethyl-(tetrahydro-pyran-4-yl)-ammonium iodide | 401 |
| 43 | {4-[3-(3-bromo-phenyl)-acryloylamino]-benzyl}-dimethyl-(tetrahydro-pyran-4-yl)-ammonium iodide | 443 |
| 44 | {4-[3-(3-bromo-phenyl)-acryloylamino]-benzyl}-dimethyl-(tetrahydro-thiopyran-4-yl)-ammonium iodide | 459 |
| 45 | {4-[3-(3-chloro-phenyl)-acryloylamino]-benzyl}-dimethyl-(tetrahydro-pyran-4-yl)-ammonium iodide | 399 |
| 46 | {4-[3-(3-fluoro-phenyl)-acryloylamino]-benzyl}-dimethyl-(tetrahydro-pyran-4-yl)-ammonium iodide | 383 |
| 47 | {4-[3-(4-bromo-phenyl)-acryloylamino]-benzyl}-dimethyl-(tetrahydro-pyran-4-yl)-ammonium iodide | 443 |
| 50 | 1-[4-(3,4-dichloro-benzoylamino)-benzyl]-1-methyl-piperidinium iodide | 377 |
| 51 | 1-[4-(3,4-dichloro-benzoylamino)-benzyl]-1-methyl-pyrrolidinium iodide | 363 |
| 54 | 1-{4-[3-(3,4-dichloro-phenyl)-acryloylamino]-benzyl}-4-(2-methoxy-phenyl)-1-methyl-piperazin-1-ium iodide | 510 |
| 55 | 1-{4-[3-(3-bromo-phenyl)-acryloylamino]-benzyl}-1-methyl-piperidinium iodide | 413 |
| 57 | 1-methyl-1-{4-[3-(3-trifluoromethyl-phenyl)-acryloylamino]-benzyl}-piperidinium iodide | 403 |
| 59 | 4-[4-(3,4-dichloro-benzoylamino)-benzyl]-4-methyl-morpholin-4-ium iodide | 379 |
| 60 | 4-{4-[3-(3,4-dichloro-phenyl)-acryloylamino]-benzyl}-4-methyl-morpholin-4-ium iodide | 405 |
| 61 | 4-{4-[3-(3-bromo-phenyl)-acryloylamino]-benzyl}-4-methyl-morpholin-4-ium iodide | 415 |
| 63 | allyl-{4-[3-(3-bromo-phenyl)-acryloylamino]-benzyl}-methyl-(tetrahydro-thiopyran-4-yl)-ammonium iodide | 487 |
| 66 | dimethyl-(tetrahydro-pyran-4-yl)-[4-(3-m-tolyl-acryloylamino)-benzyl]-ammonium iodide | 379 |
| 67 | dimethyl-(tetrahydro-pyran-4-yl)-[4-(3-trifluoromethyl-benzoylamino)-benzyl]-ammonium iodide | 407 |
| 68 | dimethyl-(tetrahydro-pyran-4-yl)-{4-[3-(3-trifluoromethyl-phenyl)-acryloylamino]-benzyl}-ammonium iodide | 433 |
| 69 | dimethyl-[4-(3-methyl-benzoylamino)-benzyl]-(tetrahydro-pyran-4-yl)-ammonium iodide | 353 |
| 70 | cycloheptyl-[4-(3,4-dichloro-benzoylamino)-benzyl]-dimethyl-ammonium iodide | 419 |
| 71 | cyclohexyl-{4-[3-(3,4-dichloro-phenyl)-acryloylamino]-benzyl}-dimethyl-ammonium iodide | 431 |
| 72 | {4-[3-(3-bromo-phenyl)-acryloylamino]-benzyl}-cyclohexyl-dimethyl-ammonium iodide | 443 |
| 74 | cyclohexyl-dimethyl-[4-(3-trifluoromethyl-benzoylamino)-benzyl]-ammonium iodide | 405 |
| 75 | cyclohexyl-[4-(3,4-dichloro-benzoylamino)-benzyl]-dimethyl-ammonium iodide | 405 |
| 76 | [4-(3-chloro-4-fluoro-benzoylamino)-benzyl]-cyclohexyl-dimethyl-ammonium iodide | 389 |
| 77 | cyclohexyl-[4-(2,3-dichloro-benzoylamino)-benzyl]-dimethyl-ammonium iodide | 405 |
| 78 | cyclohexyl-[4-(2,6-dichloro-benzoylamino)-benzyl]-dimethyl-ammonium iodide | 405 |
| 79 | [4-(3-chloro-4-methoxy-benzoylamino)-benzyl]-cyclohexyl-dimethyl-ammonium iodide | 401 |
| 80 | [4-(3-chloro-4-methyl-benzoylamino)-benzyl]-cyclohexyl-dimethyl-ammonium iodide | 385 |
| 81 | cyclohexyl-[4-(2,5-dichloro-benzoylamino)-benzyl]-dimethyl-ammonium iodide | 405 |
| 82 | cyclopentyl-[4-(3,4-dichloro-benzoylamino)-benzyl]-dimethyl-ammonium iodide | 391 |
| 89 | dimethyl-{4-[(naphthalene-1-carbonyl)-amino]-benzyl}-(tetrahydro-pyran-4-yl)-ammonium iodide | 389 |
| 90 | dimethyl-{4-[(naphthalene-2-carbonyl)-amino]-benzyl}-(tetrahydro-pyran-4-yl)-ammonium iodide | 389 |
| 91 | ethyl-methyl-{4-[(naphthalene-2-carbonyl)-amino]-benzyl}-(tetrahydro-pyran-4-yl)-ammonium iodide | 403 |
| 92 | methyl-{4-[(naphthalene-2-carbonyl)-amino]-benzyl}-propyl-(tetrahydro-pyran-4-yl)-ammonium iodide | 417 |
| 93 | {4-[(7-bromo-naphthalene-2-carbonyl)-amino]-benzyl}-dimethyl-(tetrahydro-pyran-4-yl)-ammonium iodide | 467 |
| 94 | {4-[(7-bromo-naphthalene-2-carbonyl)-amino]-benzyl}-cyclohexyl-dimethyl-ammonium iodide | 465 |
| 151 | dimethyl-{4-[(2-methyl-5-phenyl-furan-3-carbonyl)-amino]-benzyl}-(tetrahydro-pyran-4-yl)-ammonium iodide | 419 |
| 152 | {4-[(benzofuran-2-carbonyl)-amino]-benzyl}-dimethyl-(tetrahydro-pyran-4-yl)-ammonium iodide | 379 |

-continued

| Cpd | Name | MS |
|---|---|---|
| 155 | {4-[(5-chloro-benzofuran-2-carbonyl)-amino]-benzyl}-dimethyl-(tetrahydro-pyran-4-yl)-ammonium iodide | 413 |
| 156 | {4-[(5-chloro-benzofuran-2-carbonyl)-amino]-benzyl}-cyclohexyl-dimethyl-ammonium iodide | 411 |
| 157 | {4-[(benzofuran-2-carbonyl)-amino]-benzyl}-cyclohexyl-dimethyl-ammonium iodide | 437 |
| 172 | {4-[(5-bromo-pyridine-3-carbonyl)-amino]-benzyl}-dimethyl-(tetrahydro-pyran-4-yl)-ammonium iodide | 420 |
| 173 | {4-[(2-chloro-pyridine-4-carbonyl)-amino]-benzyl}-dimethyl-(tetrahydro-pyran-4-yl)-ammonium iodide | 374 |

EXAMPLE 2

{2-[4-(3,4-dichloro-benzoylamino)-phenyl]-ethyl}-dimethyl-(tetrahydro-pyran -4-yl)-ammonium iodide (Cpd 36)

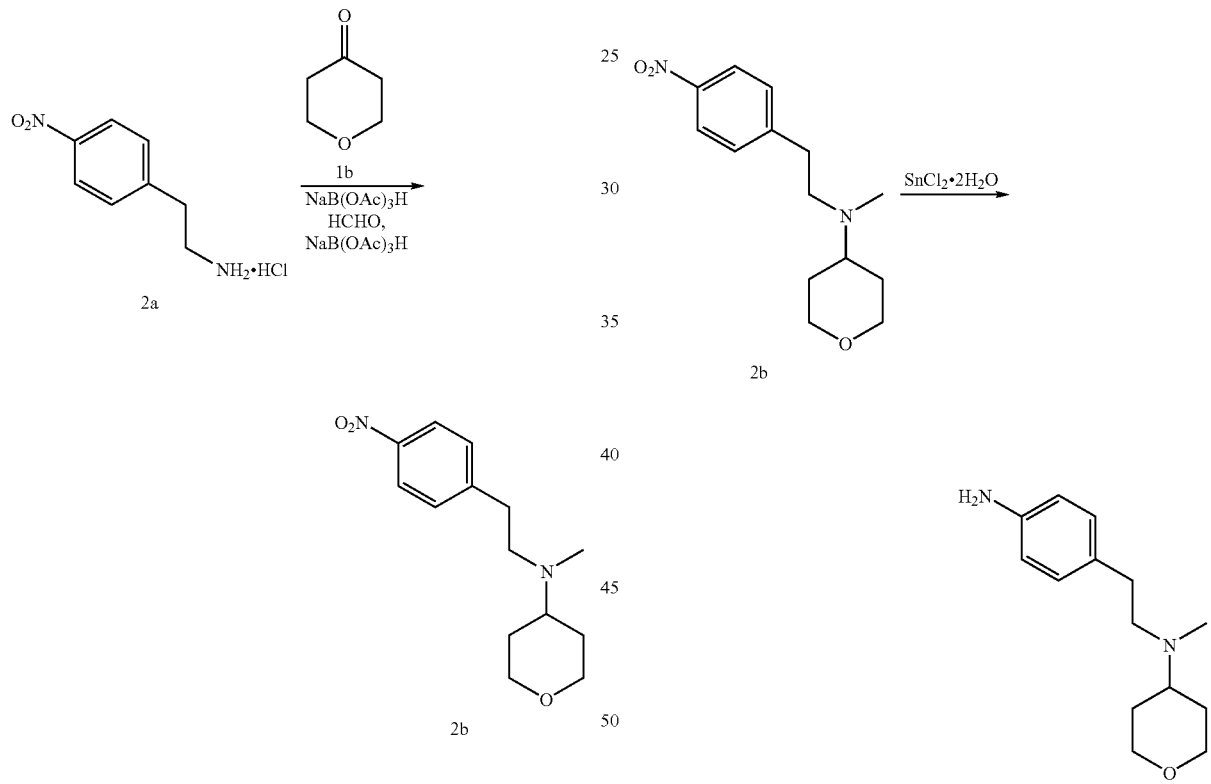

NaB(OAc)$_3$H (2.33 mmol, 0.5 g) was added to a mixture of 2-(4-nitro-phenyl)-ethylamine Compound 2a (2.25 mmol, 0.45 g) and tetrahydro-4H-pyran-4-one Compound 1b (2.25 mmol, 0.21 mL) and Et$_3$N (2.25 mmol, 0.31 mL) in CH$_2$Cl$_2$ (25 mL). The resulting suspension was stirred at r.t. for 12 hrs. An aliquot of the reaction mixture showed the formation of product (MS m/e 251, 100%).

An aqueous solution of formaldehyde (37% solution, 8.6 mmol, 0.7 mL) was added, followed by NaB(OAc)$_3$H (2.33 mmol, 0.5 g) and the reaction mixture was stirred at r.t. for 12 hrs. The mixture was made basic using a 2N NaOH solution, extracted with CH$_2$Cl$_2$ and the organic layer was washed with brine, then separated and dried over Na$_2$SO$_4$. The drying agent was filtered and the solvent was removed in vacuo to yield methyl-[2-(4-nitro-phenyl)-ethyl]-(tetrahydro-pyran-4-yl)-amine Compound 2b as a yellow oil. The product was purified by flash column chromatography (10:1 CH$_2$Cl$_2$:MeOH; R$_f$ 0.8) to yield a yellow oil (0.58 g, 97%). MS m/e 265 (M$^+$H, 100%).

SnCl$_2$.2H$_2$O (10.0 mmol, 2.25 g) was added to a solution of Compound 2b (2.19 mmol, 0.58 g) in EtOH (10 mL) at r.t. A mild exotherm was observed. The resulting yellow solution was stirred for 12 hrs and the solvent was removed in vacuo. The residue was made basic using a 2N NaOH solution and the aqueous layer was extracted with CH$_2$Cl$_2$ (2×25 mL). The combined organic layers were dried over Na$_2$SO$_4$ and filtered, then the solvent was removed in vacuo to obtain [2-(4-amino-phenyl)-ethyl]-methyl-(tetrahydro-pyran-4-yl)-amine Compound 2c as an orange-yellow oil (0.4 g) used in the next step without purification. MS m/e 235 (M$^+$H, 100%).

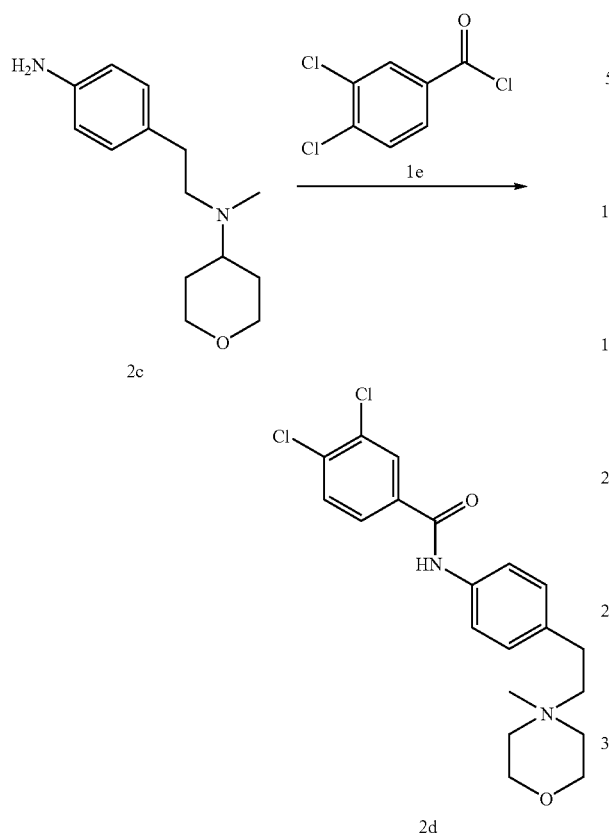

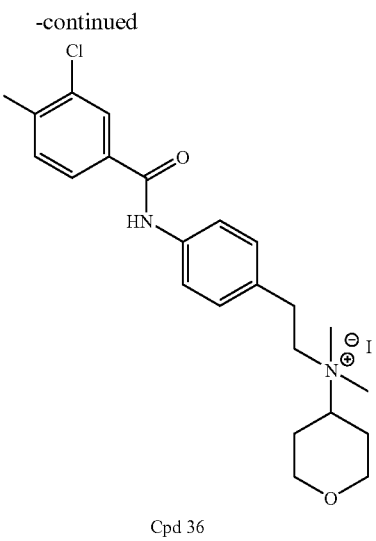

A solution of 3,4-dichlorobenzoyl chloride Compound 1e (0.25 mmol, 0.06 g) in THF (1 mL) was added dropwise over 2 min to a solution of Compound 2c (0.2 mmol, 0.05 g) and Et$_3$N (0.4 mmol, 0.06 mL) in THF (4 mL) at 0° C. The resulting suspension was allowed to warm to r.t. overnight, then made basic with a 2N NaOH-solution and extracted with EtOAc (10 mL). The aqueous layer was extracted with EtOAc (2×10 mL). The organic layers were washed with brine, then dried over Na$_2$SO$_4$ and filtered. The solvent was removed in vacuo to yield 3,4-dichloro-N-(4-{2-[methyl-(tetrahydro-pyran-4-yl)-amino]-ethyl)}-phenyl)-benzamide Compound 2d as a yellow solid. The product was purified by preparative TLC (10:1 EtOAc:MeOH) (0.06 g, 73%). MS m/e 407 (M$^+$H, 100%);

Iodomethane (0.5 mL, excess) was added to a solution of Compound 2d (0.07 mmol, 0.03 g) in acetone (1.0 mL) and acetonitrile (1.0 mL) at r.t. The resulting solution was stirred overnight, after which a yellow precipitate was observed. The solvent was removed in vacuo and the off-white solid was washed with Et$_2$O (2×5 mL) to provide Compound 36 as a pale yellow solid (0.03 g, 82%). MS m/e 548 (M, 100%).

Using the procedure of Example 2 and known appropriate reagents and starting materials, other compounds of the present invention may be prepared including, (MS: Mass Spec data as MS m/e M$^+$H):

| Cpd | Name | MS |
|---|---|---|
| 37 | {2-[4-(3-bromo-benzoylamino)-phenyl]-ethyl}-dimethyl-(tetrahydro-pyran-4-yl)-ammonium iodide | 431 |

EXAMPLE 3 dimethyl-(tetrahydro-pyran-4-yl)-(4-{[3-(3-trifluoromethyl-phenyl)-acryloylamino]-methyl}-benzyl)-ammonium iodide (Cpd 64)

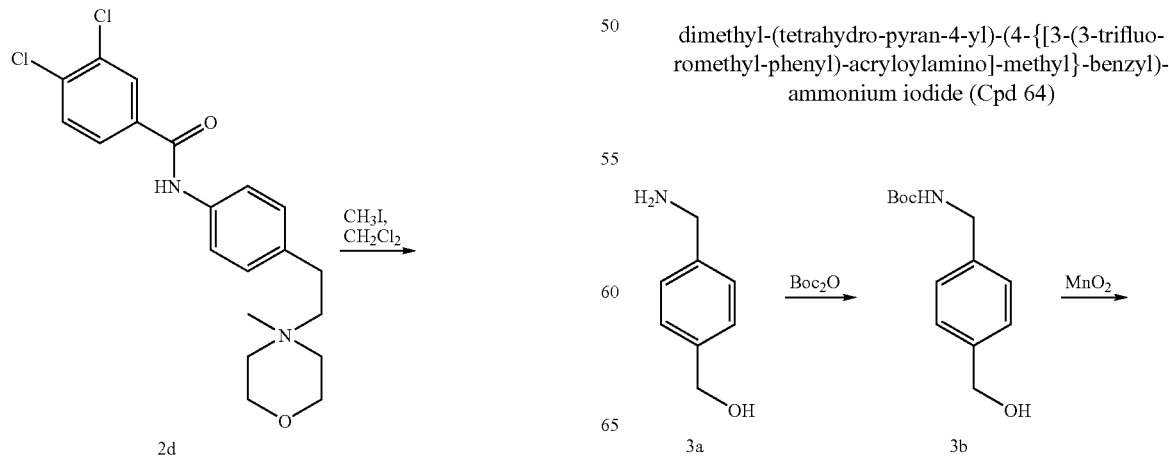

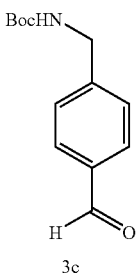

Boc₂O was added in one portion at r.t. to a solution of (4-aminomethyl-phenyl)-methanol Compound 3a (21.2 mmol, 2.9 g) in CH₂Cl₂ (100 mL). The resulting solution was stirred for 48 h, then washed with a 10% citric acid solution (50 mL) followed by brine. The organic-layer was separated, then dried over Na₂SO₄ and filtered. The solvent was removed in vacuo to obtain (4-hydroxymethyl-benzyl)-carbamic acid tert-butyl ester Compound 3b as a white solid (5.2 g, 99% yield), which was used in the next step without further purification.

MnO₂ (9.6 g) was added to a solution of Compound 3b (21.2 mmol, 5.2 g) in chloroform (60 mL), forming a black suspension that was stirred at r.t. overnight then filtered through a pad of celite. The solvent was evaporated in vacuo to obtain (4-formyl-benzyl)-carbamic acid tert-butyl ester Compound 3c as a white solid (4.3 g, 87% yield), which was used in the next step without purification.

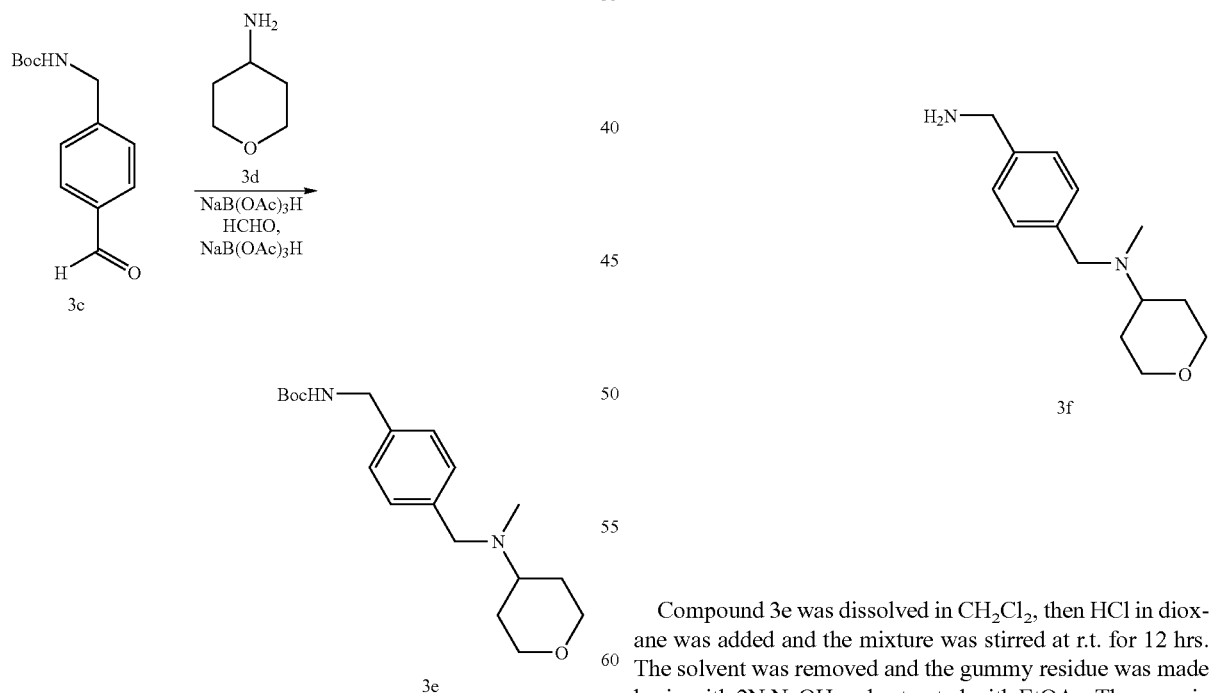

NaB(OAc)₃H (2.8 mmol, 0.58 g) was added to a mixture of Compound 3c (2.6 mmol, 0.6 g) and tetrahydro-pyran-4-ylamine Compound 3d (2.6 mmol, 0.26 g) in CH₂Cl₂ (25 mL) and the resulting suspension was stirred at r.t. An aliquot of the reaction mixture showed the formation of product (MS m/e 321; 100%). An aqueous solution of formaldehyde (37% solution, 8.6 mmol, 0.7 mL) was added to the reaction mixture, followed by NaB(OAc)₃H (2.8 mmol, 0.58 g) added in one portion under ice cooling. The reaction mixture was stirred at r.t. for about 2 h, then made basic with a 2N NaOH solution and extracted with CH₂Cl₂. The organic layer was washed with brine, then separated and dried over Na₂SO₄. The drying agent was filtered and the solvent was removed in vacuo to yield (4-{[methyl-(tetrahydro-pyran-4-yl)-amino]-methyl}-benzyl)-carbamic acid tert-butyl ester Compound 3e as a pale yellow oil. MS m/e 235 (M⁺H, 100%). The product was purified by column chromatography (4:1 CH₂Cl₂:MeOH) to yield a colorless oil (0.52 g, 59% yield).

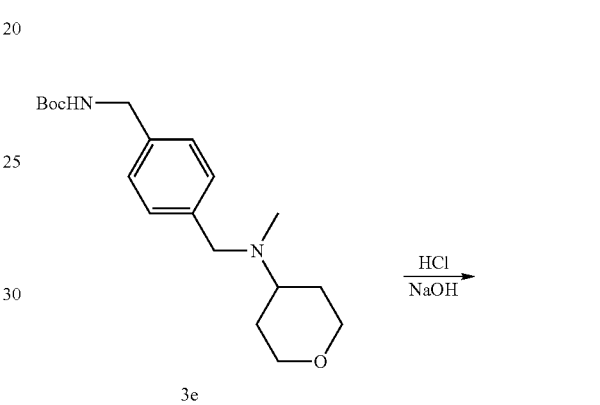

Compound 3e was dissolved in CH₂Cl₂, then HCl in dioxane was added and the mixture was stirred at r.t. for 12 hrs. The solvent was removed and the gummy residue was made basic with 2N NaOH and extracted with EtOAc. The organic layer was washed with brine, then separated and dried over Na₂SO₄. The drying agent was filtered and the solvent was removed in vacuo to obtain (4-aminomethyl-benzyl)-methyl-(tetrahydro-pyran-4-yl)-amine Compound 3f as a pale yellow oil (0.3 g, 83% yield). MS m/e 235 (M⁺H, 100%).

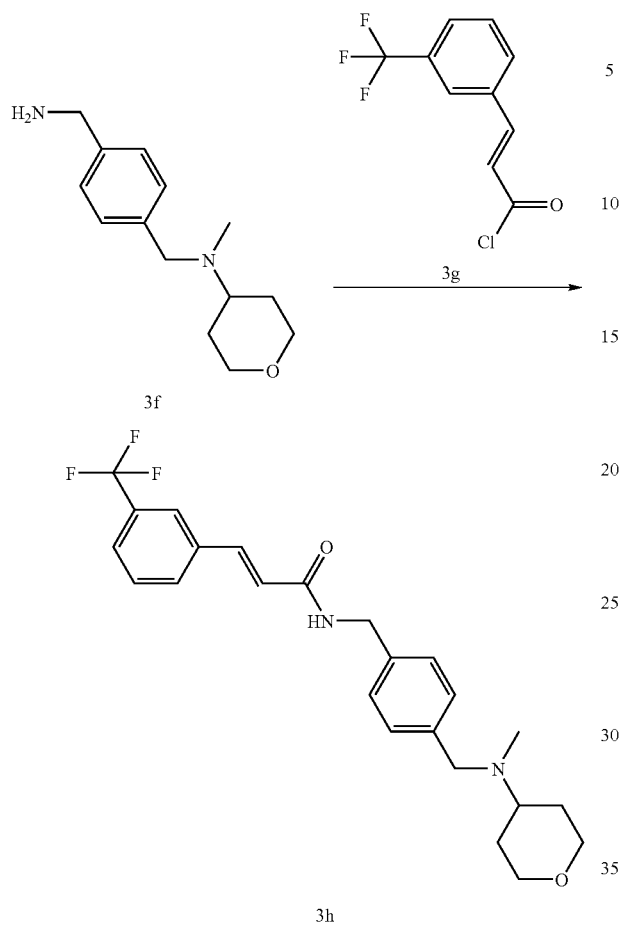

3f

3h

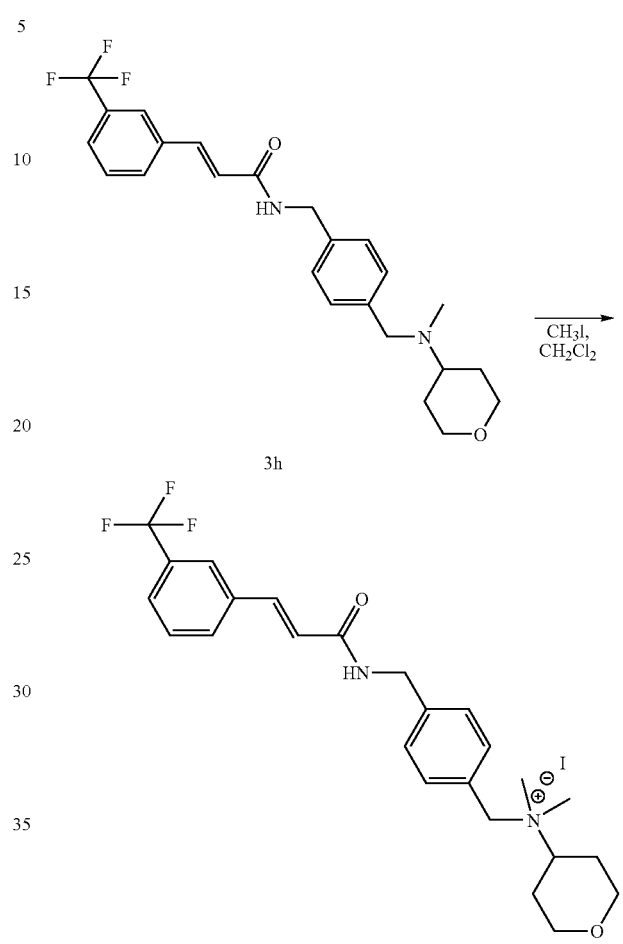

3h

Cpd 64 thyl}-benzyl)-3-(3-trifluoromethyl-phenyl)-acrylamide Compound 3h (0.06 g, 49% yield). MS m/e 433 (M+H, 100%).

A solution of 3-(3-trifluoromethyl-phenyl)-acryloyl chloride Compound 3g (0.3 mmol, 0.07 g) in THF (2 mL) was added dropwise to a solution of Compound 3f (0.2 mmol, 0.05 g) and Et₃N (0.8 mmol, 0.14 mL) in THF (10 mL) at 0° C. The resulting suspension was allowed to warm to r.t. overnight. The reaction mixture was made basic with a 2N NaOH solution and extracted with EtOAc (25 mL). The aqueous layer was extracted with EtOAc (2×10 mL) and the organic layers were washed with brine, then dried over Na₂SO₄ and filtered. The solvent was removed in vacuo to yield a yellow solid (with methane) as the product. The crude product was purified by preparative TLC (9:1 EtOAc:MeOH, Rf=0.2) to yield N-(4-{[methyl-(tetrahydro-pyran-4-yl)-amino]-me- MeI (0.08 mL, 1.28 mmol) was added dropwise to a solution of Compound 3h (0.07 mmol, 0.03 g) in a mixture of acetone:acetonitrile (2 mL). The resulting solution was stirred at r.t. for 24 h to provide a residue. The residue was washed with ether (2×1 mL) and dried under a high vacuum to provide Compound 64 (0.04 g, 93% yield) as an iodide salt. MS m/e 584 (M+H, 100%).

Using the procedure of Example 3 and the appropriate known reagents and starting materials, other compounds of the invention may be prepared including, (MS: Mass Spec data as MS m/e M+H),

| Cpd | Name | MS |
|---|---|---|
| 1 | (4-{[3-(3-bromo-phenyl)-acryloylamino]-methyl}-benzyl)-cyclohexyl-dimethyl-ammonium iodide | 455 |
| 2 | {4-[(3-bromo-benzoylamino)-methyl]-benzyl}-cyclohexyl-dimethyl-ammonium iodide | 429 |
| 3 | cyclohexyl-dimethyl-{4-[(3-trifluoromethyl-benzoylamino)-methyl]-benzyl}-ammonium iodide | 419 |
| 4 | (4-{[3-(3,4-dichloro-phenyl)-acryloylamino]-methyl}-benzyl)-dimethyl-(tetrahydro-pyran-4-yl)-ammonium iodide | 447 |
| 5 | (4-{[3-(3-bromo-phenyl)-acryloylamino]-methyl}-benzyl)-dimethyl-(tetrahydro-pyran-4-yl)-ammonium iodide | 457 |

-continued

| Cpd | Name | MS |
|---|---|---|
| 39 | {4-[(3,4-dichloro-benzoylamino)-methyl]-benzyl}-dimethyl-(tetrahydro-pyran-4-yl)-ammonium iodide | 421 |
| 48 | 1-(4-{[3-(3,4-dichloro-phenyl)-acryloylamino]-methyl}-benzyl)-1-methyl-piperidinium iodide | 417 |
| 49 | 1-(4-{[3-(3-bromo-phenyl)-acryloylamino]-methyl}-benzyl)-1-methyl-piperidinium iodide | 427 |
| 58 | 4-(4-{[3-(3,4-dichloro-phenyl)-acryloylamino]-methyl}-benzyl)-4-methyl-morpholin-4-ium iodide | 419 |
| 149 | dimethyl-(4-{[(2-methyl-5-phenyl-furan-3-carbonyl)-amino]-methyl}-benzyl)-(tetrahydro-pyran-4-yl)-ammonium iodide | 433 |
| 150 | [4-({[5-(4-chloro-phenyl)-2-methyl-furan-3-carbonyl]-amino}-methyl)-benzyl]-dimethyl-(tetrahydro-pyran-4-yl)-ammonium iodide | 467 |
| 153 | (4-{[5-(4-chloro-phenyl)-2-trifluoromethyl-furan-3-carbonyl]-amino}-benzyl)-dimethyl-(tetrahydro-pyran-4-yl)-ammonium iodide | 507 |
| 154 | (4-{[5-(4-chloro-phenyl)-2-trifluoromethyl-furan-3-carbonyl]-amino}-benzyl)-cyclohexyl-dimethyl-ammonium iodide | 506 |

EXAMPLE 4

[4-(3,4-dichloro-benzoylamino)-benzyl]-dimethyl-(tetrahydro-pyran-4-ylmethyl)-ammonium iodide (Cpd 18)

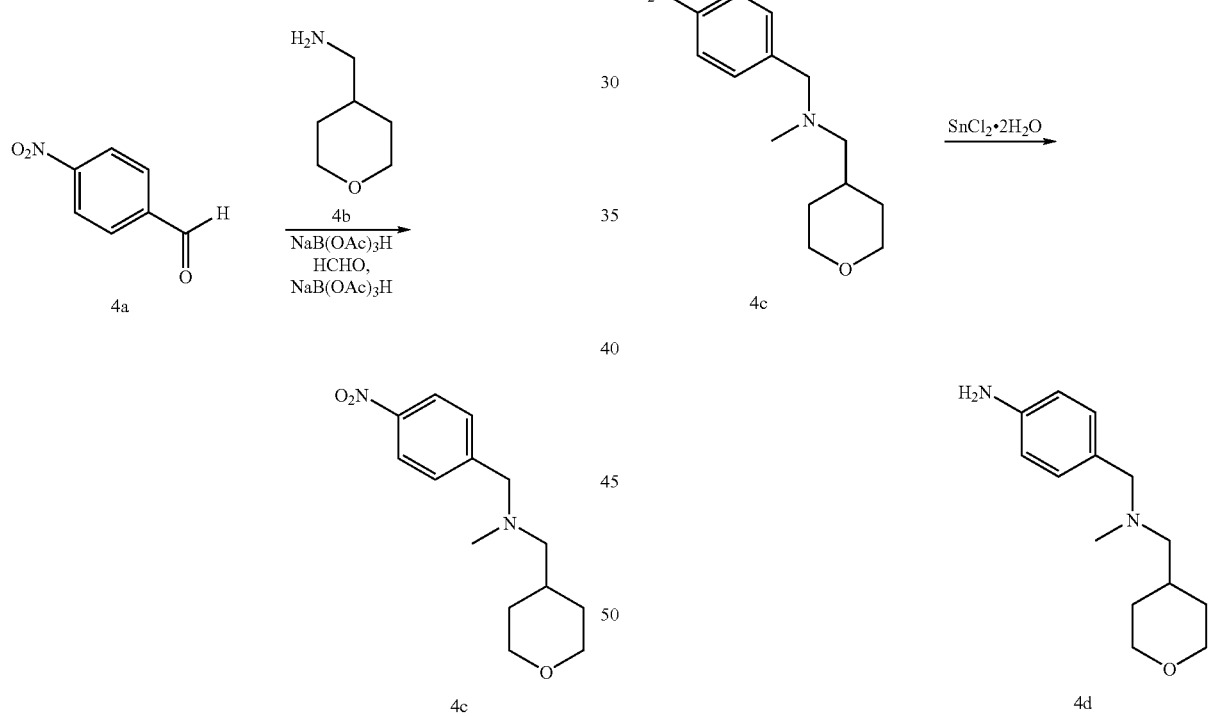

NaB(OAc)$_3$H (3.5 mmol, 0.75 g) was added to a mixture of 4-nitro-benzaldehyde Compound 4a (2.8 mmol, 0.42 g), (tetrahydro-pyran-4-yl)-methylamine Compound 4b (3.0 mmol, 0.35 g) and glacial acetic acid (3 drops) in CH$_2$Cl$_2$ (50 mL) and the resulting suspension was stirred at r.t. overnight. An aliquot of the reaction mixture showed the formation of product (MS m/e 251; 100%). An aqueous solution of formaldehyde (37% solution, 9.6 mmol, 0.8 mL) was added, followed by NaB(OAc)$_3$H (3.5 mmol, 0.75 g). The reaction mixture was stirred at r.t. for 2 h, then made basic with a 2N NaOH solution and extracted with CH$_2$Cl$_2$. The organic layer was washed with brine, then separated and dried over Na$_2$SO$_4$. The drying agent was filtered and the solvent was removed in vacuo to yield methyl-(4-nitro-benzyl)-(tetrahydro-pyran-4-ylmethyl)-amine Compound 4c as yellow oil (0.63 g, 85% yield). MS m/e 265 (M$^+$H, 100%).

SnCl$_2$.2H$_2$O (1.78 mmol, 0.4 g) was added to a solution of Compound 4c (1.13 mmol, 0.3 g) in EtOH (20 mL) at r.t. The resulting yellow solution was stirred for 2 days then the solvent was removed in vacuo. The residue was made basic with a 2N NaOH solution and the aqueous layer was extracted with CH$_2$Cl$_2$ (2×25 mL). The combined organic layers were dried over Na$_2$SO$_4$ and filtered, then the solvent was removed in vacuo to obtain 4-{[methyl-(tetrahydro-pyran -4-ylmethyl)-amino]-methyl}-phenylamine Compound 4d as an orange-yellow oil (0.25 g, 94%) used in the next step without purification. MS m/e 235 (M$^+$H, 100%).

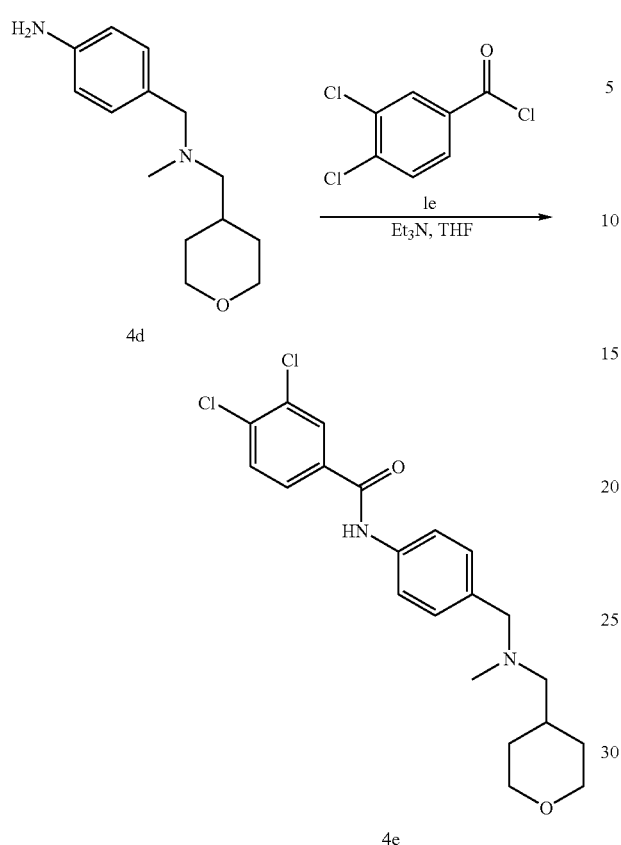

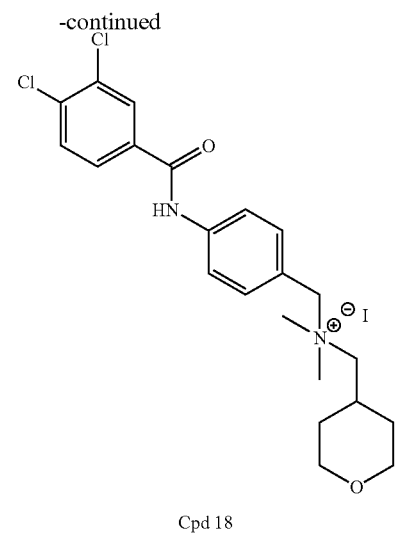

A solution of 3,4-dichlorobenzoyl chloride Compound 1e (0.29 mmol, 0.06 g) in THF (1.0 mL) was added dropwise via syringe to a solution of Compound 4d (0.19 mmol, 0.04 g) and Et₃N (0.36 mmol, 0.05 mL) in THF (4 mL) at 0° C. The resulting suspension was allowed to warm to r.t. overnight, then made basic with a 2N NaOH solution and extracted with EtOAc (15 mL). The aqueous layer was extracted with EtOAc (2×10 mL). The organic layers were washed with brine, dried over Na₂SO₄ and then filtered. The solvent was removed in vacuo to yield 3,4-dichloro-N-(4-{[methyl-(tetrahydro-pyran-4-ylmethyl)-amino]-methyl}-phenyl)-benzamide Compound 4e as a yellow solid. The product was purified by preparative TLC (10:1 EtOAc:MeOH; Rf 0.4) (0.04 g, 52%). MS m/e 407 (M⁺H, 100%).

Iodomethane (0.5 mL) was added to a solution of Compound 4e (0.07 mmol, 0.03 g) in acetone (1.0 mL) and acetonitrile (1.0 mL) at r.t. The resulting solution was allowed to stand overnight, after which a yellow precipitate was observed. The solvent was removed in vacuo and the yellow solid was washed with Et₂O (2×1 mL) to obtain Compound 18 as a yellow solid (0.03 g, 96%). MS m/e 421 (M, 100%).

EXAMPLE 5

1-{4-[3-(3,4-dichloro-phenyl)-acryloylamino]-benzyl}-1-methyl-piperidinium iodide (Cpd 53)

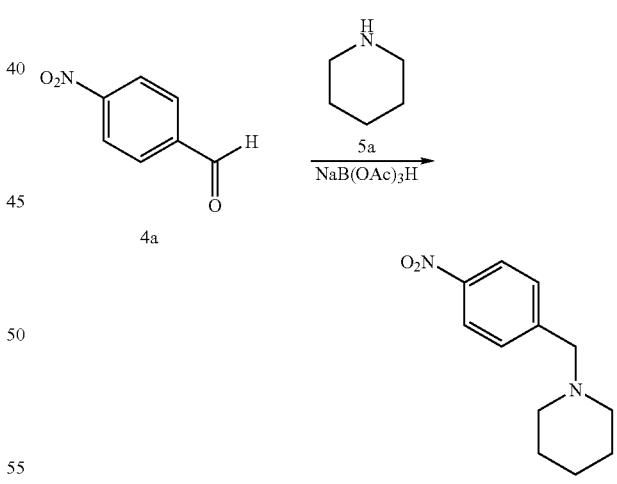

NaB(OAc)₃H (6.6 mmol, 1.4 g) was added to a mixture of 4-nitro-benzaldehyde Compound 4a (6.0 mmol, 0.9 g), piperidine Compound 5a (9.0 mmol, 0.9 mL) and glacial acetic acid (5 drops) in CH₂Cl₂ (50 mL) and the resulting suspension was stirred at r.t. overnight. The reaction mixture was made basic with a 2N NaOH solution and extracted with CH₂Cl₂. The organic layer was washed with brine, then separated and dried over Na₂SO₄. The drying agent was filtered and the solvent was removed in vacuo. The product was purified by flash column chromatography (10:1 EtOAc:MeOH) to yield 1-(4-nitro-benzyl)-piperidine Compound 5b as a yellow oil (0.89 g, 67% yield). MS m/e 221 (M+H, 100%).

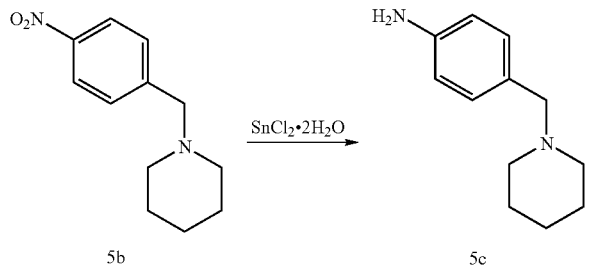

SnCl$_2$.2H$_2$O (10.0 mmol, 2.25 g) was added to a solution of Compound 5b (5.0 mmol, 1.1 g) in EtOH (25 mL) at r.t. and a mild exotherm was observed. The resulting yellow solution was stirred for 2 days then the solvent was removed in vacuo. The residue was made basic with a 2N NaOH solution and the aqueous layer was extracted with CH$_2$Cl$_2$ (2×25 mL). The combined organic layers were dried over Na$_2$SO$_4$ then filtered and the solvent was removed in vacuo to provide 4-piperidin-1-ylmethyl-phenylamine Compound 5c as an orange-yellow oil (0.8 g, 84% yield), which was used in the next step without further purification. MS m/e 191 (M+H, 100%).

A solution of 3-(3,4-dichloro-phenyl)-acryloyl chloride Compound 5d (0.21 mmol, 0.05 g) in THF (1.0 mL) was added dropwise via syringe to a solution of Compound 5c (0.21 mmol, 0.04 g) and Et$_3$N (5.1 mmol, 0.7 mL) in THF (4 mL) at 0° C. The resulting suspension was allowed to warm to r.t. overnight, then made basic with a 2N NaOH solution and extracted with EtOAc (25 mL). The aqueous layer was extracted with EtOAc (2×10 mL). The organic layers were washed with brine, dried over Na$_2$SO$_4$ and then filtered. The solvent was removed in vacuo to yield 3-(3,4-dichloro-phenyl)-N-(4-piperidin-1-ylmethyl-phenyl)-acrylamide Compound 5e as a yellow solid. The product was purified by preparative TLC (10:1 EtOAc:MeOH; Rf 0.4) to yield a yellow oil which was converted to the hydrochloride salt by dissolving a solution of Compound 5e in CH$_2$Cl$_2$ with a solution of HCl in Et$_2$O, followed by removal of the solvent (0.05 g, 60%). MS m/e 389 (M+H, 100%).

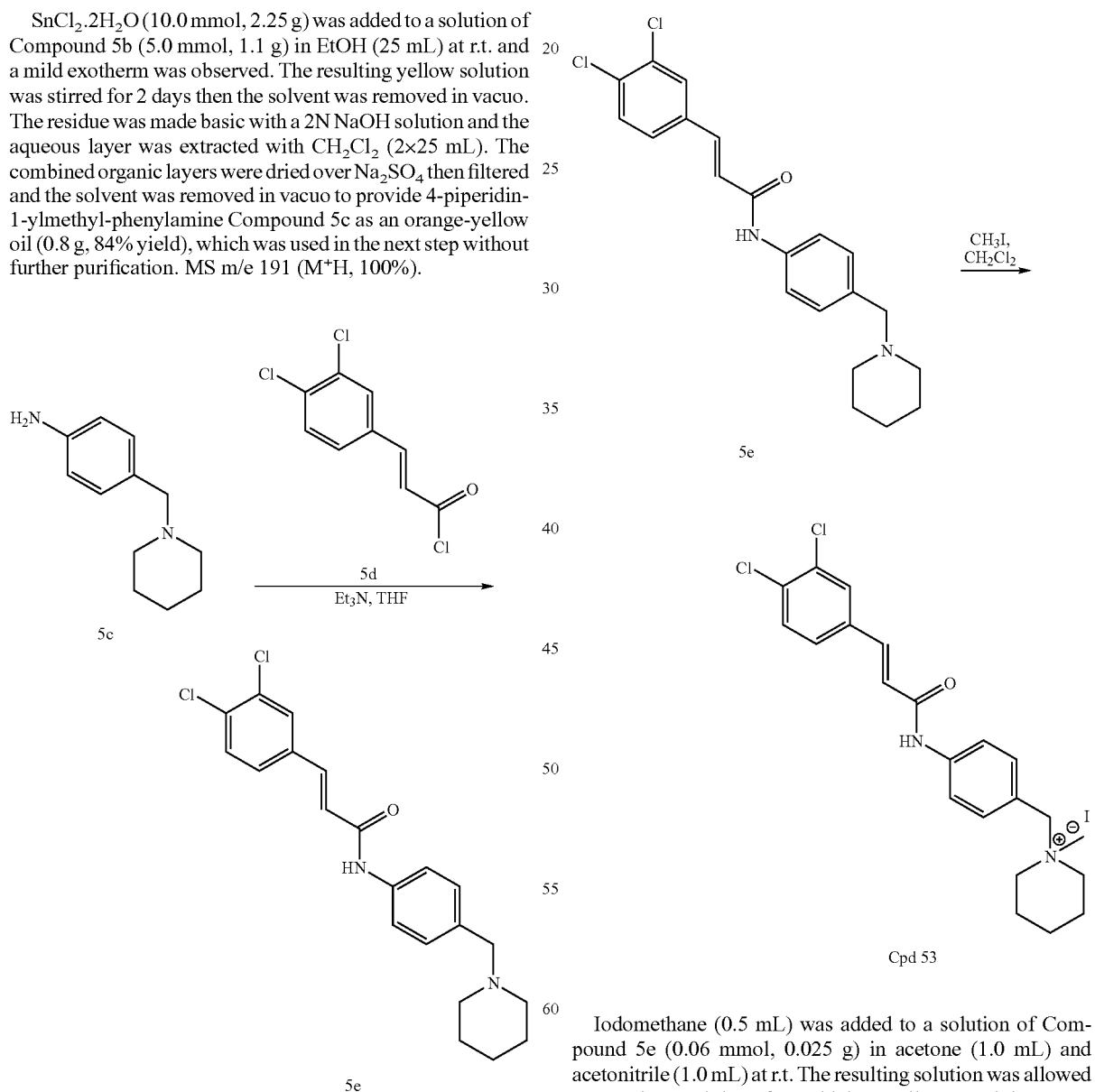

Iodomethane (0.5 mL) was added to a solution of Compound 5e (0.06 mmol, 0.025 g) in acetone (1.0 mL) and acetonitrile (1.0 mL) at r.t. The resulting solution was allowed to stand overnight, after which a yellow precipitate was observed. The solvent was removed in vacuo and the yellow solid was washed with Et$_2$O (2×1 mL) to provide Compound 53 as a yellow solid (0.03 g, 89%). MS m/e 530 (M, 100%).

EXAMPLE 6

[3-(3,4-dichloro-benzoylamino)-benzyl]-dimethyl-(tetrahydro-pyran-4-yl)-ammonium iodide (Cpd 7)

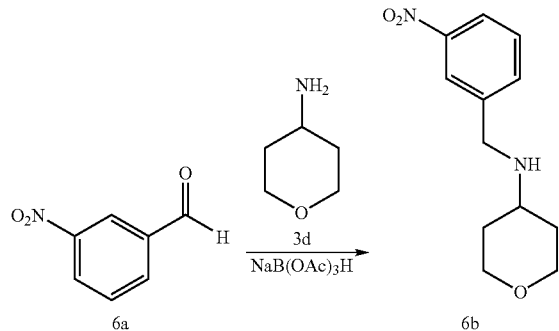

NaB(OAc)₃H (11.87 mmol, 2.52 g) was added to a mixture of 3-nitrobenzaldehyde Compound 6a (9.89 mmol, 1.49 g) and 4-amino-tetrahydro-pyran Compound 3d (9.89 mmol, 1.00 g) in CH₂Cl₂ (50 mL) and the resulting suspension was stirred overnight at r.t. The reaction mixture was made basic with a 2N NaOH solution and extracted with CH₂Cl₂. The organic layer was washed with brine, then separated and dried over MgSO₄. The drying agent was filtered and the solvent was removed in vacuo. The product was purified by flash column chromatography (9:1 CH₂Cl₂:MeOH) to yield (3-nitro-benzyl)-(tetrahydro-pyran-4-yl)-amine Compound 6b as a yellow oil (1.91 g, 82%). (This portion of Example 6 was adapted from Shiroshi, et al., *J. Med. Chem.*, 2000, 43, 2049). MS m/e 237 (M⁺H, 100%); ¹H NMR (300 MHz, CDCl₃) δ 1.35-1.53 (m, 4H), 1.82-1.95 (d, 2H), 2.65-2.8 (m, 1H), 3.38 (dt, J=3.2 Hz, J=11.2 Hz, 2H), 3.92-4.05 (m, 4H), 7.45-7.54 (t, 1H), 7.65-7.72 (d, 1H), 8.07-8.15 (d, 1H), 8.22 (s, 1H).

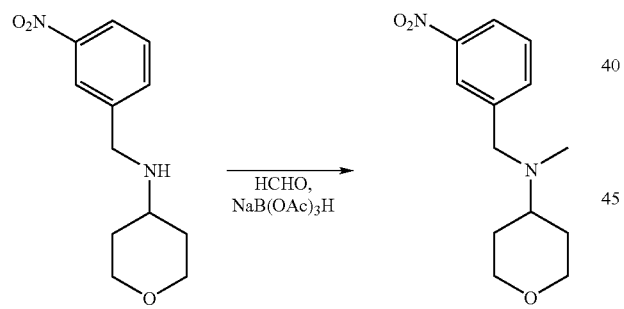

An aqueous solution of formaldehyde (37% solution, 9.4 mmol, 0.70 mL) was added to a solution of Compound 6b (8.09 mmol, 1.91 g) in CH₂Cl₂, followed by NaB(OAc)₃H (9.70 mmol, 2.06 g) added in one portion. The reaction mixture was stirred at r.t. for 12 hrs. An aliquot of the reaction mixture showed the formation of product (MS m/e 251, 100%). The reaction mixture was made basic with a 2N NaOH solution and extracted with CH₂Cl₂. The organic layer was washed with brine, then separated and dried over MgSO₄. The drying agent was filtered and the solvent was removed in vacuo to yield methyl-(3-nitro-benzyl)-(tetrahydro-pyran -4-yl)-amine Compound 6c as a yellow oil (1.87 g), which was used in the next step without further purification. MS m/e 251 (M⁺H, 100%); ¹H NMR (300 MHz, CDCl₃) δ 1.60-1.82 (m, 4H), 2.21 (s, 3H), 2.60-2.75 (m, 1H), 3.38 (dt, J=3.2 Hz, J=11.2 Hz, 2H), 3.68 (s, 2H), 4.02-4.10 (m, 2H), 7.45-7.54 (t, 1H), 7.65-7.72 (d, 1H), 8.07-8.15 (d, 1H), 8.22 s, 1H).

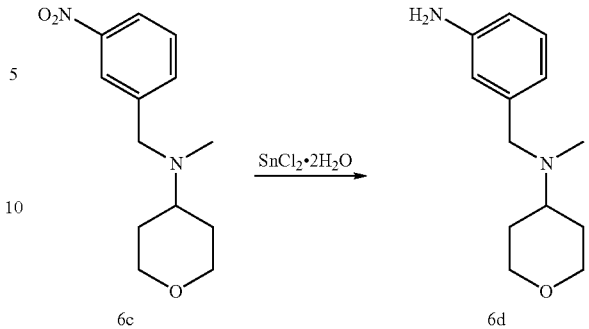

SnCl₂.2H₂O (14.868 mmol, 3.35 g) was added to a solution of Compound 6c (3.72 mmol, 0.930 g) in absolute ethanol (30 mL) at r.t. The reaction mixture was stirred overnight at 40° C. An aliquot of the reaction mixture showed the formation of product (MS m/e 221, 100%). The solvent was removed in vacuo to obtain an orange solid, which was made basic to pH 9 with a 1N NaOH solution. The product was extracted with EtOAc, then dried over MgSO₄ and filtered. The solvent was removed in vacuo to obtain (3-amino-benzyl)-methyl-(tetrahydro-pyran-4-yl)-amine Compound 6d as a yellow oil (0.490 g). MS m/e 221 (M⁺H, 100%); ¹H NMR (300 MHz, CDCl₃) δ 1.58-1.80 (m, 4H), 2.22 (s, 3H), 2.57-2.68 (m, 1H), 3.36 (dt, J=3.2 Hz, J=11.2 Hz, 2H), 3.50 (s, 2H), 3.65 (br, 2H), 3.98-4.10 (d, 2H), 6.55-6.62 (d, 1H), 6.70 (m, 2H), 7.05-7.12 (t, 1H).

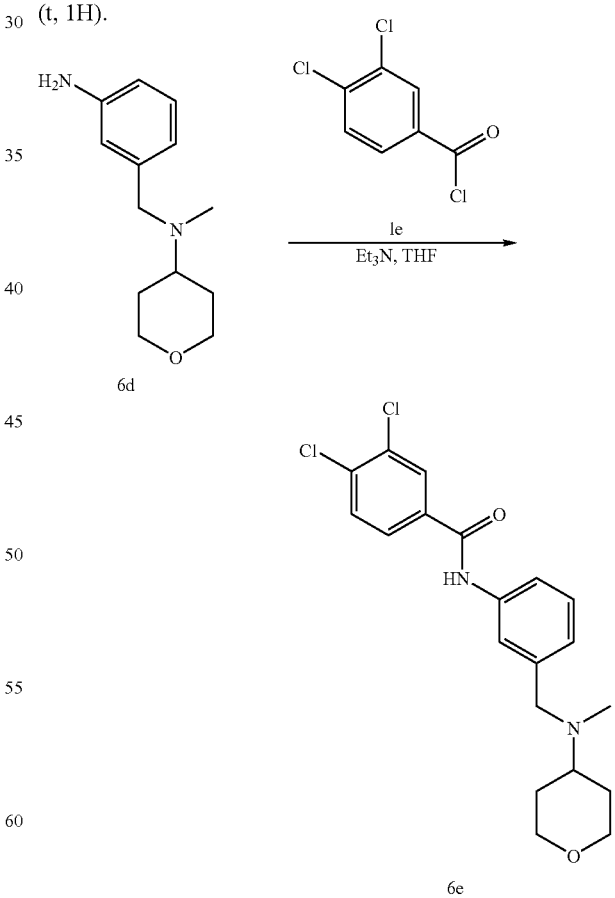

A solution of 3,4-dichlorobenzoyl chloride Compound 1e (0.250 mmol, 0.0523 g) was added dropwise to a solution of Compound 6d (0.227 mmol, 0.0500 g) and Et₃N (0.250 mmol, 0.04 mL) in THF (10 mL) at 0° C. The resulting suspension was allowed to warm to r.t. overnight. An aliquot of the reaction mixture showed the formation of product (MS m/e 393, 100%). The reaction mixture was made basic with a 2N NaOH solution and extracted with EtOAc. The organic layers were washed with brine, dried over $MgSO_4$ and then filtered. The solvent was removed in vacuo to yield 3,4-dichloro-N-(3-{[methyl-(tetrahydro-pyran-4-yl)-amino]-methyl}-phenyl)-benzamide Compound 6e. The product was purified by preparative TLC (9:1 EtOAc:MeOH) to yield a yellow solid (0.0380 g, 43%). MS m/e 393 ($M^+H$, 100%); $^1H$ NMR (300 MHz, $CDCl_3$) δ 1.58-1.83 (m, 4H), 2.21 (s, 3H), 2.61-2.75 (m, 1H), 3.35 (dt, J=3.1 Hz, J=11.0 Hz, 2H), 3.57 (s, 2H), 4.01-4.09 (m, 2H), 7.10 (d, J=1H), 7.25-7.32 (t, 1H), 7.45-7.52 (d, 1H), 7.55-7.65 (d, 2H), 7.65-7.72 (m, 1H), 7.95 (m, 1H), 8.25 (s, 1H).

| Cpd | Name | MS |
|---|---|---|
| 8 | [3-(3-bromo-benzoylamino)-benzyl]-dimethyl-(tetrahydro-pyran-4-yl)-ammonium iodide | 419 |
| 38 | {3-[3-(3-bromo-phenyl)-acryloylamino]-benzyl}-dimethyl-(tetrahydro-pyran-4-yl)-ammonium iodide | 445 |
| 52 | 1-{3-[3-(3-bromo-phenyl)-acryloylamino]-benzyl}-1-methyl-piperidinium iodide | 415 |
| 56 | 1-methyl-1-[3-(3-trifluoromethyl-benzoylamino)-benzyl]-piperidinium iodide | 377 |
| 65 | dimethyl-(tetrahydro-pyran-4-yl)-[3-(3-trifluoromethyl-benzoylamino)-benzyl]-ammonium iodide | 407 |
| 83 | cyclohexyl-{3-[3-(3,4-dichloro-phenyl)-acryloylamino]-benzyl}-dimethyl-ammonium iodide | 431 |
| 84 | cyclohexyl-{3-[3-(4-fluoro-phenyl)-acryloylamino]-benzyl}-dimethyl-ammonium iodide | 381 |

EXAMPLE 7

[4-(4-chloro-3-trifluoromethyl-benzoylamino)-benzyl]-dimethyl-(tetrahydro-pyran-4-yl)-ammonium iodide (Cpd 33)

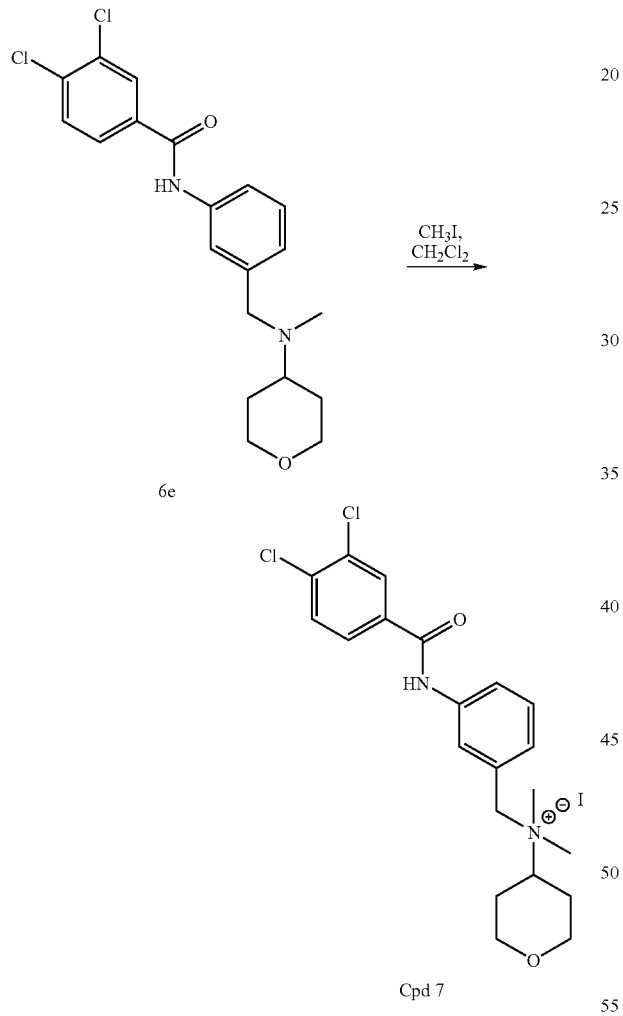

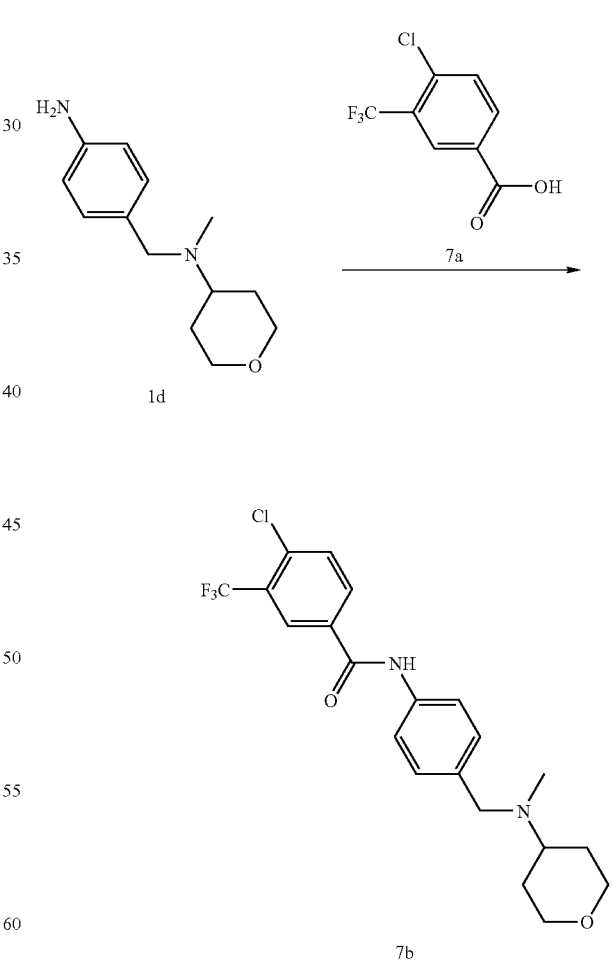

Iodomethane (0.0161 mol, 1.0 mL) was added to a solution of Compound 6e (0.0674 mmol, 0.0265 g) in acetonitrile (3 mL) and acetone (3 drops) at r.t. The resulting solution was stirred overnight, then the solvent was removed in vacuo. The product was washed with $Et_2O$ (10 mL) and dried in a vacuum oven for 12 hrs to provide Compound 7 as an orange solid (0.0326 g, 90.3%). MS m/e 407 (M, 100%).

Using the procedure of Example 6 and appropriate known reagents and starting materials, other compounds of the present invention may be prepared including, but not limited to (MS: Mass Spec data as MS m/e $M^+H$):

EDIC hydrochloride (0.33 mmol, 0.07 g) was added in one portion to a suspension of (4-amino-benzyl)-methyl-(tetrahydro-pyran-4-yl)-amine Compound 1d (0.25 mmol, 0.06 g), 4-chloro-3-trifluoromethyl-benzoic acid Compound 7a (0.22 mmol, 0.05 g) and HOBt (0.22 mmol 0.03 g) in DMF (5.0 mL) at 0° C. The resulting suspension was warmed to r.t. and a crystal of DMAP and Et₃N (0.65 mmol, 0.1 mL) were added. The mixture was stirred overnight and produced an orange-yellow suspension. The suspension was poured into water and the aqueous layer was extracted with EtOAc (25 mL). The organic layer was washed with water (2×20 mL), then a solution of 5% NaOH (10 mL) and brine. The organic layer was separated, dried over Na₂SO₄ and filtered. The solvent was removed in vacuo to yield a residue, which was purified via preparative TLC (15:1 CH₂Cl₂:MeOH) to provide 4-chloro-N-(4-{[methyl-(tetrahydro-pyran-4-yl)-amino]-methyl}-phenyl)-3-trifluoromethyl-benzamide Compound 7b (0.06 g, 63%) as a pale yellow solid. MS m/e 427 (M⁺H, 100%).

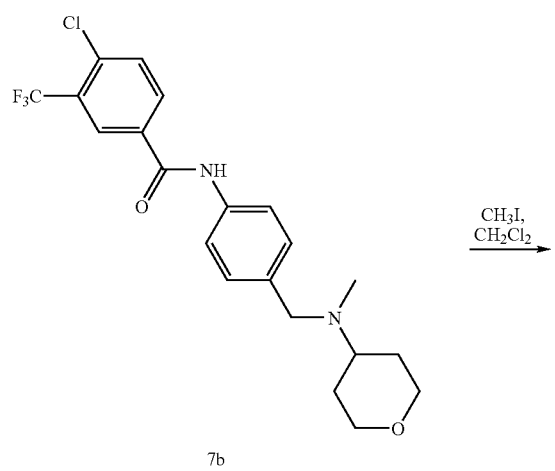

Iodomethane (0.5 mL) was added to a solution of Compound 7b (0.07 mmol, 0.03 g) in CH₂Cl₂ (1.0 mL) at r.t. The resulting solution stood overnight, after which a pale yellow precipitate was observed. The solvent was removed in vacuo and the yellow solid was washed with Et₂O (2×1 mL) to provide Compound 33 as a yellow solid (0.03 g, 96%). MS m/e 441 (M⁺H, 100%).

EXAMPLE 8

(2S)-[4-(3,4-dichloro-benzoylamino)-benzyl]-dimethyl-(tetrahydro-furan -2-ylmethyl)-ammonium iodide (Cpd 15)

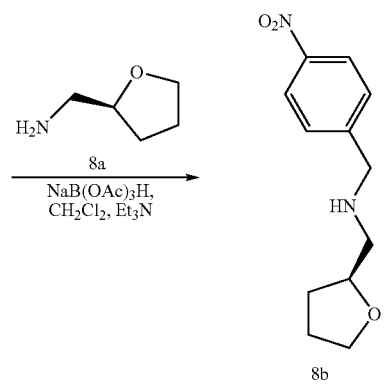

NaB(OAc)₃H (3.5 mmol, 0.75 g) was added to a mixture of 4-nitro-benzaldehyde Compound 4a (2.8 mmol, 0.42 g), (S)-(+)-(tetrahydro-furan-2-yl)-methylamine Compound 8a (3.0 mmol, 0.3 mL) and glacial acetic acid (2 drops) in CH₂Cl₂ (25 mL) and the resulting suspension was allowed to stir at room temperature for 12 hrs. An aliquot of the reaction mixture showed the formation of (S)-(4-nitro-benzyl)-(tetrahydro-furan-2-ylmethyl)-amine Compound 8b (MS m/e 237, 100%).

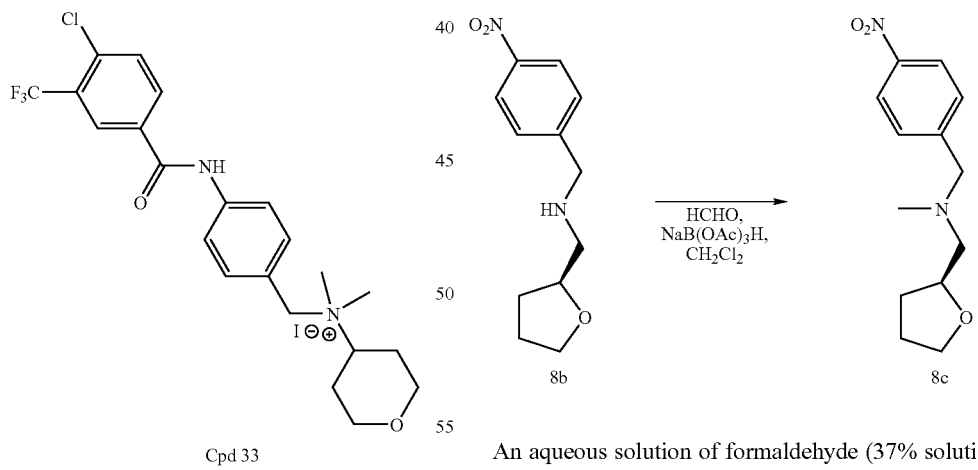

An aqueous solution of formaldehyde (37% solution, 9.6 mmol, 0.8 mL) was added to the reaction mixture followed by NaB(OAc)₃H (3.5 mmol, 0.75 g) and the reaction mixture was allowed to stir at r.t. for 2 hrs. The reaction mixture was basified with 2N NaOH solution and was extracted with CH₂Cl₂. The organic layer was washed with brine, separated and dried over Na₂SO₄. The drying agent was filtered and the solvent was removed in vacuo. The gummy residue thus obtained was spectroscopically characterized to be (S)-methyl-(4-nitro-benzyl)-(tetrahydro-furan-2-ylmethyl)-amine Compound 8c (0.74 g). MS m/e 251 (M⁺H, 100%).

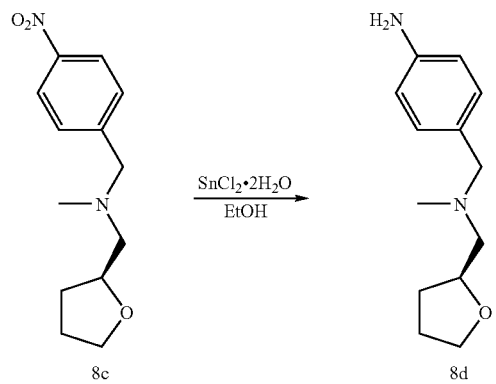

SnCl₂·2H₂O (10.0 mmol, 2.35 g) was added to a solution of Compound 8c (2.8 mmol, 0.74 g) in EtOH (25 mL) at r.t. and the resulting yellow solution was stirred overnight. The solvent was removed in vacuo. The residue was basified with 2N NaOH solution and the aqueous layer was extracted with CH₂Cl₂ (2×30 mL). The combined organic layers were dried over Na₂SO₄, filtered and the solvent was removed in vacuo to obtain (S)-4-{[methyl-(tetrahydro-furan -2-ylmethyl)-amino]-methyl}-phenylamine Compound 8d as a thick yellow oil (0.54 g, 88% yield), which was used in the next step without purification. MS m/e 221 (M⁺H, 100%).

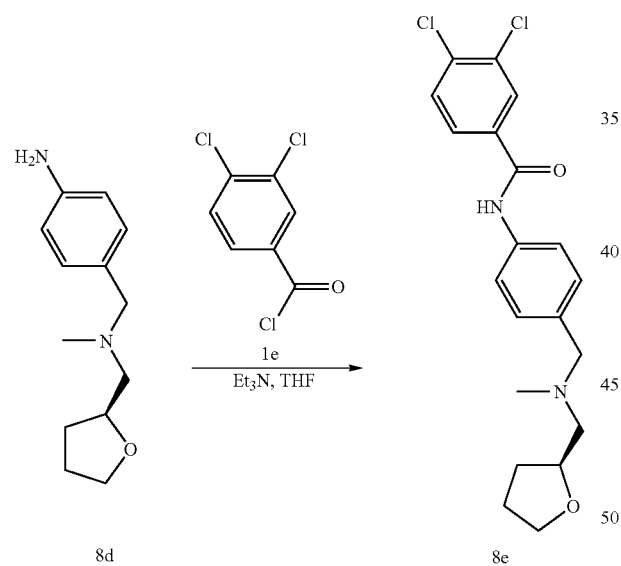

A solution of 3,4-dichlorobenzoyl chloride Compound 1e (0.25 mmol, 0.05 g) in THF (5 mL) was added to a solution of Compound 8d (0.25 mmol, 0.06 g) and Et₃N (0.5 mmol, 0.07 mL) in THF (3 mL) at 0° C. and the reaction mixture was stirred overnight. The pale yellow suspension was poured in water and was extracted with EtOAc (20 mL). The organic layer was washed with water (2×20 mL) followed by brine. The organic layer was separated, dried over Na₂SO₄ and filtered. The solvent was removed in vacuo and the resulting residue was purified by preparative TLC (15:1 CH₂Cl₂/MeOH) to yield (S)-3,4-dichloro-N-(4-{[methyl-(tetrahydro-furan -2-ylmethyl)-amino]-methyl}-phenyl)-benzamide Compound 8e as a pale yellow solid (0.06 g, 61%). M.S. m/e 393 (M⁺H, 100%).

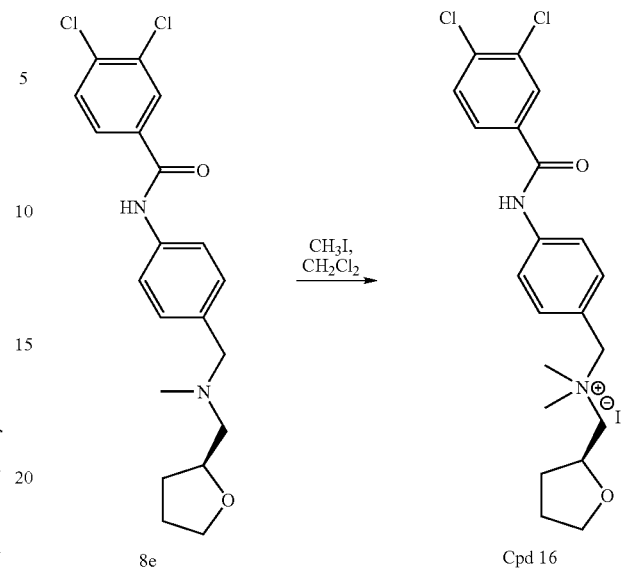

Iodomethane (0.5 mL) was added to a solution of Compound 8e (0.07 mmol, 0.03 g) in CH₂Cl₂ (1.0 mL) at r.t. and the resulting solution was allowed to stand overnight. A yellow precipitate was observed. The solvent was removed in vacuo and the yellow solid was washed with Et₂O to obtain Compound 15 as a off-white powder (0.04 g, 97%). MS m/e 534 (M, 100%).

Using the procedure of Example 8 and the appropriate known reagents and starting materials, other compounds of the invention may be prepared including, (MS: Mass Spec data as MS m/e M⁺H):

| Cpd | Name | MS |
|---|---|---|
| 16 | (2R)-[4-(3,4-dichloro-benzoylamino)-benzyl]-dimethyl-(tetrahydro-furan-2-ylmethyl)-ammonium iodide | 407 |
| 165 | (2S)-{4-[(5-chloro-1H-indole-2-carbonyl)-amino]-benzyl}-dimethyl-(tetrahydro-furan-2-ylmethyl)-ammonium iodide | 412 |

EXAMPLE 9

4-methyl-4-(4-{[3-(3-trifluoromethyl-phenyl)-acryloylamino]-methyl}-benzyl)-morpholin-4-ium iodide (Cpd 62)

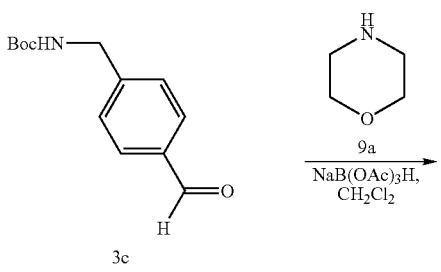

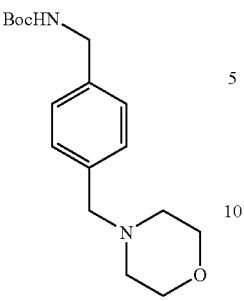

NaB(OAc)₃H (0.82 mmol, 0.17 g) was added to a mixture of (4-formyl-benzyl)-carbamic acid tert-butyl ester Compound 3c (0.75 mmol, 0.17 g) and morpholine Compound 9a (0.75 mmol, 0.07 mL) in CH₂Cl₂ (20 mL) and the resulting suspension was stirred at room temperature for 6 hrs. The reaction mixture was basified with 2N NaOH solution and was extracted with CH₂Cl₂. The organic layer was washed with brine, separated and dried over Na₂SO₄. The drying agent was filtered and the solvent was removed in vacuo to a crude product as a pale yellow oil. MS m/e 307 (M⁺H, 100%). The product was purified by prep TLC (10:1 CH₂Cl₂/MeOH, Rf=0.5) to yield (4-morpholin-4-ylmethyl-benzyl)-carbamic acid tert-butyl ester Compound 9b.

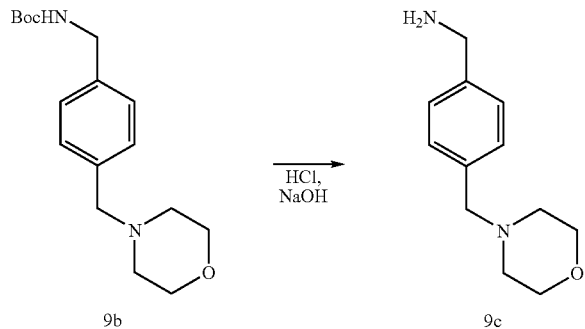

Compound 9b was dissolved in CH₂Cl₂ and was stirred with HCl in dioxane at r.t. for 12 hrs. The solvent was removed to obtain a gummy residue, which was basified with 2N NaOH and extracted with EtOAc. The organic layer was washed with brine, separated and dried over Na₂SO₄. The drying agent was filtered and the solvent was removed in vacuo to obtain 4-morpholin-4-ylmethyl-benzylamine Compound 9c as pale yellow oil (wt. 0.09 g, 58% yield). MS m/e 207 (M⁺H, 100%).

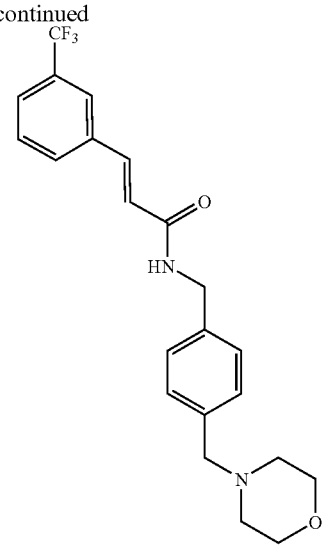

A solution of 3-(3-trifluoromethyl-phenyl)-acryloyl chloride Compound 3g (0.3 mmol, 0.07 g) in THF (2 mL) was added dropwise to a solution of Compound 9c (0.19 mmol, 0.04 g) and Et₃N (0.8 mmol, 0.14 mL) in THF (10 mL) at 0° C. The resulting suspension was allowed to warm to r.t. overnight. The reaction mixture was basified with 2N NaOH solution and was extracted with EtOAc (25 mL). The aqueous layer was extracted with EtOAc (2×10 mL). The organic layers were washed with brine, then dried over Na₂SO₄ and filtered. The solvent was removed in vacuo and the resulting yellow gummy oil was purified by preparative TLC (10:1 CH₂Cl₂/MeOH, Rf=0.5) to yield N-(4-morpholin-4-ylmethyl-benzyl)-3-(3-trifluoromethyl-phenyl)-acrylamide Compound 9d as a pale yellow solid (0.06 g, 77%). MS m/e 405 (M⁺H, 100%).

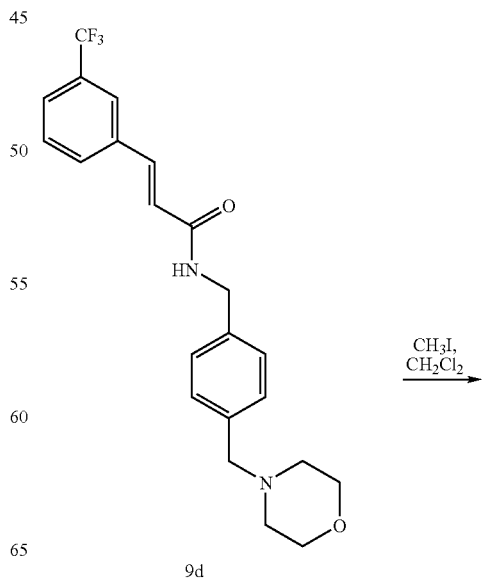

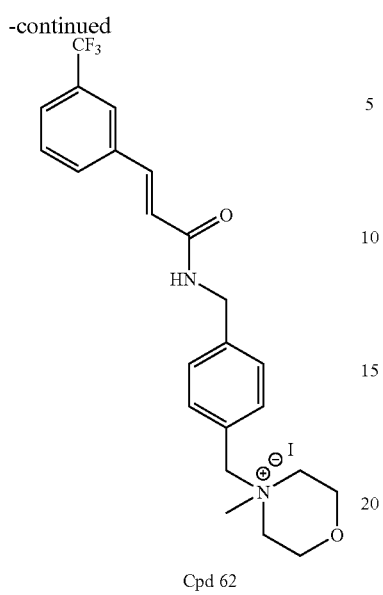

Cpd 62

MeI (1.28 mmol, 0.08 mL) was added dropwise to a solution of Compound 9d (0.07 mmol, 0.03 g) in a mixture of acetone/acetonitrile (2 mL). The solution was stirred at room temperature for 24 hrs and concentrated. The resulting residue was washed with ether (2×1 mL) and dried under high vacuum to give Compound 62 (0.03 g, 78%). MS m/e 546 (M).

EXAMPLE 10

[4-(3-bromo-benzoylamino)-benzyl]-cyclohexyl-dimethyl-ammonium iodide (Cpd 73)

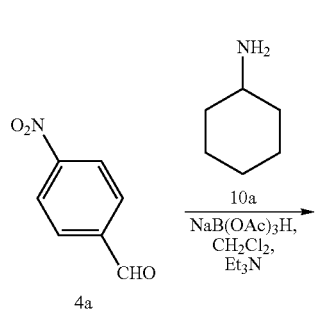

NaB(OAc)$_3$H (11.0 mmol, 2.33 g) was added to a mixture of 4-nitro-benzaldehyde Compound 4a (10.0 mmol, 1.51 g), cyclohexylamine Compound 10a (10.5 mmol, 1.2 mL) and glacial acetic acid (5 drops) in CH$_2$Cl$_2$ (40 mL) and the resulting suspension was allowed to stir at room temperature for 12 hrs. An aliquot of the reaction mixture showed the formation of product (MS m/e 235, 100%). The reaction mixture was basified with 2N NaOH solution and was extracted with CH$_2$Cl$_2$. The organic layer was washed with brine, separated and dried over Na$_2$SO$_4$. The drying agent was filtered and the solvent was removed in vacuo to yield cyclohexyl-(4-nitro-benzyl)-amine Compound 10b as yellow oil (1.56 g, 67% yield), which was used in the next step without purification.

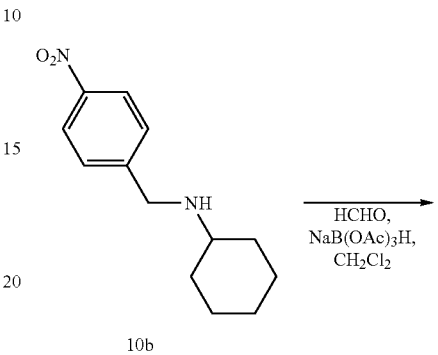

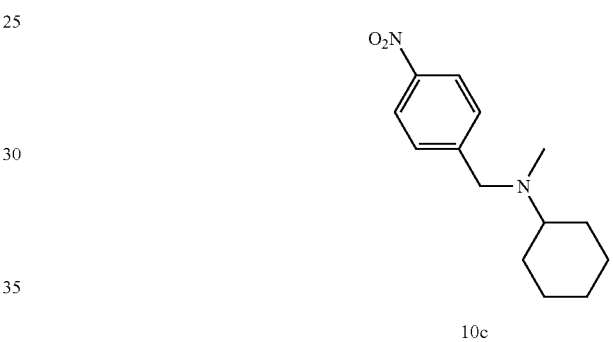

An aqueous solution of formaldehyde (37% solution, 9.6 mmol, 0.8 mL) was added to a solution of Compound 10b (3.41 mmol, 0.8 g) in CH$_2$Cl$_2$ followed by NaB(OAc)$_3$H (7.0 mmol, 1.5 g) and the mixture was allowed to stir at r.t. for 2 hrs. The reaction mixture was basified with 2N NaOH solution and was extracted with CH$_2$Cl$_2$. The organic layer was washed with brine, separated and dried over Na$_2$SO$_4$. The drying agent was filtered and the solvent was removed in vacuo. The gummy residue was purified by column chromatography (9:1 EtOAc/MeOH) to yield cyclohexyl-methyl-(4-nitro-benzyl)-amine Compound 10c as yellow oil (0.8 g, 94% yield). MS m/e 249 (M$^+$H, 100%).

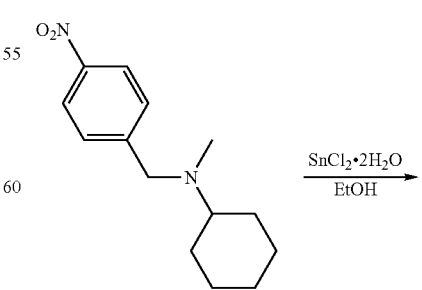

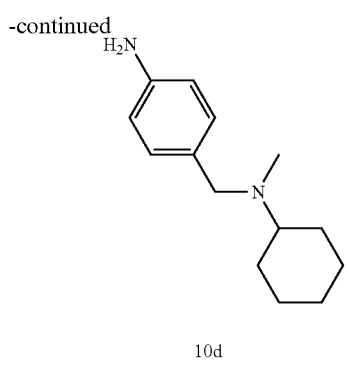

10d

SnCl$_2$.2H$_2$O (16.0 mmol, 3.6 g) was added to a solution of Compound 10c (3.2 mmol, 0.8 g) in EtOH (40 mL) at r.t. and the resulting yellow solution was stirred overnight. The solvent was removed in vacuo. The residue was basified with 2N NaOH solution and the aqueous layer was extracted with CH$_2$Cl$_2$ (2×30 mL). The combined organic layers were dried over Na$_2$SO$_4$, filtered and the solvent was removed in vacuo to obtain 4-[(cyclohexyl-methyl-amino)-methyl]-phenylamine Compound 10d as a thick yellow oil (0.69 g, 98% yield), which was used in the next step without purification. MS m/e 219 (M$^+$H, 100%).

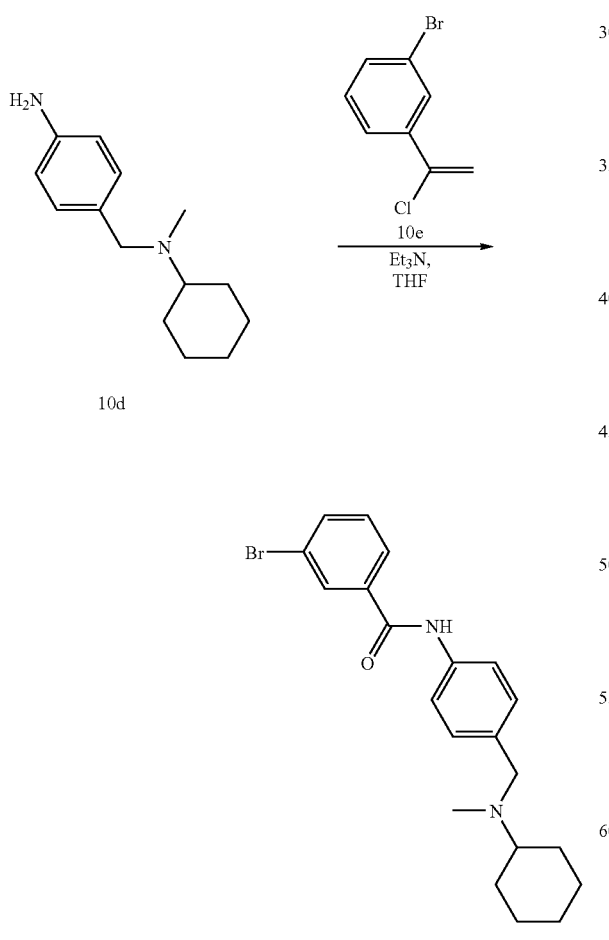

A solution of 3-bromobenzoyl chloride Compound 10e (0.8 mmol, 0.15 g) was added to a solution of Compound 10d (0.7 mmol, 0.2 g) and Et$_3$N (0.8 mmol, 0.14 mL) in THF (15 mL) in THF (5 mL) at 0° C. and the reaction mixture was stirred overnight. The pale yellow suspension was poured in water and was extracted with EtOAc (30 mL). The organic layer was washed with water (2×20 mL) followed by 5% NaOH solution (10 mL) and brine. The organic layer was separated, dried over Na$_2$SO$_4$ and filtered. The solvent was removed in vacuo and the resulting residue was purified by preparative TLC (15:1 CH$_2$Cl$_2$/MeOH) to yield 3-bromo-N-{4-[(cyclohexyl-methyl-amino)-methyl]-phenyl}-benzamide Compound 10f as a pale yellow solid (0.21 g, 75%). MS m/e 401 (M$^+$H, 100%).

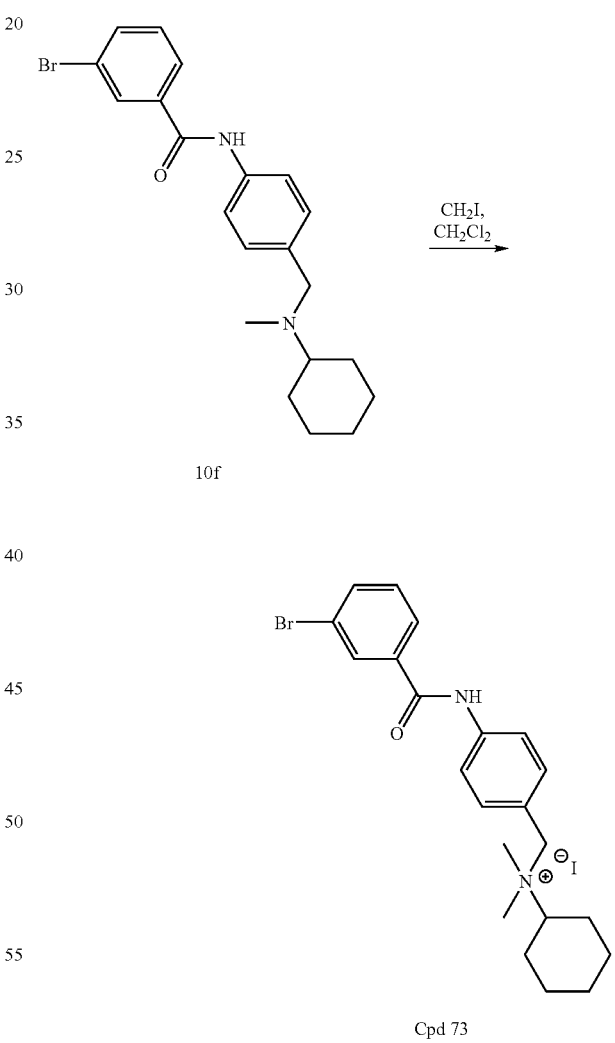

Iodomethane (0.5 mL) was added to a solution of Compound 10f (0.07 mmol, 0.03 g) in CH$_2$Cl$_2$ (1.0 mL) at r.t. and the resulting solution was allowed to stand overnight. A yellow precipitate was observed. The solvent was removed in vacuo and the yellow solid was washed with Et$_2$O to provide Compound 73 as a pale yellow solid (0.04 g, 99%). MS m/e 542 (M, 100%).

EXAMPLE 11 cyclohexyl-dimethyl-{4-[(4'-methyl-biphenyl-3-carbonyl)-amino]-benzyl}-ammonium iodide (Cpd 86)

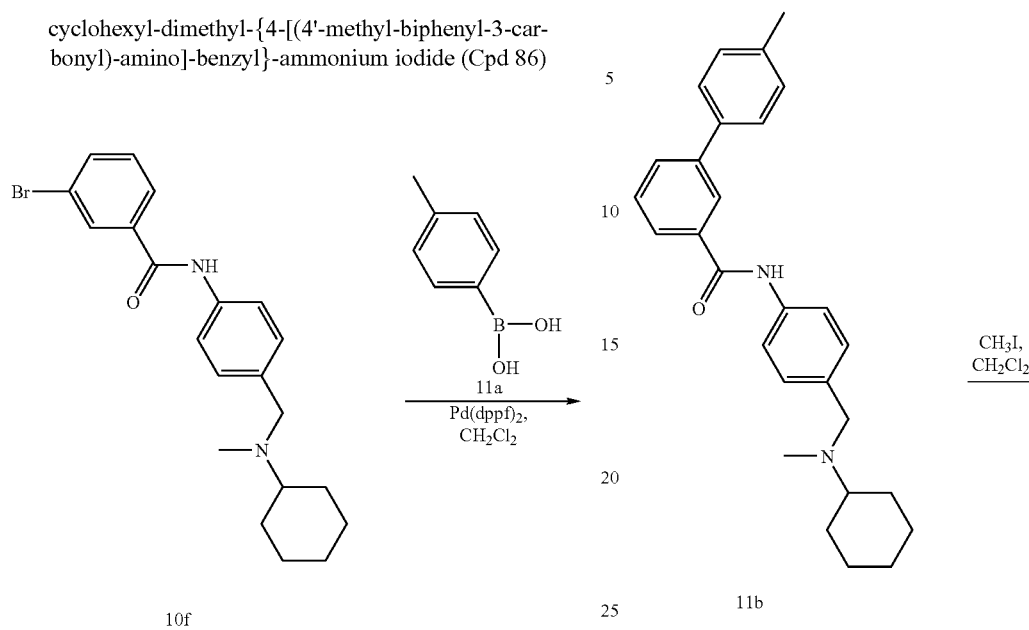

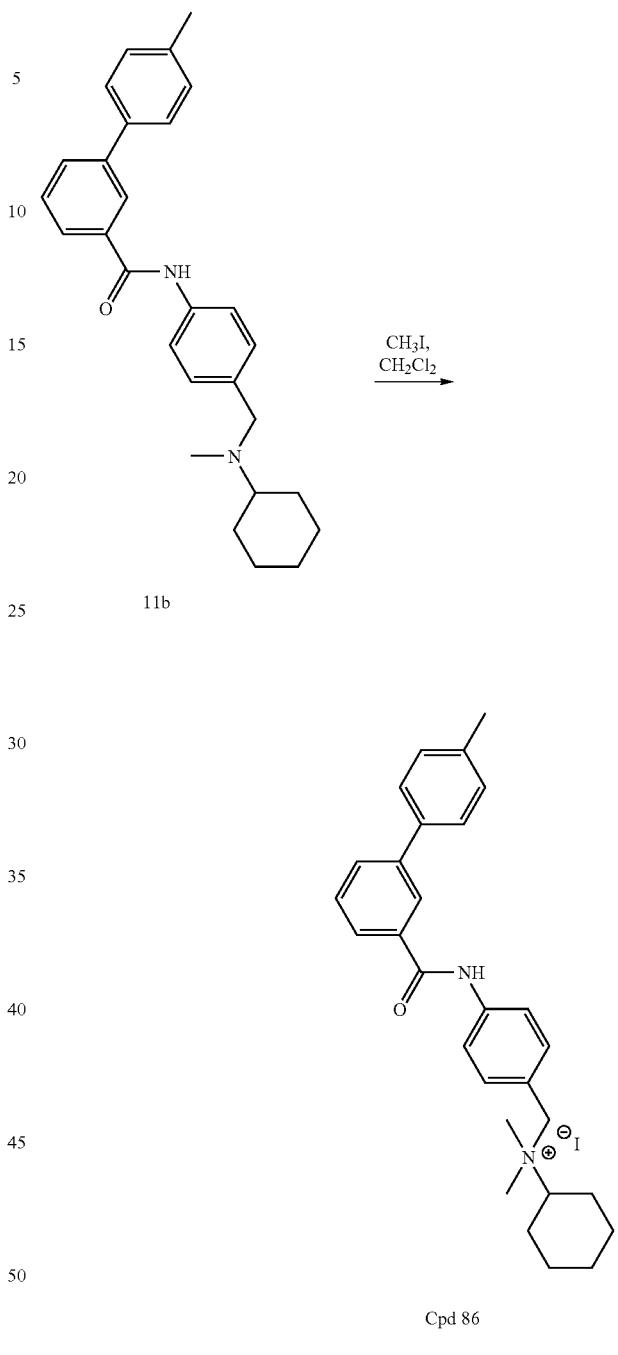

K$_2$CO$_3$ (0.2 mmol, 0.03 g) and a Pd(dppf)$_2$ catalyst:DCM complex (1:1) (0.03 mmol, 0.02 g) was added to a mixture of 3-bromo-N-{4-[(cyclohexyl-methyl-amino)-methyl]-phenyl}-benzamide Compound 10f (0.1 mmol, 0.04 g) and p-tolylboronic acid Compound 11a (0.12 mmol, 0.02 g) in a mixed solution of toluene/ethanol/water (7 mL/1 mL/1 mL). The resulting suspension was heated to reflux for 5 hrs, concentrated and purified with preparative TLC (10% MeOH/2% Et$_3$N/88% EtOAc) to yield 4'-methyl-biphenyl-3-carboxylic acid {4-[(cyclohexyl-methyl-amino)-methyl]-phenyl}amide Compound 11b (0.02 g, 48%). MS m/e 413 (M+1).

Iodomethane (0.32 mmol, 0.02 mL) was added dropwise to a solution of Compound 11b (0.012 mmol, 0.005 g) in acetone/acetonitrile (1 mL, 0.5 mL/0.5 mL). The resulting solution was stirred at room temperature for 48 hrs and concentrated. The obtained residue was washed with ether (2×1 mL) and dried under a high vacuum to give Compound 86 (0.01 g, 89%). MS m/e 427 (M$^+$H).

Using the procedure of Example 11 and known appropriate reagents and starting materials, other compounds of the present invention may be prepared including, (MS: Mass Spec data as MS m/e M$^+$H):

| Cpd | Name | MS |
|---|---|---|
| 85 | dimethyl-(tetrahydro-pyran-4-yl)-{4-[(4'-trifluoromethyl-biphenyl-3-carbonyl)-amino]-benzyl}-ammonium iodide | 483 |
| 87 | dimethyl-{4-[(4'-methyl-biphenyl-3-carbonyl)-amino]-benzyl}-(tetrahydro-pyran-4-yl)-ammonium iodide | 429 |
| 88 | {4-[(biphenyl-4-carbonyl)-amino]-benzyl}-dimethyl-(tetrahydro-pyran-4-yl)-ammonium iodide | 415 |

EXAMPLE 12 dimethyl-{4-[(1-methyl-1H-indole-2-carbonyl)-amino]-benzyl}-(tetrahydro-pyran-4-yl)-ammonium iodide (Cpd 158)

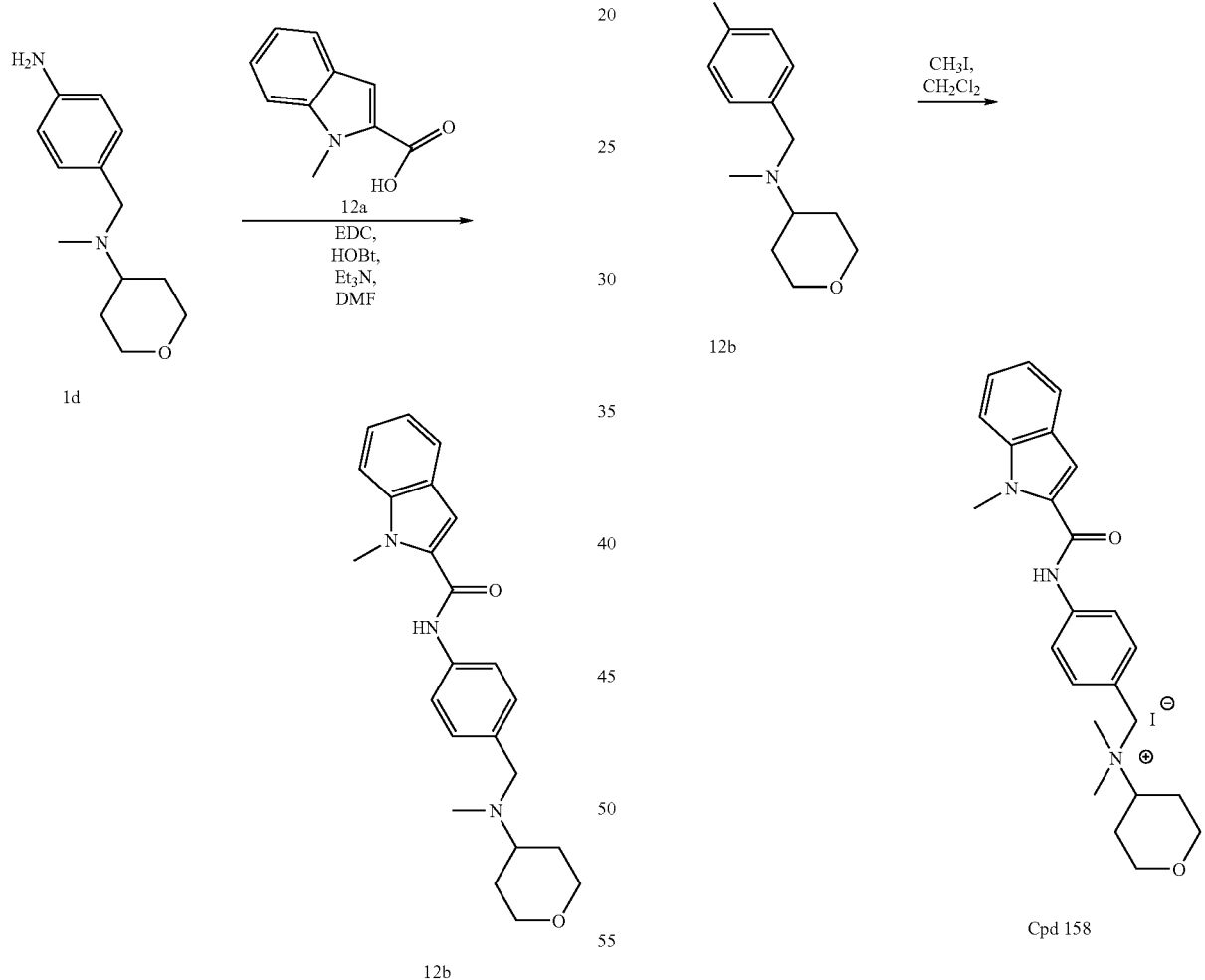

EDIC (0.33 mmol, 0.07 g) was added in one portion to a mixture of (4-amino-benzyl)-methyl-(tetrahydro-pyran-4-yl)-amine Compound 1d (0.25 mmol, 0.06 g), 1-methyl-1H-indole-2-carboxylic acid Compound 12a (0.22 mmol, 0.04 g) and HOBt (0.22 mmol, 0.03 g) in DMF (5.0 mL) at 0° C. The resulting suspension was warmed to r.t. and then a crystal of DMAP and Et₃N (0.65 mmol, 0.11 mL) was added and the reaction mixture was stirred overnight. The resulting orange-yellow suspension was poured in water and was extracted with EtOAc (25 mL). The organic layer was washed with water (2×20 mL) followed by 5% NaOH solution (10 mL) and brine. The organic layer was separated, dried over $Na_2SO_4$ and filtered. The solvent was removed in vacuo and the resulting residue was purified by preparative TLC (15:1 $CH_2Cl_2$/MeOH) to yield 1-methyl-1H-indole-2-carboxylic acid (4-{[methyl-(tetrahydro-pyran -4-yl)-amino]-methyl}-phenyl)-amide Compound 12b as a pale yellow solid (0.05 g, 60%). MS m/e 378 ($M^+H$, 100%).

Iodomethane (0.5 mL) was added to a solution of Compound 12b (0.08 mmol, 0.03 g) in $CH_2Cl_2$ (1.0 mL) at r.t. The mixture was allowed to stand overnight and a yellow precipitate was observed. The solvent was removed in vacuo and the yellow solid was washed with $Et_2O$ to obtain Compound 158 as a yellow solid (0.03 g, 77%). MS m/e 391 ($M^+H$, 100%).

Using the procedure of Example 12 and known appropriate reagents and starting materials, other compounds of the present invention may be prepared including, (MS: Mass Spec data as MS m/e $M^+H$):

| Cpd | Name | MS |
|---|---|---|
| 159 | {4-[(5-chloro-1H-indole-2-carbonyl)-amino]-benzyl}-dimethyl-(tetrahydro-pyran-4-yl)-ammonium iodide | 412 |
| 160 | {4-[(5-bromo-1H-indole-2-carbonyl)-amino]-benzyl}-dimethyl-(tetrahydro-pyran-4-yl)-ammonium iodide | 456 |
| 161 | dimethyl-{4-[(1-methyl-1H-indole-3-carbonyl)-amino]-benzyl}-(tetrahydro-pyran-4-yl)-ammonium iodide | 392 |
| 163 | cyclohexyl-dimethyl-{4-[(1-methyl-1H-indole-2-carbonyl)-amino]-benzyl}-ammonium iodide | 390 |
| 166 | bicyclo[2.2.1]hept-2-ylmethyl-{4-[(5-chloro-1H-indole-2-carbonyl)-amino]-benzyl}-dimethyl-ammonium iodide | 422 |
| 174 | {4-[(3-chloro-benzo[b]thiophene-2-carbonyl)-amino]-benzyl}-dimethyl-(tetrahydro-pyran-4-yl)-ammonium iodide | 429 |
| 175 | {4-[(2,5-dichloro-thiophene-3-carbonyl)-amino]-benzyl}-dimethyl-(tetrahydro-pyran-4-yl)-ammonium iodide | 413 |
| 176 | {4-[(benzo[b]thiophene-2-carbonyl)-amino]-benzyl}-dimethyl-(tetrahydro-pyran-4-yl)-ammonium iodide | 395 |
| 177 | {4-[(benzo[b]thiophene-2-carbonyl)-amino]-benzyl}-cyclohexyl-dimethyl-ammonium iodide | 393 |
| 178 | {4-[(3-chloro-benzo[b]thiophene-2-carbonyl)-amino]-benzyl}-cyclohexyl-dimethyl-ammonium iodide | 427 |

EXAMPLE 13

{4-[(1-benzyl-1H-indole-3-carbonyl)-amino]-benzyl}-dimethyl-(tetrahydro-pyran-4-yl)-ammonium iodide (Cpd 162)

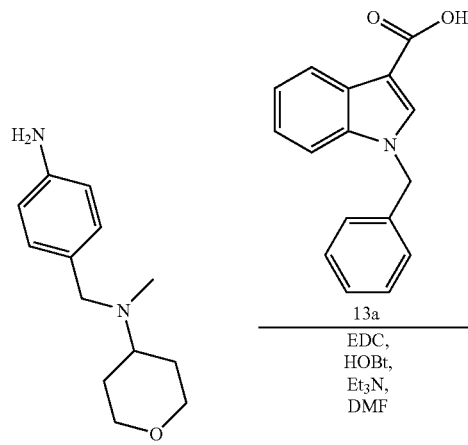

EDCI (0.33 mmol, 0.07 g) was added in one portion to a suspension of (4-amino-benzyl)-methyl-(tetrahydro-pyran-4-yl)-amine Compound 1d (0.25 mmol, 0.06 g), 1-benzyl-1H-indole-3-carboxylic acid Compound 13a (0.22 mmol, 0.06 g) and HOBt (0.22 mmol, 0.03 g) in DMF (5.0 mL) at 0° C. The resulting suspension was warmed to r.t. and then a crystal of DMAP and $Et_3N$ (0.65 mmol, 0.1 mL) was added and the reaction mixture was stirred overnight. The orange-yellow suspension was poured in water and was extracted with EtOAc (25 mL). The organic layer was washed with water (2×20 mL) followed by 5% NaOH solution (10 mL) and brine. The organic layer was separated, dried over $Na_2SO_4$ and filtered. The solvent was removed in vacuo and the resulting residue was purified by preparative TLC (15:1 $CH_2Cl_2$/MeOH) to yield Compound 13b as a pale yellow solid (0.07 g, 71%). MS m/e 454 ($M^+H$, 100%).

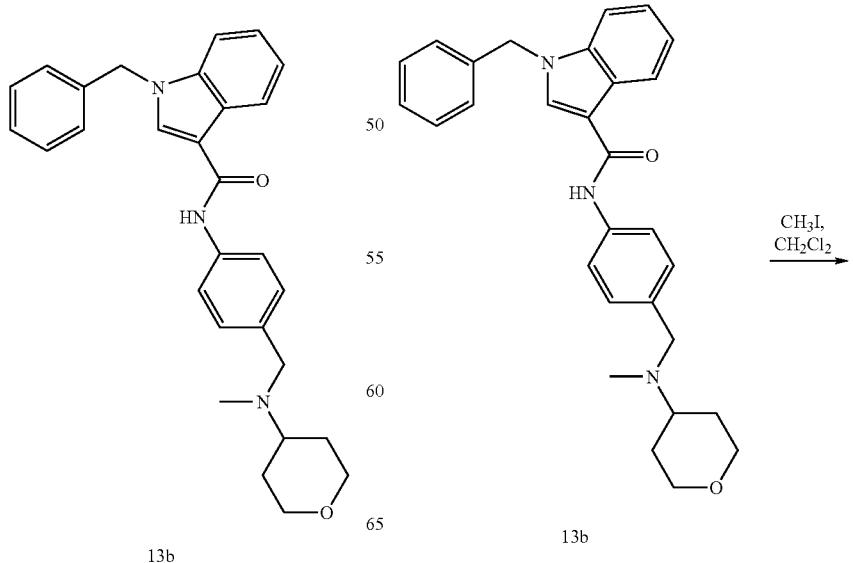

-continued

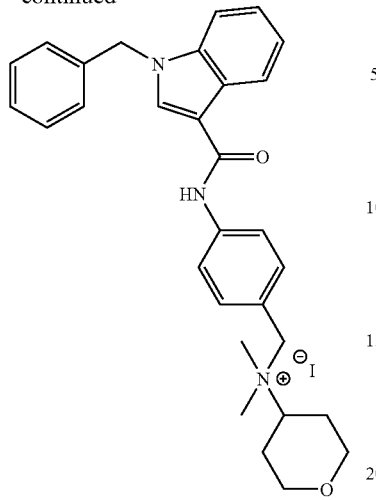

Cpd 162

Iodomethane (0.5 mL) was added to a solution of Compound 13b (0.08 mmol, 0.04 g) in CH$_2$Cl$_2$ (1.0 mL) at r.t. The mixture was allowed to stand overnight and a yellow precipitate was observed. The solvent was removed in vacuo and the yellow solid was washed with Et$_2$O to obtain Compound 162 as a yellow solid (0.05 g, 84%). MS m/e 469 (M$^+$H, 100%).

EXAMPLE 14

{4-[(5-chloro-1H-indole-2-carbonyl)-amino]-benzyl}-cyclohexyl-dimethyl-ammonium iodide (Cpd 164)

agent was filtered and the solvent was removed in vacuo to yield cyclohexyl-(4-nitro-benzyl)-amine Compound 14a (1.56 g, 67%) as a yellow oil, which was used in the next step without further purification.

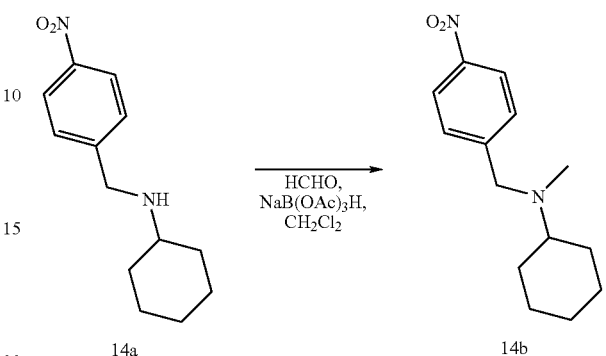

An aqueous solution of formaldehyde (37% solution, 9.6 mmol, 0.8 mL) was added to a solution of Compound 14a (3.41 mmol, 0.8 g) in CH$_2$Cl$_2$, followed by sodium triacetoxyborohydride (7.0 mmol, 1.5 g). The mixture was allowed to stir at r.t. for 2 hrs. The reaction mixture was basified with 2N NaOH solution and was extracted with CH$_2$Cl$_2$. The organic layer was washed with brine, separated and dried over Na$_2$SO$_4$. The drying agent was filtered and the solvent was removed in vacuo. The resulting gummy residue was purified by column chromatography (9:1 EtOAc/MeOH) to yield cyclohexyl-methyl-(4-nitro-benzyl)-amine Compound 14b (0.8 g, 94%) as a yellow oil. MS m/e 249 (M$^+$H, 100%).

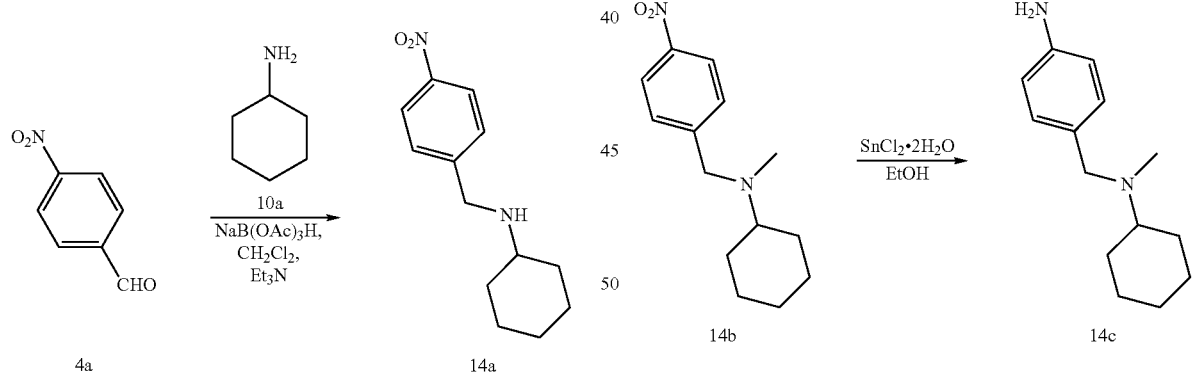

Sodium triacetoxyborohydride (11.0 mmol, 2.33 g) was added to a mixture of 4-nitro-benzaldehyde Compound 4a (10.0 mmol, 1.51 g), cyclohexylamine Compound 10a (10.5 mmol, 1.2 mL) and glacial acetic acid (5 drops) in CH$_2$Cl$_2$ (40 mL) and the resulting suspension was allowed to stir at room temperature for 12 hrs. An aliquot of the reaction mixture showed the formation of product (MS m/e 235, 100%). The reaction mixture was basified with 2N NaOH solution and was extracted with CH$_2$Cl$_2$. The organic layer was washed with brine, separated and dried over Na$_2$SO$_4$. The drying SnCl$_2$.2H$_2$O (16.0 mmol, 3.6 g) was added to a solution of Compound 14b (3.2 mmol, 0.8 g) in EtOH (40 mL) at r.t. The resulting yellow solution was stirred overnight and the solvent was removed in vacuo. The resulting residue was basified with 2N NaOH solution and the aqueous layer was extracted with CH$_2$Cl$_2$ (2×30 mL). The combined organic layers were dried over Na$_2$SO$_4$, filtered and the solvent was removed in vacuo to obtain 4-[(cyclohexyl-methyl-amino)-methyl]-phenylamine Compound 14c (0.69 g, 98%) as a thick yellow oil, which was used in the next step without further purification. MS m/e 219 (M$^+$H, 100%).

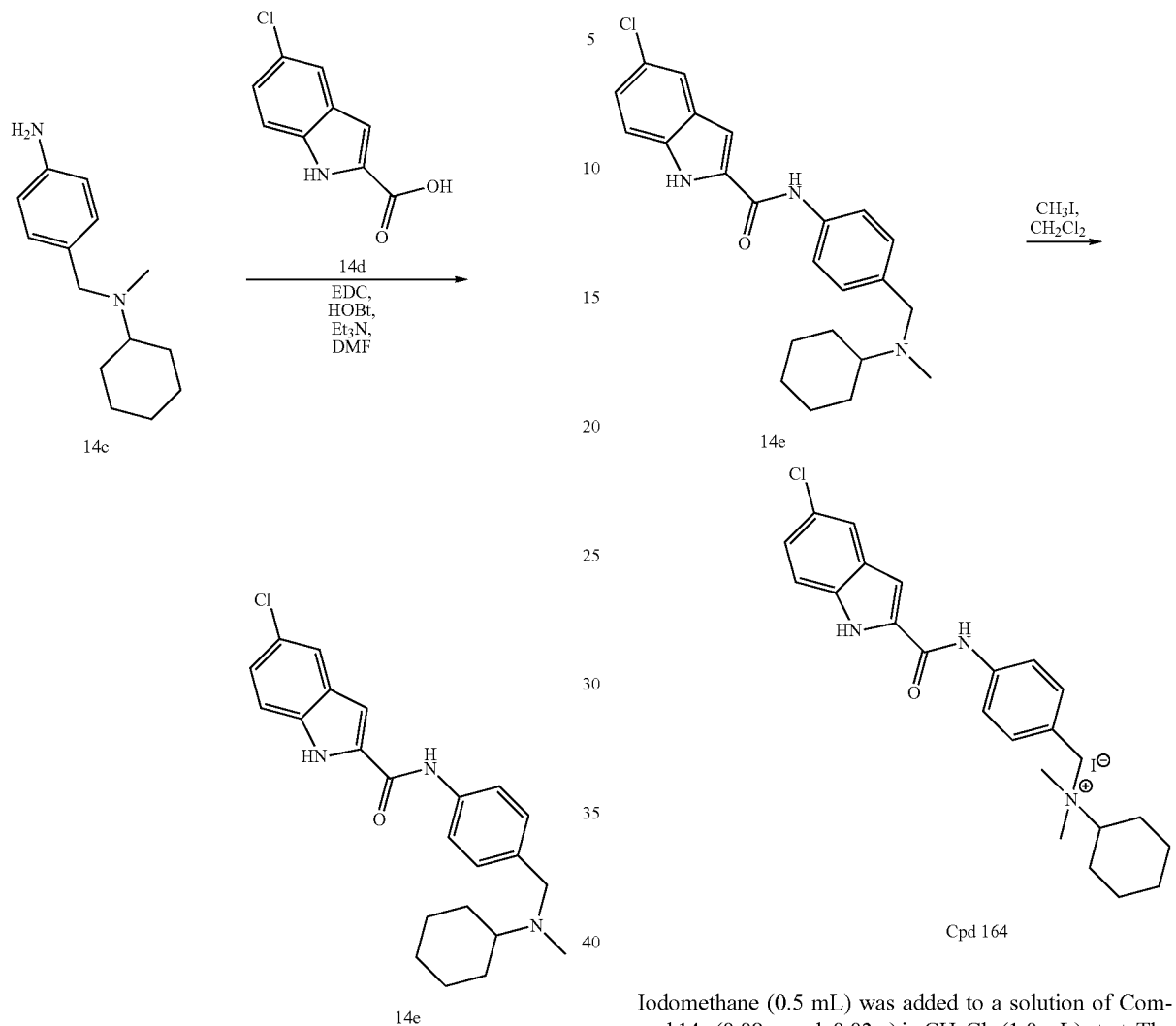

EDCI (0.33 mmol, 0.07 g) was added in one portion to a suspension of Compound 14c (0.25 mmol, 0.05 g), 5-chloro-1H-indole-2-carboxylic acid Compound 14d (0.22 mmol, 0.04 g) and HOBt (0.22 mmol, 0.03 g) in DMF (5.0 mL) at 0° C. The resulting suspension was warmed to r.t. and then a crystal of DMAP and Et₃N (0.65 mmol, 0.1 mL) was added and the reaction mixture was stirred overnight. The resulting orange-yellow suspension was poured in water and was extracted with EtOAc (25 mL). The organic layer was washed with water (2×20 mL) followed by 5% NaOH solution (10 mL) and brine. The organic layer was separated, dried over Na₂SO₄ and filtered. The solvent was removed in vacuo and the resulting residue was purified by preparative TLC (15:1 CH₂Cl₂/MeOH) to yield 5-chloro-1H-indole-2-carboxylic acid {4-[(cyclohexyl-methyl-amino)-methyl]-phenyl}-amide Compound 14e (0.06 g, 68%) as a pale yellow solid. MS m/e 396 (M⁺H, 100%).

Iodomethane (0.5 mL) was added to a solution of Compound 14e (0.08 mmol, 0.03 g) in CH₂Cl₂ (1.0 mL) at r.t. The resulting solution was allowed to stand overnight and a yellow precipitate was observed. The solvent was removed in vacuo and the resulting yellow solid was washed with Et₂O to obtain Compound 167 as a yellow solid (0.04 g, 72%). MS m/e 410 (M⁺H, 100%).

EXAMPLE 15

(2S)-bicyclo[2.2.1]hept-2-yl-{4-[(6-chloro-2H-chromene-3-carbonyl)-amino]-benzyl}-dimethyl-ammonium iodide (Cpd 110)

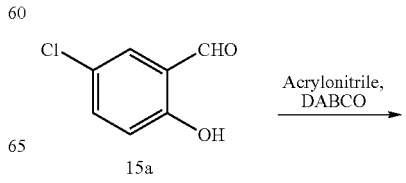

-continued

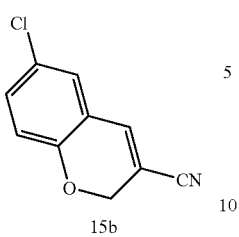
15b 5-chloro-2-hydroxy-benzaldehyde Compound 15a (10.0 mmol, 1.7 g), acrylonitrile (50.0 mmol, 2.14 mL) and DABCO (2.33 mmol, 0.26 g) were mixed together and heated to reflux overnight using an oil bath. After the flask was cooled to room temperature, $Et_2O$ (100 mL) was added and the $Et_2O$ layer was washed with 10% NaOH solution followed by 1N HCl and brine. The organic layer was dried over $MgSO_4$, filtered and the solvent was removed in vacuo to obtain 6-chloro-2H-chromene-3-carbonitrile Compound 15b as a yellow solid (1.42 g, 74%), which was used in the next step without further purification (the preceding was described in Wise, L. et al. *J. Med. Chem.*, 1988, 31, 688).

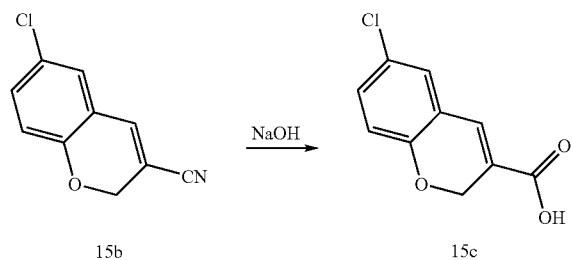

THF (2 mL) and 10% NaOH solution (100 mL) was added to a round bottom flask containing Compound 15b (7.43 mmol, 1.42 g). The solution was heated to reflux for 4 hrs. The flask was immersed in an ice-bath and the solution was acidified by careful addition of conc. HCl. The resulting pale yellow solid was filtered and dried in a vacuum oven to obtain 6-chloro-2H-chromene-3-carboxylic acid Compound 15c (1.02 g, 65%).

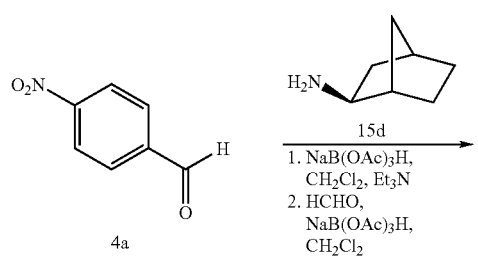

-continued

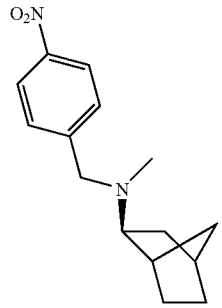
15e

Sodium triacetoxyborohydride (3.5 mmol, 0.75 g) was added to a mixture of 4-nitro-benzaldehyde Compound 4a (2.8 mmol, 0.42 g), (2S)-bicyclo[2.2.1]hept-2-ylamine Compound 15d (3.0 mmol, 0.33 g) and glacial acetic acid (3 drops) in $CH_2Cl_2$ (40 mL). The resulting suspension was allowed to stir at room temperature for 12 hrs. An aliquot of the reaction mixture showed the formation of product (MS m/e 247, 100%). An aqueous solution of formaldehyde (37% solution, 9.6 mmol, 0.8 mL) was added to the reaction mixture followed by sodium triacetoxyborohydride (3.5 mmol, 0.75 g) and the mixture was allowed to stir at r.t. for 2 hrs. The reaction mixture was basified with 2N NaOH solution and was extracted with $CH_2Cl_2$. The organic layer was washed with brine, separated and dried over $Na_2SO_4$. The drying agent was filtered and the solvent was removed in vacuo to obtain (2S)-bicyclo[2.2.1]hept-2-yl-methyl-(4-nitro-benzyl)-amine Compound 15e (0.72 g, 98%) as an orange oil. MS m/e 261 ($M^+H$, 100%), which was used in the next step without further purification.

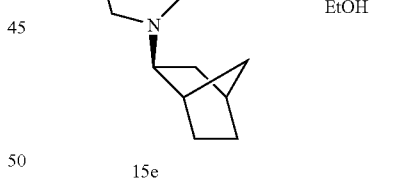

$SnCl_2 \cdot 2H_2O$ (10.4 mmol, 2.35 g) was added to a solution of Compound 15e (2.76 mmol, 0.72 g) in EtOH (25 mL) at r.t.

The resulting yellow solution was stirred for 2 days. The solvent was removed in vacuo and the resulting residue was basified with 2N NaOH solution and the aqueous layer was extracted with CH$_2$Cl$_2$ (2×30 mL). The combined organic layers were dried over Na$_2$SO$_4$, filtered and the solvent was removed in vacuo to obtain (2S)-(4-amino-benzyl)-bicyclo[2.2.1]hept-2-yl-methyl-amine Compound 15f (0.54 g, 85% yield) as a thick yellow oil. MS m/e 231 (M$^+$H, 100%), which was used in the next step without further purification.

CH$_2$Cl$_2$/MeOH) to yield 6-chloro-2H-chromene-3-carboxylic acid (2S)-{4-[(bicyclo[2.2.1]hept-2-yl-methyl-amino)-methyl]-phenyl}-amide Compound 15 h (0.06 g, 61%) as a pale yellow solid. MS m/e 423 (M$^+$H, 100%).

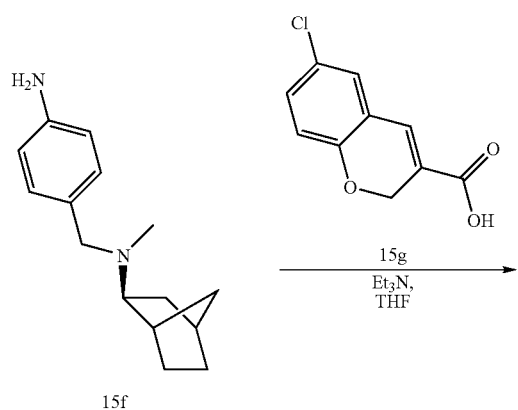

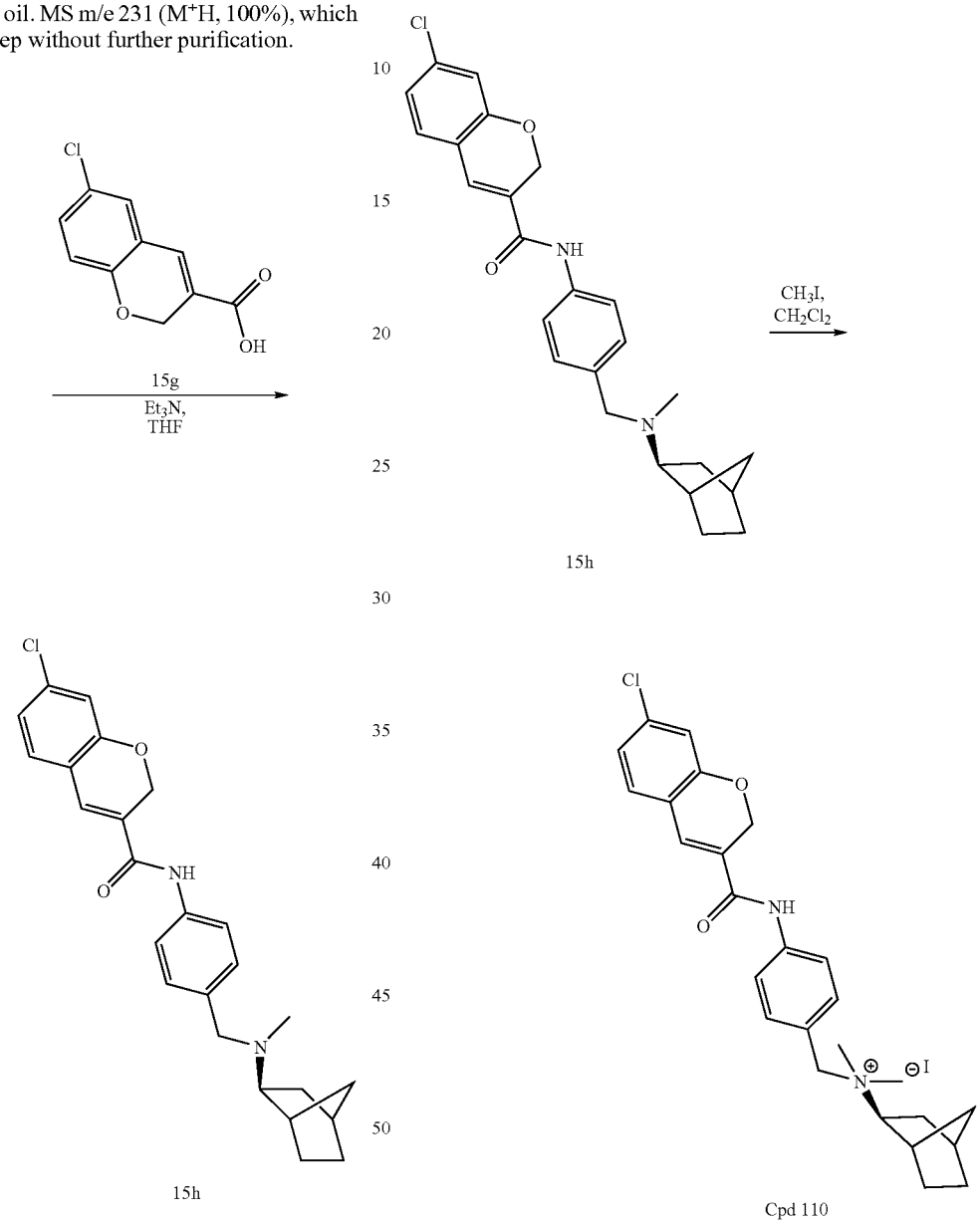

EDCI (0.33 mmol, 0.07 g) was added in one portion to a suspension of Compound 15f (0.24 mmol, 0.06 g), 6-chloro-2H-chromene-3-carboxylic acid Compound 15g (0.22 mmol, 0.04 g) and HOBt (0.22 mmol, 0.03 g) in DMF (5.0 mL) at 0° C. The resulting suspension was warmed to r.t. and then a crystal of DMAP and Et$_3$N (0.65 mmol, 0.1 mL) was added and the reaction mixture was stirred overnight. The orange-yellow suspension was poured in water and was extracted with EtOAc (25 mL). The organic layer was washed with water (2×20 mL) followed by 5% NaOH solution (10 mL) and brine. The organic layer was separated, dried over Na$_2$SO$_4$ and filtered. The solvent was removed in vacuo and the resulting residue was purified by preparative TLC (15:1

Iodomethane (0.5 mL) was added to a solution of Compound 15h (0.08 mmol, 0.03 g) in CH$_2$Cl$_2$ (1.0 mL) at r.t. and the resulting solution was allowed to stand overnight. A yellow precipitate was observed and the solvent was removed in vacuo. The resulting yellow solid was washed with Et$_2$O to obtain Compound 110 (0.05 g, 96%) as a yellow solid. MS m/e 437 (M$^+$H, 100%).

Using the procedure of Example 15 and known appropriate reagents and starting materials, other compounds of the present invention may be prepared including, (MS: Mass Spec data as MS m/e M$^+$H):

| Cpd | Name | MS |
|---|---|---|
| 95 | {4-[(6-bromo-2H-chromene-3-carbonyl)-amino]-benzyl}-dimethyl-(tetrahydro-pyran-4-yl)-ammonium iodide | 471 |
| 96 | {4-[(6-chloro-2H-chromene-3-carbonyl)-amino]-benzyl}-dimethyl-(tetrahydro-pyran-4-yl)-ammonium iodide | 427 |
| 97 | {4-[(6-bromo-2H-chromene-3-carbonyl)-amino]-benzyl}-cyclohexyl-dimethyl-ammonium iodide | 469 |
| 98 | {4-[(6-chloro-2H-chromene-3-carbonyl)-amino]-benzyl}-cyclohexyl-dimethyl-ammonium iodide | 425 |
| 99 | (4-{[(6-bromo-2H-chromene-3-carbonyl)-amino]-methyl}-benzyl)-dimethyl-(tetrahydro-pyran-4-yl)-ammonium iodide | 485 |
| 100 | {4-[(5,7-dichloro-2H-chromene-3-carbonyl)-amino]-benzyl}-dimethyl-(tetrahydro-pyran-4-yl)-ammonium iodide | 461 |
| 101 | cyclohexyl-{4-[(5,7-dichloro-2H-chromene-3-carbonyl)-amino]-benzyl}-dimethyl-ammonium iodide | 459 |
| 102 | {4-[(6,8-dichloro-2H-chromene-3-carbonyl)-amino]-benzyl}-dimethyl-(tetrahydro-pyran-4-yl)-ammonium iodide | 461 |
| 103 | dimethyl-{4-[(6-methyl-2H-chromene-3-carbonyl)-amino]-benzyl}-(tetrahydro-pyran-4-yl)-ammonium iodide | 407 |
| 104 | {4-[(6-methoxy-2H-chromene-3-carbonyl)-amino]-benzyl}-dimethyl-(tetrahydro-pyran-4-yl)-ammonium iodide | 423 |
| 105 | cyclohexyl-dimethyl-{4-[(6-methyl-2H-chromene-3-carbonyl)-amino]-benzyl}-ammonium iodide | 405 |
| 106 | cyclohexyl-{4-[(6-methoxy-2H-chromene-3-carbonyl)-amino]-benzyl}-dimethyl-ammonium iodide | 421 |
| 107 | cyclohexyl-{4-[(6,8-dichloro-2H-chromene-3-carbonyl)-amino]-benzyl}-dimethyl-ammonium iodide | 459 |
| 108 | (2R)-{4-[(6-chloro-2H-chromene-3-carbonyl)-amino]-benzyl}-dimethyl-(tetrahydro-furan-2-ylmethyl)-ammonium iodide | 427 |
| 109 | (2S)-{4-[(6-chloro-2H-chromene-3-carbonyl)-amino]-benzyl}-dimethyl-(tetrahydro-furan-2-ylmethyl)-ammonium iodide | 427 |
| 111 | bicyclo[2.2.1]hept-2-yl-{4-[(6,8-dichloro-2H-chromene-3-carbonyl)-amino]-benzyl}-dimethyl-ammonium iodide | 471 |
| 112 | dimethyl-{4-[(8-methyl-2H-chromene-3-carbonyl)-amino]-benzyl}-(tetrahydro-pyran-4-yl)-ammonium iodide | 407 |
| 113 | cyclohexyl-dimethyl-{4-[(8-methyl-2H-chromene-3-carbonyl)-amino]-benzyl}-ammonium iodide | 405 |
| 114 | {4-[(6-chloro-8-methyl-2H-chromene-3-carbonyl)-amino]-benzyl}-cyclohexyl-dimethyl-ammonium iodide | 439 |
| 115 | {4-[(6-chloro-8-methyl-2H-chromene-3-carbonyl)-amino]-benzyl}-dimethyl-(tetrahydro-pyran-4-yl)-ammonium iodide | 441 |
| 116 | cyclohexyl-{4-[(7,8-dichloro-2H-chromene-3-carbonyl)-amino]-benzyl}-dimethyl-ammonium iodide | 459 |
| 117 | bicyclo[2.2.1]hept-2-yl-{4-[(6-chloro-8-methyl-2H-chromene-3-carbonyl)-amino]-benzyl}-dimethyl-ammonium iodide | 451 |
| 118 | {4-[(6-chloro-8-methyl-2H-chromene-3-carbonyl)-amino]-benzyl}-cycloheptyl-dimethyl-ammonium iodide | 453 |
| 119 | {4-[(6-chloro-8-methyl-2H-chromene-3-carbonyl)-amino]-benzyl}-cyclopentyl-dimethyl-ammonium iodide | 425 |
| 120 | {4-[(6-chloro-8-methyl-2H-chromene-3-carbonyl)-amino]-benzyl}-dimethyl-(tetrahydro-thiophen-3-yl)-ammonium iodide | 443 |
| 121 | (4-{[(6-chloro-8-methyl-2H-chromene-3-carbonyl)-amino]-methyl}-benzyl)-dimethyl-(tetrahydro-pyran-4-yl)-ammonium iodide | 455 |
| 122 | {4-[(6,8-dichloro-2H-chromene-3-carbonyl)-amino]-benzyl}-dimethyl-(tetrahydro-thiophen-3-yl)-ammonium iodide | 463 |
| 123 | cyclohexyl-{4-[(6-fluoro-2H-chromene-3-carbonyl)-amino]-benzyl}-dimethyl-ammonium iodide | 409 |
| 124 | cyclohexyl-{4-[(5-fluoro-2H-chromene-3-carbonyl)-amino]-benzyl}-dimethyl-ammonium iodide | 409 |
| 125 | cyclohexyl-dimethyl-{4-[(6-trifluoromethyl-2H-chromene-3-carbonyl)-amino]-benzyl}-ammonium iodide | 459 |
| 126 | cyclohexyl-{4-[(8-fluoro-2H-chromene-3-carbonyl)-amino]-benzyl}-dimethyl-ammonium iodide | 409 |
| 127 | cyclohexyl-dimethyl-{4-[(7-methyl-2H-chromene-3-carbonyl)-amino]-benzyl}-ammonium iodide | 405 |
| 128 | cyclohexyl-{4-[(7-methoxy-2H-chromene-3-carbonyl)-amino]-benzyl}-dimethyl-ammonium iodide | 421 |
| 129 | {4-[(6-tert-butyl-2H-chromene-3-carbonyl)-amino]-benzyl}-cyclohexyl-dimethyl-ammonium iodide | 447 |
| 130 | dimethyl-(tetrahydro-thiophen-3-yl)-{4-[(6-trifluoromethyl-2H-chromene-3-carbonyl)-amino]-benzyl}-ammonium iodide | 463 |
| 131 | {4-[(5-fluoro-2H-chromene-3-carbonyl)-amino]-benzyl}-dimethyl-(tetrahydro-thiophen-3-yl)-ammonium iodide | 413 |
| 132 | {4-[(6-fluoro-2H-chromene-3-carbonyl)-amino]-benzyl}-dimethyl-(tetrahydro-thiophen-3-yl)-ammonium iodide | 413 |
| 133 | cyclohexyl-dimethyl-{4-[(5-trifluoromethyl-2H-chromene-3-carbonyl)-amino]-benzyl}-ammonium iodide | 459 |

-continued

| Cpd | Name | MS |
|---|---|---|
| 134 | cyclohexyl-dimethyl-{4-[(8-trifluoromethyl-2H-chromene-3-carbonyl)-amino]-benzyl}-ammonium iodide | 459 |
| 135 | {4-[(3H-benzo[f]chromene-2-carbonyl)-amino]-benzyl}-dimethyl-(tetrahydro-pyran-4-yl)-ammonium iodide | 443 |
| 136 | 1-{4-[(3H-benzo[f]chromene-2-carbonyl)-amino]-benzyl}-1-methyl-pyrrolidinium iodide | 399 |
| 137 | {4-[(3H-benzo[f]chromene-2-carbonyl)-amino]-benzyl}-cyclohexyl-dimethyl-ammonium iodide | 441 |
| 138 | {4-[(3H-benzo[f]chromene-2-carbonyl)-amino]-benzyl}-dimethyl-(tetrahydro-thiopyran-4-yl)-ammonium iodide | 459 |
| 139 | 4-{4-[(3H-benzo[f]chromene-2-carbonyl)-amino]-benzyl}-4-methyl-morpholin-4-ium iodide | 415 |
| 140 | {4-[(3H-benzo[f]chromene-2-carbonyl)-amino]-benzyl}-dimethyl-(tetrahydro-pyran-4-ylmethyl)-ammonium iodide | 457 |
| 141 | (4-{[(3H-benzo[f]chromene-2-carbonyl)-amino]-methyl}-benzyl)-dimethyl-(tetrahydro-pyran-4-yl)-ammonium iodide | 457 |

EXAMPLE 16

{4-[(7,8-dichloro-2,3-dihydro-benzo[b]oxepine-4-carbonyl)-amino]-benzyl}-dimethyl-(tetrahydro-pyran-4-yl)-ammonium iodide (Cpd 167)

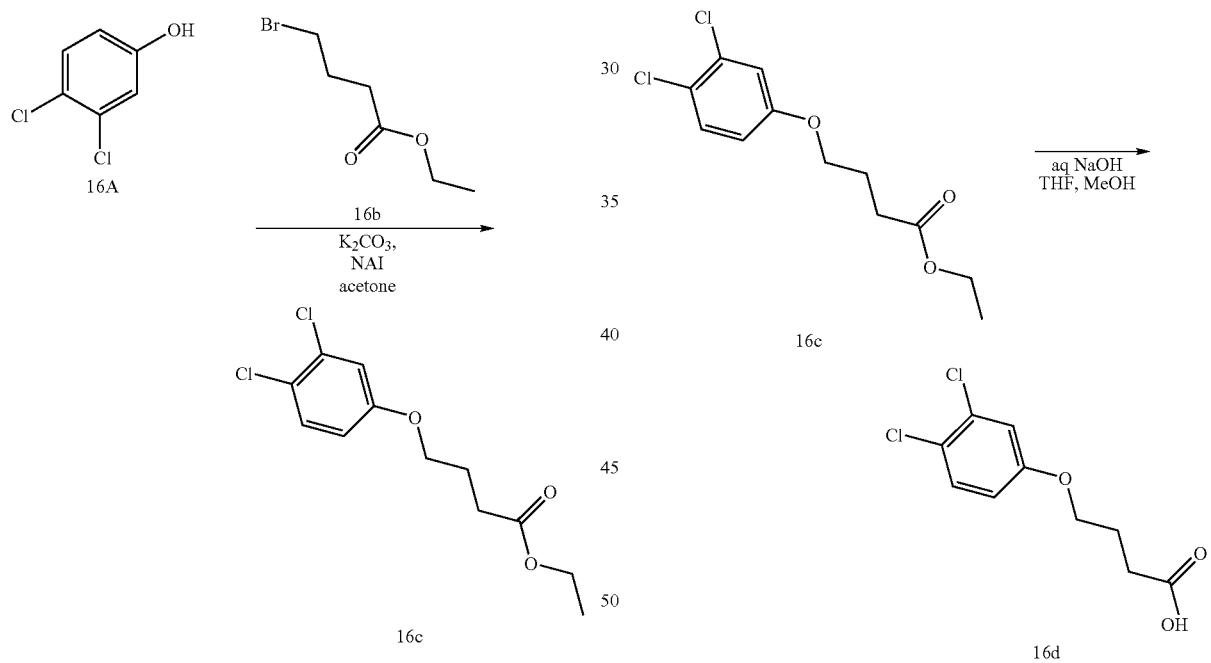

Potassium carbonate (27.5 mmol, 3.75 g) and sodium iodide (0.3333 mmol, 0.0500 g) were added to a reaction mixture of 3,4-dichloro-phenol Compound 16a (30.25 mmol, 4.93 g) and 4-bromo-butyric acid ethyl ester Compound 16b (27.5 mmol, 5.36 g) in acetone (60 mL). The reaction mixture was stirred overnight at room temperature. TLC analysis (4:1 hexane:EtOAc) showed no formation of product. The reaction mixture was refluxed for 3 hrs and TLC analysis (4:1 hexane:EtOAc) showed trace of starting material Compound 16a. The reaction mixture was refluxed overnight, then basified with 1N NaOH solution and extracted with $CH_2Cl_2$. The organics were dried over $MgSO_4$. The drying agent was filtered and the solvent was removed in vacuo to yield 4-(3,4-dichloro-phenoxy)-butyric acid ethyl ester Compound 16c (6.9 g, 90.7%) as a pale pink oil, which was used in the next step without further purification. $^1$H NMR (300 MHz, $CDCl_3$) δ 1.21-1.31 (q, 3H), 2.12-2.25 (m, 2H), 2.45-2.53 (t, 2H), 3.95-4.02 (t, 2H), 4.10-4.20 (q, 2H), 6.71-6.78 (dd, 1H), 6.94-6.96 (d, 1H), 7.28-7.31 (d, 1H).

A 1N NaOH solution (20 mL) was added to a solution of Compound 16c (7.22 mmol, 2.00 g) in THF (20 mL) and MeOH (10 mL). The reaction mixture stirred overnight at room temperature. The THF and MeOH were removed in vacuo and the remaining aqueous solution was acidified with 1N HCl. A precipitate was collected and dried in a vacuum oven overnight to yield 4-(3,4-dichloro-phenoxy)-butyric acid Compound 16d (1.65 g, 92%) as a white solid, which was used in the next step without further purification. $^1$H NMR (300 MHz, $CDCl_3$) δ 2.05-2.18 (m, 2H), 2.52-2.60 (t, 2H), 3.95-4.05 (t, 2H), 6.70-6.79 (dd, 1H), 6.95-7.12 (d, 1H), 7.24-7.35 (t, 1H).

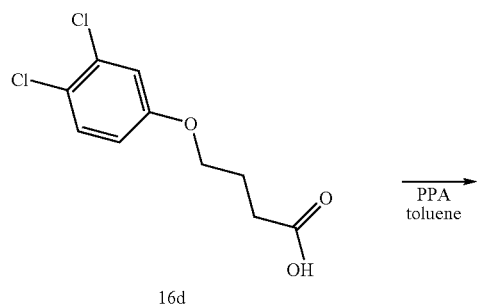

16d

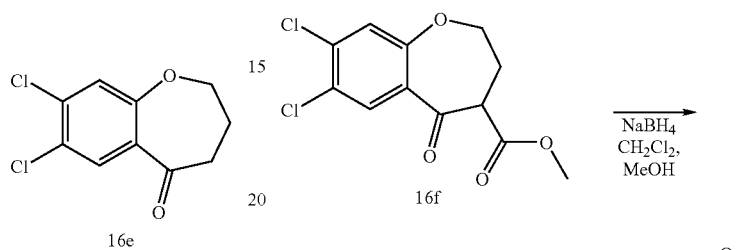

tered. The solvent was removed in vacuo to yield a brown solid (1.27 g) which was taken up in Et$_2$O to yield a tan precipitate. TLC analysis (30% Et$_2$O/Hexane) showed the precipitate to be pure (0.800 g). The remainder of the brown solid was purified by flash column chromatography (30% Et$_2$O/Hexane) to yield 7,8-dichloro-5-oxo-2,3,4,5-tetrahydro-benzo[b]oxepine-4-carboxylic acid methyl ester Compound 16f (0.231 g) as a tan solid. $^1$H NMR of precipitate (300 MHz, CDCl$_3$) δ 2.68-2.75 (t, 2H), 3.85 (s, 3H), 4.32-4.38 (t, 2H), 7.12 (s, 1H), 8.08 (s, 1H), 13.15 (s, 1H).

Polyphosphoric acid (10 equivalents by weight, 51.2 g) was added to a solution of Compound 16d (0.0206 mol, 5.12 g) in toluene (51.5 mL). The mixture was heated to between 95 and 100° C. (bath temperature). The reaction mixture was allowed to cool to room temperature and poured into a beaker of ice water. The aqueous layer was extracted with Et$_2$O. The organics were washed with water and dried with MgSO$_4$. The drying agent was filtered and the solvent was removed in vacuo; yielding a brown solid (3.7 g), which was purified by flash column chromatography (2% EtOAc/Hexane to 10% EtOAc/Hexane) to yield 7,8-dichloro-3,4-dihydro-2H-benzo[b]oxepin-5-one Compound 16e (1.52 g, 32%) as a tan solid.

$^1$H NMR (300 MHz, CDCl$_3$) δ 2.18-2.28 (m, 2H), 2.84-2.95 (t, 2H), 4.21-4.32 (t, 2H), 7.18 (s, 1H), 7.80 (s, 1H).

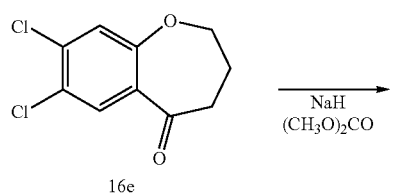

16e

A solution of Compound 16f (1.713 mmol, 0.4951 g) in CH$_2$Cl$_2$ (5 mL) was cooled to −15° C. while stirring. MeOH (0.75 mL) was added, followed by sodium borohydride (2.213 mmol, 0.0837 g) in two portions. The reaction mixture was stirred at −10° C. for 1 hr. TLC analysis (30% Et$_2$O/Hexane) of the reaction mixture showed complete formation of product, with no trace of starting material. The reaction mixture was washed with water and dried over MgSO$_4$. The drying agent was filtered and the solvent was removed in vacuo yielding 7,8-dichloro-5-hydroxy-2,3,4,5-tetrahydrobenzo[b]oxepine-4-carboxylic acid methyl ester Compound 16g (0.488 g, 97.8%) as a yellow oil, which was used in the next step without further purification. $^1$H NMR (400 MHz, CDCl$_3$) δ 2.02-2.14 (m, 3H), 2.30-2.40 (m, 1H), 3.65 (s, 3H), 3.96-4.09 (m, 2H), 4.20-4.28 (m, 1H), 7.35 (s, 1H), 7.56 (s, 1H).

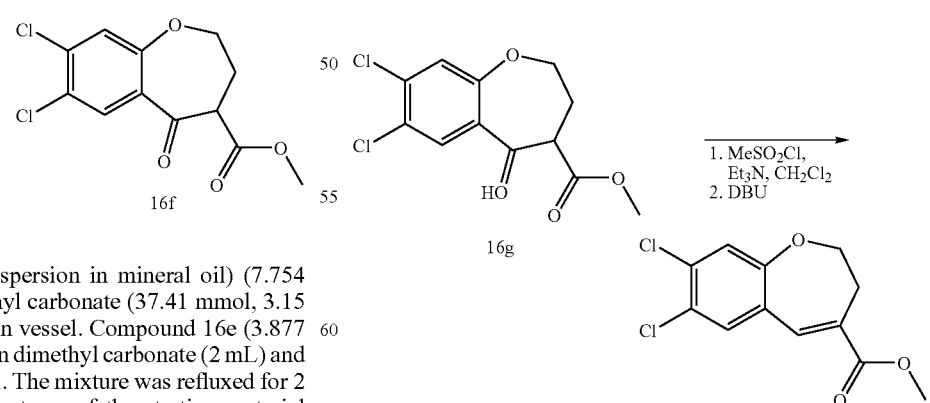

Sodium hydride (60% dispersion in mineral oil) (7.754 mmol, 0.3102 g) and dimethyl carbonate (37.41 mmol, 3.15 mL) were added to a reaction vessel. Compound 16e (3.877 mmol, 1.0 g) was dissolved in dimethyl carbonate (2 mL) and added dropwise to the vessel. The mixture was refluxed for 2 hrs. TLC analysis showed a trace of the starting material Compound 16e and the reaction mixture was allowed to cool and stirred overnight at room temperature. 2N HCl solution (25 mL) was added to the mixture, which was then extracted with EtOAc. The organics were dried over MgSO$_4$ and fil- A solution of Compound 16g (1.676 mmol, 0.4880 g) in CH$_2$Cl$_2$ (8 mL) was cooled to 0° C. while stirring. Triethylamine (5.018 mmol, 0.70 mL) was added, followed by the dropwise addition of methanesulfonyl chloride (2.506 mmol, 0.19 mL). The reaction mixture was allowed to warm to room temperature and stirred overnight. TLC analysis (30% Et$_2$O/Hexane) showed formation of product with no trace of starting material. The mixture was cooled to 0° C. and DBU (6.052 nmol, 0.90 mL) was added dropwise. The reaction mixture was warmed to room temperature and stirred for 30 mins. An aliquot of the reaction mixture was washed with water, dried over MgSO$_4$, filtered and the solvent was removed in vacuo.

NMR analysis showed complete formation of product. The remainder of the mixture was washed with water and dried over MgSO$_4$. The drying agent was filtered and the solvent was removed in vacuo to provide 7,8-dichloro-2,3-dihydro-benzo[b]oxepine-4-carboxylic acid methyl ester Compound 16h (0.408 g, 86.1%) as a yellow oil. $^1$H NMR (400 MHz, CDCl$_3$) δ 2.95-3.00 (t, 2H), 3.82 (s, 3H), 4.22-4.28 (t, 2H), 7.10 (s, 1H), 7.40 (s, 1H), 7.48 (s, 1H).

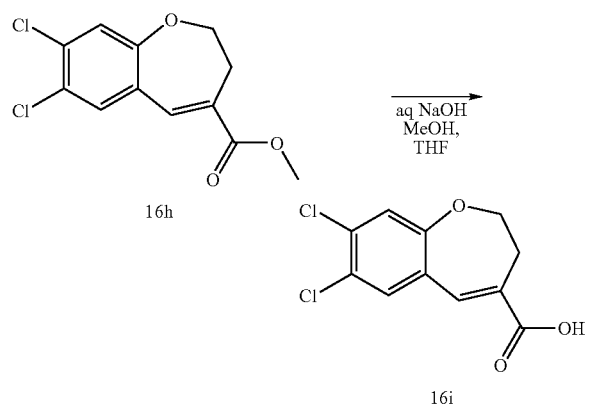

A solution of Compound 16h (1.494 mmol, 0.408 g), THF (20 mL), MeOH (10 mL) and a solution of, 1N NaOH (20 mL) was stirred at room temperature overnight. The solvent was removed in vacuo and the resulting aqueous solution was acidified with concentrated HCl until an off-white precipitate formed. The solid was filtered and dried in a vacuum oven overnight to provide 7,8-dichloro-2,3-dihydro-benzo[b]oxepine-4-carboxylic acid Compound 16i (0.373 g, 96.4%). $^1$H NMR (300 MHz, CDCl$_3$) δ 2.90-3.02 (t, 2H), 4.25-4.31 (t, 2H), 7.10 (s, 1H), 7.42 (s, 1H), 7.51 (s, 1H).

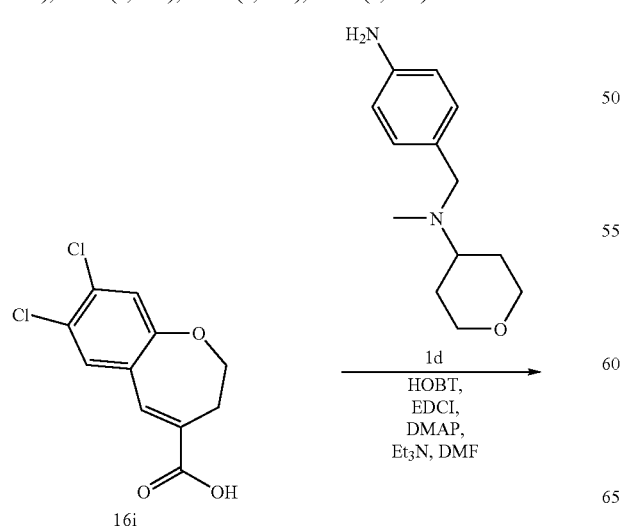

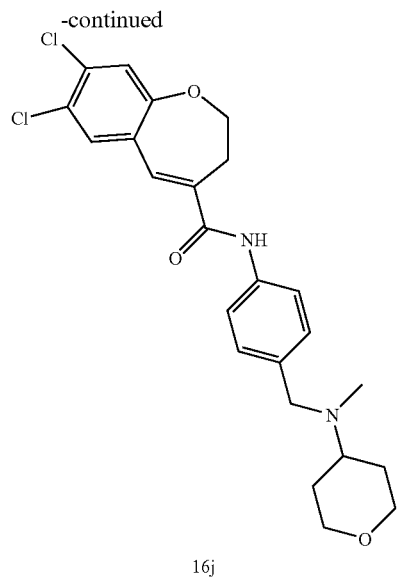

EDCI (0.3293 mmol, 0.0631 g) was added in one portion to a solution of Compound 16i (0.2138 mmol, 0.0554 g), (4-amino-benzyl)-methyl-(tetrahydro-pyran-4-yl)-amine Compound 1d (T10) (0.2459 mmol, 0.0541 g) and HOBT (0.2138 mmol, 0.0289 g) in DMF (6 mL) at 0° C. The mixture was warmed to room temperature and a catalytic amount of DMAP and triethylamine (0.6414 mmol, 0.09 mL) were added. The reaction mixture was stirred overnight at room temperature, then water was added and the mixture was extracted with EtOAc. The organics were washed with water, 1 N NaOH solution and brine and dried over MgSO$_4$. The drying agent was filtered and the solvent was removed in vacuo to yield a yellow oil which was purified by TLC prep plate (9:1 EtoAc:MeOH) to yield 7,8-dichloro-2,3-dihydro-benzo[b]oxepine-4-carboxylic acid (4-{[methyl-(tetrahydro-pyran-4-yl)-amino]-methyl}-phenyl)-amide Compound 16j (0.040 g, 41%) as a yellow solid. MS m/e 461 (M$^+$H, 90%), (M$^+$Na, 100%); $^1$H NMR (300 MHz, CDCl$_3$) δ 1.58-1.80 (m, 5H), 2.16 (s, 3H), 2.58-2.69 (m, 1H), 3.00-3.08 (m, 2H), 3.30-3.41 (m, 2H), 3.52 (s, 2H), 4.00-4.08 (m, 2H), 4.25-4.31 (m, 2H), 7.02 (s, 1H), 7.10 (s, 1H), 7.28-7.38 (t, 3H), 7.50-7.55 (d, 2H).

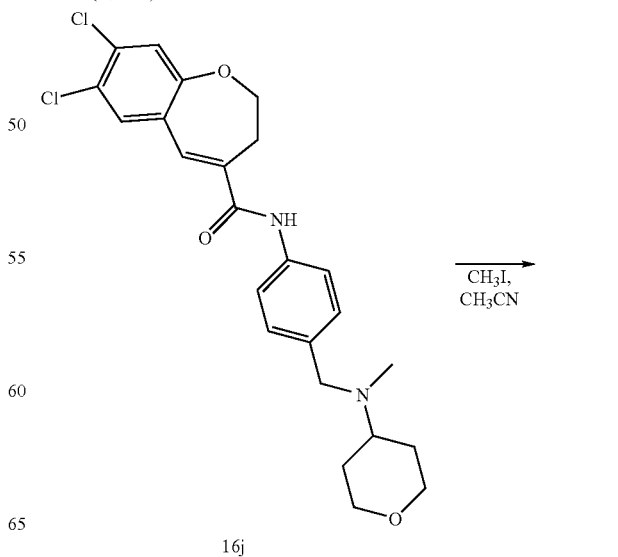

-continued

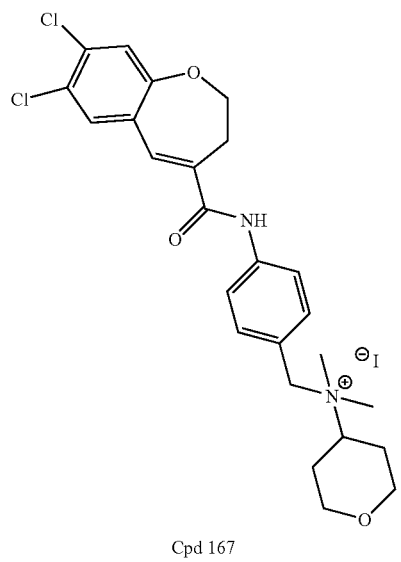

Cpd 167

Iodomethane (0.0161 mol, 1.0 mL) was added to a solution of Compound 16j (0.0433 mmol, 0.020 g) in acetonitrile (2 mL), acetone (2 drops) and dichloromethane (2 drops) at room temperature and the resulting solution was stirred overnight. The solvent was removed in vacuo and the resulting orange solid was washed with $Et_2O$ and dried in a vacuum oven for 12 hrs to provide Compound 167 (0.0123 g, 78.5%). MS m/e 475 ($M^+H$, 100%); MS m/e 477 ($M^+H$, 75%).

Using the procedure of Example 16 and known appropriate reagents and starting materials, other compounds of the present invention may be prepared including, (MS: Mass Spec data as MS m/e $M^+H$):

Biological Activity

Compound of the invention were subjected to various representative biological tests. The results of these tests are intended to illustrate the invention in a non-limiting fashion.

EXAMPLE 17

MCP-1 Receptor Binding Assay in THP-1 Cells

THP-1 cells were obtained from American Type Culture Collection (Manassas, Va., USA). The THP-1 cells were grown in RPMI-1640 supplemented with 10% fetal bovine serum in a humidified 5% $CO_2$ atmosphere at 37° C. The cell density was maintained between $0.5 \times 10^6$ cells/mL.

THP-1 cells were incubated with 0.5 nM $^{125}I$ labeled MCP-1 (Perkin-Elmer Life Sciences, Inc. Boston, Mass.) in the presence of varying concentrations of either unlabeled MCP-1 (R&D Systems, Minneapolis, Minn.) or test compound for 2 hours at 30° C. in a 96 well plate. Cells were then harvested onto a filter plate, dried, and 20 μL of Microscint 20 was added to each well. Plates were counted in a TopCount NXT, Microplate Scintillation & Luminescence Counter (Perkin-Elmer Life Sciences, Inc. Boston, Mass.). Blank values (buffer only) were subtracted from all values and drug treated values were compared to vehicle treated values. 1 μM cold MCP-1 was used for nonspecific binding.

Table 1 lists $IC_{50}$ values for inhibition of MCP-1 binding to CCR2 obtained for test compounds of the invention.

Table 2 lists inhibition values obtained for test compounds for MCP-1 binding to CCR2. The inhibition values (%) were obtained at a test concentration of 25 μM, unless indicated otherwise.

| Cpd | Name | MS |
|---|---|---|
| 142 | (4-{[(3-bromo-8,9-dihydro-7H-benzocycloheptene-6-carbonyl)-amino]-methyl}-benzyl)-dimethyl-(tetrahydro-pyran-4-yl)-ammonium iodide | 497 |
| 143 | {4-[(3-bromo-8,9-dihydro-7H-benzocycloheptene-6-carbonyl)-amino]-benzyl}-dimethyl-(tetrahydro-pyran-4-yl)-ammonium iodide | 483 |
| 144 | {4-[(3-bromo-8,9-dihydro-7H-benzocycloheptene-6-carbonyl)-amino]-benzyl}-cyclohexyl-dimethyl-ammonium iodide | 481 |
| 145 | 1-{4-[(8,9-dihydro-7H-benzocycloheptene-6-carbonyl)-amino]-benzyl}-1-methyl-pyrrolidinium iodide | 361 |
| 146 | cyclohexyl-{4-[(8,9-dihydro-7H-benzocycloheptene-6-carbonyl)-amino]-benzyl}-dimethyl-ammonium iodide | 403 |
| 147 | {4-[(8,9-dihydro-7H-benzocycloheptene-6-carbonyl)-amino]-benzyl}-dimethyl-(tetrahydro-pyran-4-yl)-ammonium iodide | 405 |
| 148 | (4-{[(8,9-dihydro-7H-benzocycloheptene-6-carbonyl)-amino]-methyl}-benzyl)-dimethyl-(tetrahydro-pyran-4-yl)-ammonium iodide | 419 |
| 168 | cyclohexyl-{4-[(7,8-dichloro-2,3-dihydro-benzo[b]oxepine-4-carbonyl)-amino]-benzyl}-dimethyl-ammonium iodide | 473 |
| 169 | bicyclo[2.2.1]hept-2-yl-{4-[(7,8-dichloro-2,3-dihydro-benzo[b]oxepine-4-carbonyl)-amino]-benzyl}-dimethyl-ammonium iodide | 485 |
| 170 | (4-{[(7,8-dichloro-2,3-dihydro-benzo[b]oxepine-4-carbonyl)-amino]-methyl}-benzyl)-dimethyl-(tetrahydro-pyran-4-yl)-ammonium iodide | 489 |
| 171 | {4-[(7,8-dichloro-2,3-dihydro-benzo[b]oxepine-4-carbonyl)-amino]-benzyl}-dimethyl-(tetrahydro-thiophen-3-yl)-ammonium iodide | 477 |

TABLE 1

Mean Ligand Binding (IC$_{50}$ μM)

| Cpd | IC$_{50}$ (μM) |
|---|---|
| 1 | 2.3 |
| 2 | 5.5 |
| 3 | 4.3 |
| 4 | 3.1 |
| 5 | 8.3 |
| 6 | 5 |
| 7 | 6.3 |
| 10 | 6.6 |
| 11 | 3.1 |
| 14 | 0.06 |
| 15 | 2 |
| 16 | 0.85 |
| 17 | 0.005; 0.01; 0.009 |
| 18 | 1.8 |
| 19 | 0.005 |
| 20 | 0.16 |
| 21 | 0.15 |
| 22 | 1.6 |
| 23 | 0.9 |
| 24 | 0.29; 0.19 |
| 26 | 0.28 |
| 27 | 0.75 |
| 28 | 0.46 |
| 29 | 0.33 |
| 30 | 4.2 |
| 31 | 11.4 |
| 32 | 3.4 |
| 33 | 0.4 |
| 34 | 2.4 |
| 35 | 0.4 |
| 37 | 10.2 |
| 38 | 5 |
| 39 | 6.4 |
| 40 | 1.6 |
| 42 | 5.7 |
| 43 | 0.34 |
| 44 | 14.6 |
| 45 | 0.26 |
| 46 | 1.3 |
| 47 | 3.7 |
| 48 | 8.4 |
| 49 | 11.9 |
| 50 | 2.6 |
| 51 | 2.7 |
| 52 | 2.6 |
| 53 | 3.2 |
| 55 | 5.4 |
| 56 | 11.8 |
| 57 | 13.3 |
| 59 | 10 |
| 61 | 2.7 |
| 63 | 3.5 |
| 66 | 1.7 |
| 67 | 2.5 |
| 68 | 1.5 |
| 69 | 6.4 |
| 70 | 0.11 |
| 71 | 0.17; 0.32 |
| 72 | 0.58 |
| 73 | 0.44 |
| 74 | 1.5 |
| 75 | 0.02 |
| 76 | 0.16 |
| 78 | 13.4 |
| 79 | 0.31 |
| 80 | 0.03 |
| 81 | 3 |
| 82 | 0.05 |
| 83 | 1.2 |
| 84 | 3.2 |
| 85 | 5.2 |
| 86 | 6 |
| 87 | 3.8 |
| 88 | 0.87 |
| 90 | 0.22 |
| 91 | 4.1 |
| 93 | 0.9 |
| 94 | 1.3 |
| 95 | 0.18 |
| 96 | 0.11 |
| 97 | 0.45 |
| 98 | 0.27 |
| 100 | 0.52 |
| 101 | 1.1 |
| 102 | 0.19 |
| 103 | 0.82 |
| 104 | 1.9 |
| 105 | 0.32 |
| 106 | 1.1 |
| 107 | 0.17 |
| 108 | 3.1 |
| 109 | 5.3 |
| 110 | 0.32 |
| 111 | 2 |
| 112 | 0.15 |
| 113 | 0.53 |
| 114 | 0.06 |
| 115 | 0.05 |
| 116 | 0.6 |
| 117 | 0.12 |
| 118 | 0.2 |
| 119 | 0.1 |
| 120 | 0.03 |
| 122 | 0.58 |
| 126 | 0.91 |
| 127 | 0.08 |
| 128 | 0.6 |
| 129 | 0.15 |
| 130 | 0.3 |
| 131 | 0.33 |
| 132 | 0.13 |
| 133 | 3.3 |
| 134 | 0.47 |
| 135 | 0.91 |
| 136 | 4.6 |
| 137 | 0.08 |
| 138 | 2.4 |
| 139 | 9.8 |
| 140 | 1 |
| 143 | 0.007 |
| 144 | 0.33 |
| 146 | 0.71 |
| 147 | 1.2 |
| 151 | 0.26 |
| 152 | 1.6 |
| 153 | 2.1 |
| 154 | 4.6 |
| 155 | 0.49 |
| 156 | 0.18 |
| 157 | 0.69 |
| 158 | 0.4 |
| 159 | 0.19 |
| 160 | 0.29 |
| 162 | 1.6 |
| 163 | 0.62 |
| 164 | 0.2 |
| 165 | 3.3 |
| 166 | 0.11 |
| 167 | 0.24 |
| 168 | 1 |
| 169 | 0.24 |
| 171 | 0.56 |
| 173 | 8.1 |
| 175 | 1.5 |
| 176 | 0.26 |
| 177 | 0.17 |
| 178 | 8.8 |

TABLE 2

| Cpd | % Inhibition Ligand Binding<br>% Inhibition |
|---|---|
| 8 | 34 |
| 9 | 65 |
| 12 | 38 |
| 13 | 29 |
| 25 | 15 |
| 36 | 49 |
| 41 | 87 |
| 58 | 53 |
| 60 | 20 |
| 62 | 9 |
| 64 | 63 |
| 65 | 61 |
| 77 | 53 |
| 89 | 29 |
| 92 | 54 |
| 99 | 34 |
| 121 | 37 |
| 123 | 100 |
| 124 | 100 |
| 125 | 100 |
| 141 | −21 |
| 142 | −18 |
| 145 | 36 |
| 148 | 7 |
| 149 | 58 |
| 150 | 27 |
| 161 | 33 |
| 170 | 36 |
| 172 | 17 |
| 174 | 52 |

EXAMPLE 18

MCP-1 Induced Chemotaxis in THP-1 Cells

MCP-1 induced chemotaxis was run in a 24-well chemotaxis chamber. MCP-1 (0.01 μg/mL) was added to the lower chamber and 100 μL of THP-1 cells (1×10$^7$ cell/mL) was added to the top chamber. Varying concentrations of test compound were added to the top and bottom chambers. Cells were allowed to chemotax for 3 hours at 37° C. and 5% $CO_2$. An aliquot of the cells which had migrated to the bottom chamber was taken and counted then compared to vehicle.

Test compounds of the invention inhibited MCP-1 induced chemotaxis with $IC_{50}$ values of from about 10 μM to about 1 nM.

EXAMPLE 19

MCP-1 Induced Calcium Mobilization in THP-1 Cells

THP-1 cells were plated at a density of 8×10$^5$ cells/ml (100 μL/well) into poly-D lysine coated clear bottom, black 96 well plates. The cells were loaded with 5 μM fluo-3 for 45 minutes. The fluo-3 was washed off and cells were incubated with varying concentrations of test compound for 15 minutes. The change in $[Ca^{2+}]_i$ upon addition of 0.2 μM MCP-1 is determined using FLIPR and compared to vehicle.

Test compounds of the invention inhibited MCP-1 induced influx of $Ca^{2+}$ ions with $IC_{50}$ values of from about 10 μM to about 1 nM.

EXAMPLE 20

Inhibition of Uveitis in Mice

The lipopolysaccharide (LPS bacterial endotoxin) induced uveitis mouse model is used to test a compound of the invention for inhibition of MCP-1 induced inflammation in the anterior of the eye (Tuaillon N, Shen de F, Berger R B, Lu B, Rollins B J and Chan CC, MCP-1 expression in endotoxin-induced uveitis, *Invest. Ophthalmol. Vis. Sci.*, 2002 May, 43(5): 1493-8).

After intraocular injection directly into the anterior chamber of the eye with LPS, a measurable amount of MCP-1 is found in the eye's aqueous humor within a few hours. The degree of inflammation is quantified by counting the number of leukocytes within the aqueous humor of the anterior chamber (including a differential count), determining the protein concentration in the aqueous humor and confirming the inhibition of inflammation by histological examination.

Procedure

A test compound was dissolved in saline (5 mg/mL); and 10 μL (50 μg) was applied topically to the injected eye at 0, 4, and 8 hr relative to the LPS injection. The control group was treated topically with a saline vehicle (no test compound). One hour after the last dose of the compound (i.e., 9 hours post-injection), the mice were sacrificed and leukocyte, neutrophil and mononuclear cell counts and protein concentration inside the eye were measured.

Results

In two trials, the compound inhibited leukocyte infiltration by 66% (±1%). The accumulation of protein was inhibited by 52% (±14%). Cell differential counts indicated that neutrophil influx into the eye was inhibited by 67% while mononuclear cell influx was inhibited by 40%. Histological examination confirmed the inhibition of cellular influx.

Based on the binding data for inhibition of MCP-1 induced inflammation and the data for inhibition of MCP-1 induced anterior uveitis, an effective dose per day for a compound of the invention for treating anterior uveitis is in a range of from about 50 μg to about 0.5 ng. An embodiment of an effective dose for a compound of the invention for the treatment of anterior uveitis is from about 5 μg to about 0.5 ng. Another embodiment of an effective dose for such treatment is from about 1 μg to about 1 ng. Another embodiment of an effective dose is from about 0.5 μg to about 1 ng. An embodiment of an effective dose is also from about 0.1 μg to about 1 ng.

EXAMPLE 21

Inhibition of Ovalbumin (Ova)-Induced Asthma in Mice

Test compounds of the present invention were active in two different models of ovalbumin (OVA)-induced asthma in mice.

Mast Cell-Dependent Model

Mice were sensitized by i.p. injection with OVA in saline (10 μg) on alternate days (Day 0, 2, 4, 6, 8, 10, 12). Groups of mice were each challenged by intranasal injection of OVA (Day 40, 43, 46). Compound 17 was administered by i.p. injection (30 mg/kg) on consecutive days (Day 42, 43, 44, 45, 46). Compared to vehicle, leukocyte influx was inhibited by 95% and 55% (in two separate assays), LTC$_4$ influx was inhibited by 90% and IL-4 influx was inhibited by 85%.

Mast Cell-Independent Model

Mice were sensitized by i.p. injection of OVA emulsified in adjuvant (Day 1 and 14). Groups of mice were each challenged by intranasal injection of OVA (Day 25, 26, 27). Compound 17 was administered by i.p. injection (10 and 30 mg/kg) before each intranasal challenge (Day 25, 26, 27). Compared to vehicle, leukocyte influx was dose-dependently inhibited by 40% and 70%, respectively.

EXAMPLE 22

Inhibition of Ovalbumin-induced Allergic Rhinitis in Mice

BALB/c mice were sensitized by i.p. injection of OVA emulsified in alum (Day 0, 5, 14, 21). Groups of mice were each challenged by intranasal injection of OVA (Day 22-35, 38).

Control group mice received an equal volume of vehicle by intranasal injection. Nasal symptoms (number of sneezes and episodes of nose rubbing by the front paws) were counted during the 5 min period following the last intranasal injection (Day 38).

Prophylactic Effect

Compound 17 (in PBS) was administered by intranasal injection (10 and 30 μg/nostril) to both nostrils twice daily 1 hr and 6 hrs prior to intranasal challenge (Days 22-35), once per day prior to intranasal challenge (Days 36, 37) then 1 hr and 6 hrs prior to intranasal challenge (Day 38). The histamine receptor antagonist Astelin® was used as a positive control.

Compared to vehicle, Compound 17 dose-dependently inhibited nasal symptoms by 64/57% (sneezing/rubbing) and 82/71% (sneezing/rubbing), respectively. Compared to vehicle, the positive control inhibited nasal symptoms by 51/89% (sneezing/rubbing).

Therapeutic Effect

The dosing of Compound 17 was delayed until the symptoms of rhinitis had appeared (Day 29). Compound 17 (in PBS) was then administered by intranasal injection (10 μg/nostril) to both nostrils four times per day prior to intranasal challenge (Days 29-38). The anti-histamine Pyralimine and the mast cell-stabilizing agent Ketotifen were used as positive controls.

Compared to vehicle, Compound 17 inhibited nasal symptoms by 0/42% (sneezing/rubbing). Compared to vehicle, Pyralimine and Ketotifen inhibited nasal symptoms by 60/85% (sneezing/rubbing) and 50/81% (sneezing/rubbing), respectively.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound which is a quaternary ammonium salt, the cation having Formula (I)

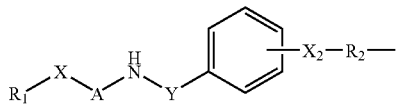

or pharmaceutically acceptable forms of said compound thereof, wherein

A is carbonyl, thiocarbonyl or sulfonyl;

X is a bond —or —CH═CH—;

$R_1$ is selected from
(1). aryl optionally substituted by one or more lower alkyl, —(CH$_2$)$_n$—CF$_3$, lower alkoxy, alkoxycarbonyl, cyano, halogen or phenyl optionally substituted by lower alkyl, —(CH$_2$)$_n$—CF3, lower alkoxy, alkoxycarbonyl, cyano or halogen; or
(2). C$_5$-C$_{15}$ cycloalkyl optionally substituted by one or more lower alkyl, —(CH$_2$)$_n$—CF$_3$, lower alkoxy, aryl, halogen-substituted aryl, alkoxycarbonyl, cyano or halogen;

n is 0, 1, 2, 3, or 4;

Y is a bond or —CH$_2$—;

$X_2$ is —(CH$_2$)$_m$— wherein m is 1 or 2;

$R_2$ is —N$^+$(R4R$_5$)—ZR$_3$;

Z is —(CH$_2$)$_p$— wherein p is 0, 1 or 2;

$R_3$ is selected from
(1). aryl optionally substituted by one or more lower alkyl, —(CH$_2$)$_n$—CF$_3$, lower alkoxy, aryl, halogen-substituted aryl, alkoxycarbonyl, cyano or halogen;
(2). C$_5$-C$_{15}$ cycloalkyl optionally substituted with one or more lower alkyl, —(CH$_2$)$_n$—CF$_3$, lower alkoxy, aryl, halogen-substituted aryl, alkoxycarbonyl, cyano or halogen; or
(3). heterocyclyl optionally substituted with one or more lower alkyl, —(CH$_2$)$_n$—CF$_3$, lower alkoxy, aryl, halogen-substituted aryl, alkoxycarbonyl, cyano or halogen; wherein, when heterocyclyl is attached via a carbon atom ring member and a heteroatom ring member is adjacent to said carbon atom, then p is 1 or 2;

$R_4$ and $R_5$ are each individually lower alkyl or lower alkenyl; or alternatively, $R_4$ and $R_5$ combine with the nitrogen atom of Formula (I) to form a heterocyclyl ring of 5 to 9 total ring atoms optionally containing one of an oxygen or sulfur ring atom, wherein the heterocyclyl ring nitrogen atom is substituted with one of lower alkyl or lower alkenyl to form a quaternary salt, and wherein —ZR$_3$ is absent and the heterocyclyl ring is optionally substituted with aryl optionally substituted with one or more lower alkyl, —(CH$_2$)$_n$—CF$_3$, lower alkoxy, aryl, halogen-substituted aryl, alkoxycarbonyl, cyano or halogen, said heterocyclyl for ring R$_3$ being tetrahydropyran, tetrahydrofuran, tetrahydrothiophene, tetrahydrothiopyran, pyrrolidine, morpholine, thiomorpholine, piperidine, thiophene or piperazine.

2. The compound of claim 1, wherein A is carbonyl; X is a bond; $R_1$ is selected from aryl substituted by one or more lower alkyl or halogen, and C$_5$-C$_{15}$ cycloalkyl optionally substituted by one or more halogen, Y is a bond; $X_2$ is —CH$_2$—; $R_2$ is —N$^+$(R$_4$R$_5$)—R$_3$; R$_3$ is selected from C$_5$-C$_{15}$ cycloalkyl or heterocyclyl and R$_4$ and R$_5$ are each individually lower alkyl.

3. The compound of claim 1, wherein A is carbonyl, X is a bond, $R_1$ is aryl optionally substituted by one or more halogen, Y is a bond, $X_2$ is —$CH_2$—, $R_2$ is —$N^+(R_4R_5)$—$R_3$, $R_3$ is heterocyclyl and $R_4$ and $R_5$ are each individually lower alkyl.

4. The compound of claim 1, wherein A is carbonyl.

5. The compound of claim 1, wherein $R_1$ is selected from (1). aryl optionally substituted by one or more lower alkyl, —$(CH_2)_n$—$CF_3$, lower alkoxy, cyano, halogen or phenyl optionally substituted by lower alkyl, —$(CH_2)_n$—$CF_3$, lower alkoxy, cyano or halogen; and (2). $C_5$-$C_{15}$ cycloalkyl optionally substituted by one or more lower alkyl, —$(CH_2)_n$—$CF_3$, lower alkoxy, cyano or halogen.

6. The compound of claim 1, wherein n is 0.

7. The compound of claim 1, wherein p is 0 or 1.

8. The compound of claim 1, wherein $R_3$ is $C_5$-$C_{15}$ cycloalkyl or heterocyclyl;

wherein, when heterocyclyl is attached via a carbon atom ring member and a heteroatom ring member is adjacent to said carbon atom, then p is 1.

9. The compound of claim 1, wherein $R_4$ and $R_5$ are each individually lower alkyl or lower allyl.

10. The compound of claim 1, wherein $R_4$ and $R_5$ combine with the nitrogen atom of Formula (I) to form a heterocyclyl ring of 5 to 9 total ring atoms optionally containing one of an oxygen or sulfur ring atom, wherein the heterocyclyl ring nitrogen atom is substituted with lower alkyl to form a quaternary salt, and wherein —$ZR_3$ is absent and the heterocyclyl ring is optionally substituted with one or more lower alkyl, —$(CH_2)_n$—$CF_3$, lower alkoxy, cyano or halogen.

11. The compound of claim 1, wherein $R_4$ and $R_5$ combine with the nitrogen atom of Formula (I) to form a heterocyclyl ring of 5 to 9 total ring atoms optionally containing one of an oxygen or sulfur ring atom, wherein the heterocyclyl ring nitrogen atom is substituted with lower alkyl to form a quaternary salt, and wherein —$ZR_3$ is absent and the heterocyclyl ring is optionally substituted with aryl optionally substituted with lower alkoxy.

12. A compound which is a quaternary ammonium salt, or pharmaceutically acceptable forms thereof, the cation of said compound selected from

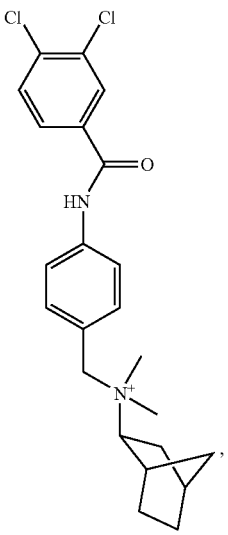

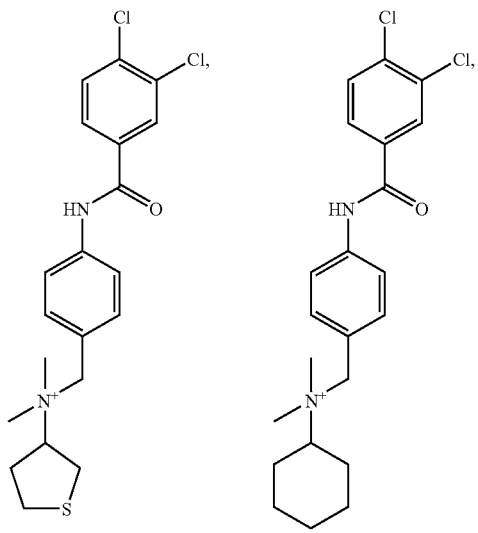

-continued

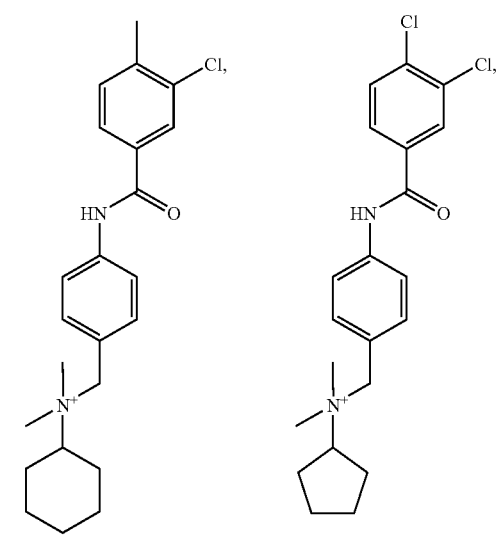

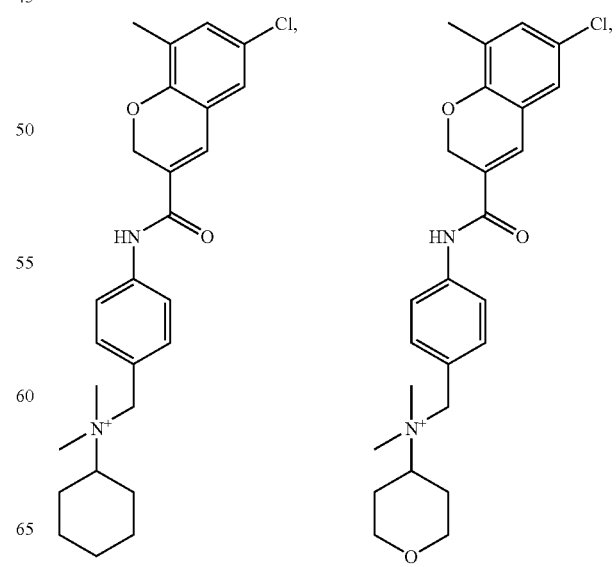

-continued

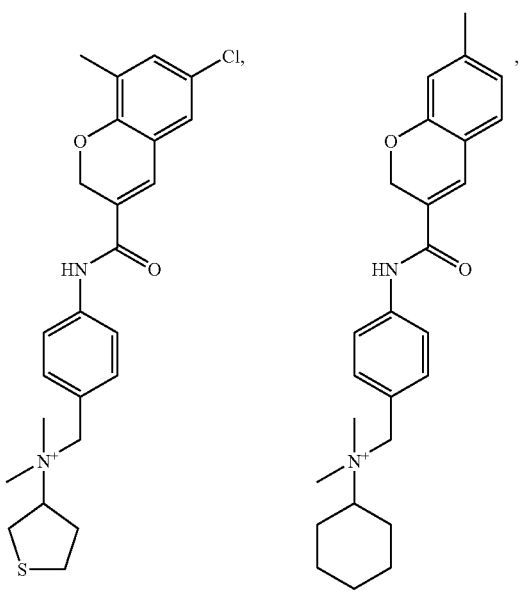

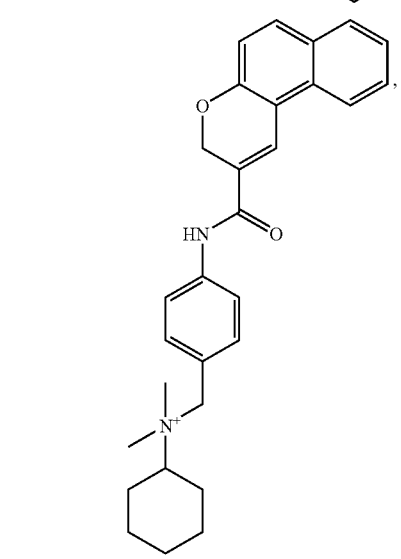

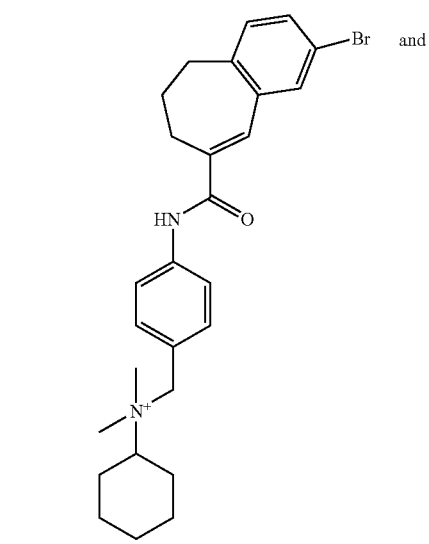

-continued

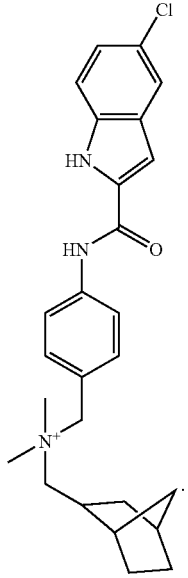

13. A composition comprising an effective amount of the compound of claim 1 and a pharmaceutically acceptable carrier.

14. The composition of claim 13 selected from a topically applied composition, an intranasally applied composition or an ocularly applied composition.

15. A process for preparing the composition of claim 13 comprising the step of admixing said compound with a pharmaceutically acceptable carrier.

16. A method for treating CCR2 mediated inflammation in a subject in need thereof comprising administering to the subject an effective amount of the compound of claim 1 or pharmaceutically acceptable form of said compound.

17. The method of claim 16 wherein the effective amount is from about 0.001 mg/kg/day to about 300 mg/kg/day.

18. The method of claim 16, wherein the CCR2 mediated inflammation is associated with elevated MCP-1 expression or MCP-1 over expression, or is an inflammatory condition that accompanies syndromes, disorders or diseases associated with elevated MCP-1 expression or MCP-1 overexpression.

19. The method of claim 16, wherein the CCR2 mediated inflammation is associated with ophthalmic disorders, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, diabetes and diabetic complications, diabetic nephropathy, diabetic retinopathy, diabetic retinitis, diabetic microangiopathy, tuberculosis, chronic obstructive pulmonary disease, sarcoidosis, invasive staphyloccocia, inflammation after cataract surgery, allergic rhinitis, allergic conjunctivitis, chronic utricaria, asthma, periodontal diseases, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma or Hodgkin's disease.

20. The method of claim 16, wherein the method comprises treating CCR2 mediated inflammation associated with ophthalmic disorders, rheumatoid arthritis, psoriasis, psoriatic arthritis, atopic dermatitis, chronic obstructive pulmonary disease, allergic rhinitis, asthma, or periodontal diseases in a subject in need thereof by administering to the subject an effective amount of said compound or pharmaceutically acceptable form of said compound.

21. The method of claim 20, wherein the ophthalmic disorder is selected from uveitis or allergic conjunctivitis and the periodontal disease is selected from periodontitis and gingivitis.

22. The method of claim 21, wherein uveitis is acute, recurring or chronic uveitis.

23. The method of claim 21, wherein uveitis is anterior uveitis, intermediate uveitis, posterior uveitis or panuveitis.

24. The method of claim 16, wherein the method comprises treating CCR2 mediated inflammation associated with acute uveitis, recurring uveitis, chronic uveitis, allergic conjunctivitis, rheumatoid arthritis, psoriasis, psoriatic arthritis, atopic dermatitis, chronic obstructive pulmonary disease, allergic rhinitis, asthma, periodontitis or gingivitis in a subject in need thereof by administering to the subject an effective amount of said compound or pharmaceutically acceptable form of said compound.

25. The method of claim 16, wherein the method comprises treating a CCR2 mediated inflammation in a subject in need thereof by administering to the subject an effective amount of said compound or pharmaceutically acceptable form of said compound in a combination therapy with one or more anti-inflammatory agents, anti-infective agents or immunosuppressive agents.

26. The compound according to claim 1 wherein the cation of Formula (I) is:

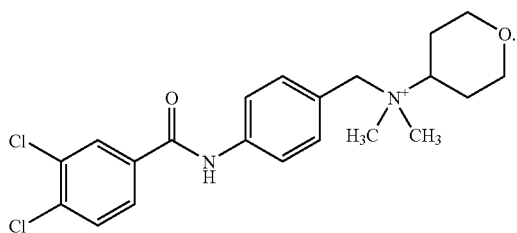

27. The method of claim 16 wherein the CCR2 mediated inflammation is associated with rhinitis, uveitis, asthma, periodontitis, or gingivitis.

28. The method according to claim 16 wherein the cation of Formula (I) is

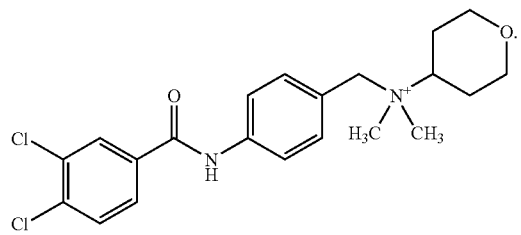

29. The method according to claim 16 wherein the CCR2 mediated inflammation is associated with periodontitis or gingivitis.

30. The method of claim 19 wherein the ophthalmic disorder is uveitis, the asthma is allergic asthma, the periodontal disease is periodontitis or gingivitis and the solid tumor and cancers are carcinomas of the bladder, breast, cervix, colon, lung, prostate or stomach.

31. The method of claim 20 wherein the asthma is allergic asthma.

32. The method of claim 24 wherein the asthma is allergic asthma.

33. The method of claim 16 wherein the CCR2 mediated inflammation is associated with ophthalmic disorder, asthma, periodontal disease, or allergic rhinitis.

34. The method according to claim 33 wherein the periodontal disease is gingivitis or periodontitis and the ophthalmic disorder is uveitis.

35. The method according to claim 27 wherein rhinitis is allergic rhinitis.

* * * * *

UNITED STATES PATENT AND TRADEMARK OFFICE
CERTIFICATE OF CORRECTION

| | |
|---|---|
| PATENT NO. | : 7,799,824 B2 |
| APPLICATION NO. | : 11/159018 |
| DATED | : September 21, 2010 |
| INVENTOR(S) | : Lagu et al. |

It is certified that error appears in the above-identified patent and that said Letters Patent is hereby corrected as shown below:

Column 170, line 27, replace "$R_2$ is $- N^+(R4R_5)-ZR_3;$" with:

$R_2$ is $- N^+(R_4R_5)-ZR_3;$

Signed and Sealed this
Twelfth Day of July, 2011

David J. Kappos
*Director of the United States Patent and Trademark Office*